United States Patent
Due Larsen et al.

(10) Patent No.: US 10,905,745 B2
(45) Date of Patent: Feb. 2, 2021

(54) ACYLATED GLP-1/GLP-2 DUAL AGONISTS

(71) Applicant: Zealand Pharma A/S, Glostrup (DK)

(72) Inventors: Bjarne Due Larsen, Roskilde (DK); Jonathan Griffin, Lund (SE); Lise Giehm, Frederiksberg (DK); Alistair Vincent Gordon Edwards, Copenhagen S (DK)

(73) Assignee: Zealand Pharma A/S, Søborg (DK)

(*) Notice: Subject to any disclaimer, the term of this patent is extended or adjusted under 35 U.S.C. 154(b) by 197 days.

(21) Appl. No.: 16/544,535

(22) Filed: Aug. 19, 2019

(65) Prior Publication Data

US 2019/0365865 A1    Dec. 5, 2019

Related U.S. Application Data

(63) Continuation of application No. 16/195,752, filed on Nov. 19, 2018, now abandoned, which is a continuation of application No. PCT/EP2017/082290, filed on Dec. 11, 2017.

(30) Foreign Application Priority Data

Dec. 9, 2016 (DK) .............................. PA2016 00757

(51) Int. Cl.
    *A61K 38/26*      (2006.01)
    *C07K 14/605*      (2006.01)
    *A61P 3/04*      (2006.01)
    *A61P 3/10*      (2006.01)
    *A61K 38/00*      (2006.01)

(52) U.S. Cl.
CPC .............. *A61K 38/26* (2013.01); *A61P 3/04* (2018.01); *A61P 3/10* (2018.01); *C07K 14/605* (2013.01); *A61K 38/00* (2013.01)

(58) Field of Classification Search
CPC ...... A61K 38/26; A61K 38/00; A61K 47/542; C07K 14/605; A61P 3/04; A61P 3/10
See application file for complete search history.

(56) References Cited

U.S. PATENT DOCUMENTS

| | | |
|---|---|---|
| 2,844,670 A | 7/1958 | Witte |
| 4,288,627 A | 9/1981 | Kubicek |
| 5,118,666 A | 6/1992 | Habener |
| 5,120,712 A | 6/1992 | Habener |
| 5,424,286 A | 6/1995 | Eng |
| 5,432,156 A | 7/1995 | Matsuno et al. |
| 5,512,549 A | 4/1996 | Chen et al. |
| 5,523,449 A | 6/1996 | Prasad et al. |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,789,379 A | 8/1998 | Drucker et al. |
| 5,795,861 A | 8/1998 | Kolterman et al. |
| 5,834,428 A | 11/1998 | Drucker |
| 5,846,747 A | 12/1998 | Thorens et al. |
| 5,846,937 A | 12/1998 | Drucker |
| 5,912,229 A | 6/1999 | Thim et al. |
| 5,952,301 A | 9/1999 | Drucker |
| 5,990,077 A | 11/1999 | Drucker |
| 5,994,500 A | 11/1999 | Drucker et al. |
| 6,006,753 A | 12/1999 | Efendic |
| 6,051,557 A | 4/2000 | Drucker |
| 6,051,689 A | 4/2000 | Thorens |
| 6,110,703 A | 8/2000 | Egel-Mitani et al. |
| 6,114,304 A | 9/2000 | Kolterman et al. |
| 6,136,784 A | 10/2000 | L'Italien et al. |
| 6,184,201 B1 | 2/2001 | Drucker et al. |
| 6,184,208 B1 | 2/2001 | Deigin et al. |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,297,214 B1 | 10/2001 | Drucker |
| 6,329,336 B1 | 12/2001 | Bridon et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,410,511 B2 | 6/2002 | L'Italien et al. |
| 6,451,974 B1 | 9/2002 | Hansen |

(Continued)

FOREIGN PATENT DOCUMENTS

| | | |
|---|---|---|
| EP | 1076066 A1 | 2/2001 |
| EP | 1231218 B1 | 8/2002 |

(Continued)

OTHER PUBLICATIONS

U.S. Appl. No. 14/116,268, Just et al.
U.S. Appl. No. 14/516,216, filed Apr. 23, 2015, Riber et al.
U.S. Appl. No. 14/517,497, filed Apr. 23, 2015, Riber et al.
U.S. Appl. No. 61/784,294, Tolborg et al.
"Zollinger-Ellison Syndrome", The National Institute of Diabetes and Digestive and Kidney Diseases, <https://www.niddk.nih.gov/health-information/digestive-diseases/zollinger-ellison-syndrome>, accessed Oct. 16, 2017 (10 pages).
Action Closing Prosecution in Inter Partes Reexam 95/000,276, mailed Mar. 17, 2011 (25 pages).

(Continued)

*Primary Examiner* — Li N Komatsu
(74) *Attorney, Agent, or Firm* — Clark & Elbing LLP

(57) ABSTRACT

A compound having agonist activity at the GLP-1 (glucagon-like-peptide 1) and GLP-2 (glucagon-like peptide 2) receptors, and a pharmaceutical composition containing the compound or a pharmaceutically acceptable salt or solvate thereof in admixture with a pharmaceutically acceptable carrier, an excipient or a vehicle are provided. The compound can be used, inter alia, in the prophylaxis or treatment of intestinal damage and dysfunction, regulation of body weight, and prophylaxis or treatment of metabolic dysfunction.

5 Claims, No Drawings
Specification includes a Sequence Listing.

(56) References Cited

U.S. PATENT DOCUMENTS

| | | |
|---|---|---|
| 6,458,924 B2 | 10/2002 | Knudsen et al. |
| 6,489,295 B1 | 12/2002 | Drucker et al. |
| 6,506,724 B1 | 1/2003 | Hiles et al. |
| 6,528,486 B1 | 3/2003 | Larsen et al. |
| 6,586,399 B1 | 7/2003 | Drucker |
| 6,703,359 B1 | 3/2004 | Young et al. |
| 6,767,887 B1 | 7/2004 | Hoffmann et al. |
| 6,770,620 B2 | 8/2004 | Henriksen |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 7,049,284 B2 | 5/2006 | Drucker |
| 7,056,734 B1 | 6/2006 | Egan et al. |
| 7,115,569 B2 | 10/2006 | Beeley et al. |
| 7,138,375 B2 | 11/2006 | Beeley et al. |
| 7,153,825 B2 | 12/2006 | Young et al. |
| 7,157,555 B1 | 1/2007 | Beeley et al. |
| 7,176,182 B2 | 2/2007 | Drucker |
| 7,186,683 B2 | 3/2007 | Henriksen et al. |
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |
| 7,348,404 B2 | 3/2008 | Holm et al. |
| 7,371,721 B2 | 5/2008 | Henriksen et al. |
| 7,399,489 B2 | 7/2008 | Kolterman et al. |
| 7,407,932 B2 | 8/2008 | Young et al. |
| 7,411,039 B2 | 8/2008 | Thim et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,563,770 B2 | 7/2009 | Larsen et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,737,251 B2 | 6/2010 | Bridon et al. |
| 7,741,269 B2 | 6/2010 | Young et al. |
| 7,745,403 B2 | 6/2010 | Larsen et al. |
| 7,803,766 B2 | 9/2010 | Cruz |
| 7,858,740 B2 | 12/2010 | Beeley et al. |
| 7,928,065 B2 | 4/2011 | Young et al. |
| 7,935,786 B2 | 5/2011 | Larsen |
| 8,026,210 B2 | 9/2011 | Young et al. |
| 8,057,822 B2 | 11/2011 | Prickett et al. |
| 8,097,698 B2 | 1/2012 | Knudsen et al. |
| 8,163,696 B2 | 4/2012 | Larsen et al. |
| 8,263,550 B2 | 9/2012 | Beeley et al. |
| 8,263,552 B2 | 9/2012 | Larsen et al. |
| 8,288,338 B2 | 10/2012 | Young et al. |
| 8,445,647 B2 | 5/2013 | Prickett et al. |
| 8,642,727 B2 | 2/2014 | Larsen et al. |
| RE45,313 E | 12/2014 | Larsen et al. |
| 9,089,538 B2 | 7/2015 | Neerup et al. |
| 9,125,882 B2 | 9/2015 | Larsen et al. |
| 9,259,477 B2 | 2/2016 | Tolborg et al. |
| 9,453,064 B2 | 9/2016 | Just et al. |
| 9,580,487 B2 | 2/2017 | Larsen et al. |
| 9,649,362 B2 | 5/2017 | Neerup et al. |
| 2001/0021767 A1 | 9/2001 | Drucker et al. |
| 2002/0025933 A1 | 2/2002 | Knudsen et al. |
| 2002/0137666 A1 | 9/2002 | Beeley et al. |
| 2003/0040478 A1 | 2/2003 | Drucker et al. |
| 2003/0109449 A1 | 6/2003 | Drucker et al. |
| 2003/0158101 A1 | 8/2003 | Drucker |
| 2003/0162703 A1 | 8/2003 | Drucker et al. |
| 2003/0207809 A1 | 11/2003 | Drucker |
| 2004/0052862 A1 | 3/2004 | Henriksen et al. |
| 2004/0106547 A1 | 6/2004 | Larsen et al. |
| 2004/0122210 A1 | 6/2004 | Thim et al. |
| 2004/0127418 A1 | 7/2004 | Knudsen et al. |
| 2004/0198642 A1 | 10/2004 | Drucker et al. |
| 2004/0248782 A1 | 12/2004 | Bridon et al. |
| 2005/0282749 A1 | 12/2005 | Henriksen et al. |
| 2006/0057137 A1 | 3/2006 | Steiness |
| 2006/0105954 A1 | 5/2006 | Drucker |
| 2006/0135424 A1 | 6/2006 | Sanguinetti et al. |
| 2006/0194719 A1 | 8/2006 | Ebbehoj et al. |
| 2006/0293232 A1 | 12/2006 | Levy et al. |
| 2007/0111940 A1 | 5/2007 | Larsen et al. |
| 2007/0117752 A1 | 5/2007 | Larsen et al. |
| 2007/0231308 A1 | 10/2007 | Larsen et al. |
| 2009/0082309 A1 | 3/2009 | Bachovchin et al. |
| 2009/0088369 A1 | 4/2009 | Steiness |
| 2011/0098222 A1 | 4/2011 | Larsen et al. |
| 2011/0144008 A1 | 6/2011 | Larsen et al. |
| 2011/0152186 A1 | 6/2011 | Larsen et al. |
| 2011/0245165 A1 | 10/2011 | Larsen et al. |
| 2011/0312878 A1 | 12/2011 | Larsen |
| 2012/0004392 A1 | 1/2012 | Larsen et al. |
| 2012/0289466 A1 | 11/2012 | Larsen et al. |
| 2013/0143793 A1 | 6/2013 | Neerup et al. |
| 2013/0210722 A1 | 8/2013 | Larsen et al. |
| 2014/0080757 A1 | 3/2014 | Tolborg et al. |
| 2014/0154214 A1 | 6/2014 | Larsen et al. |
| 2014/0187483 A1 | 7/2014 | Steiness |
| 2014/0336107 A1 | 11/2014 | Tolborg et al. |
| 2014/0336356 A1 | 11/2014 | Larsen et al. |
| 2015/0111817 A1 | 4/2015 | Riber et al. |
| 2015/0111826 A1 | 4/2015 | Riber et al. |
| 2015/0125431 A1 | 5/2015 | Just et al. |
| 2016/0184400 A1 | 6/2016 | Neerup et al. |
| 2016/0355563 A1 | 12/2016 | Just et al. |
| 2017/0107267 A1 | 4/2017 | Larsen et al. |
| 2017/0137487 A1 | 5/2017 | Larsen et al. |
| 2018/0298077 A1 | 10/2018 | Just et al. |

FOREIGN PATENT DOCUMENTS

| | | |
|---|---|---|
| EP | 1231219 A1 | 8/2002 |
| EP | 0891378 B1 | 11/2002 |
| EP | 0906338 B1 | 11/2002 |
| EP | 1196444 B1 | 6/2003 |
| EP | 1329458 A2 | 7/2003 |
| EP | 0981362 B1 | 11/2003 |
| EP | 1421950 A1 | 5/2004 |
| EP | 1767545 A1 | 3/2007 |
| EP | 2028192 A1 | 2/2009 |
| EP | 1525219 B1 | 5/2009 |
| EP | 0830377 B1 | 10/2009 |
| EP | 2112161 A2 | 10/2009 |
| EP | 1414486 B1 | 5/2010 |
| JP | H07504670 A | 5/1995 |
| JP | 2001011095 A | 1/2001 |
| JP | 2007-525495 A | 9/2007 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-96/32414 A1 | 10/1996 |
| WO | WO-97/31943 A1 | 9/1997 |
| WO | WO-97/39031 A1 | 10/1997 |
| WO | WO-97/46584 A1 | 12/1997 |
| WO | WO-98/03547 A1 | 1/1998 |
| WO | WO-98/05351 A1 | 2/1998 |
| WO | WO-98/08531 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |

(56) References Cited

FOREIGN PATENT DOCUMENTS

| WO | WO-98/50351 A1 | 11/1998 |
|---|---|---|
| WO | WO-98/52600 A1 | 11/1998 |
| WO | WO-99/07404 A1 | 2/1999 |
| WO | WO-99/25727 A2 | 5/1999 |
| WO | WO-99/25728 A1 | 5/1999 |
| WO | WO-99/40788 A1 | 8/1999 |
| WO | WO-99/43707 A1 | 9/1999 |
| WO | WO-99/43708 A1 | 9/1999 |
| WO | WO-99/46283 A1 | 9/1999 |
| WO | WO-99/49788 A1 | 10/1999 |
| WO | WO-99/58144 A1 | 11/1999 |
| WO | WO-99/64060 A1 | 12/1999 |
| WO | WO-00/09666 A1 | 2/2000 |
| WO | WO-00/41546 A2 | 7/2000 |
| WO | WO-00/41548 A2 | 7/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | WO-01/04156 A1 | 1/2001 |
| WO | WO-01/32158 A2 | 5/2001 |
| WO | WO-01/41779 A1 | 6/2001 |
| WO | WO-02/24214 A2 | 3/2002 |
| WO | WO-02/34285 A2 | 5/2002 |
| WO | WO-02/066511 A2 | 8/2002 |
| WO | WO-02/098348 A2 | 12/2002 |
| WO | WO-03/022304 A1 | 3/2003 |
| WO | WO-2004/005342 A1 | 1/2004 |
| WO | WO-2004/035624 A2 | 4/2004 |
| WO | WO-2005/027978 A2 | 3/2005 |
| WO | WO-2005/072045 A2 | 8/2005 |
| WO | WO-2005/077072 A2 | 8/2005 |
| WO | WO-2005/082404 A2 | 9/2005 |
| WO | WO-2006/117565 A2 | 11/2006 |
| WO | WO-2007/095737 A1 | 8/2007 |
| WO | WO-2007/100535 A2 | 9/2007 |
| WO | WO-2008/056155 A1 | 5/2008 |
| WO | WO-2008/071010 A1 | 6/2008 |
| WO | WO-2008/071972 A1 | 6/2008 |
| WO | WO-2008/101017 A2 | 8/2008 |
| WO | WO-2008/152403 A1 | 12/2008 |
| WO | WO-2009/077737 A2 | 6/2009 |
| WO | WO-2009/155257 A1 | 12/2009 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/096052 A1 | 8/2010 |
| WO | WO-2011/006497 A1 | 1/2011 |
| WO | WO-2011/084808 A2 | 7/2011 |
| WO | WO-2011/088837 A1 | 7/2011 |
| WO | WO-2011/134471 A1 | 11/2011 |
| WO | WO-2011/143335 A2 | 11/2011 |
| WO | WO-2011/160630 A2 | 12/2011 |
| WO | WO-2012/158965 A2 | 11/2012 |
| WO | WO-2013/164484 A1 | 11/2013 |
| WO | WO-2015/067715 A2 | 5/2015 |
| WO | WO-2016/066818 A1 | 5/2016 |
| WO | WO-2018/103868 A1 | 6/2018 |
| WO | WO-2018/104558 A1 | 6/2018 |
| WO | WO-2018/104559 A1 | 6/2018 |
| WO | WO-2018/104560 A1 | 6/2018 |
| WO | WO-2018/104561 A1 | 6/2018 |

OTHER PUBLICATIONS

Alison et al., "The role of growth factors in gastrointestinal cell proliferation," Cell Biol Int. 18(1):1-10 (1994).
Ally et al., "Rapid determination of creatine, phosphocreatine, purine bases and nucleotides (ATP, ADP, AMP, GTP, GDP) in heart biopsies by gradient ion-pair reversed-phase liquid chromatography," J Chromatogr. 575(1):19-27 (1992).
Altschul et al., "Local alignment statistics," Methods Enzymol. 226:460-80 (1996).
Bailey et al., "Glucagon-like peptide-1 and the entero-insular axis in obese hyperglycaemic (ob/ob) mice," Life Sci. 40(6):521-525 (1987).
Baldassano et al., "GLP-2: What do we know? What are we going to discover?," Regul Pept. 194-195:6-10 (2014).
Baldwin et al., "Gut hormones, growth and malignancy," Baillière's Clin Endocrinol Metab. 8(1):185-214 (1994).
Bamba et al., "Enteroglucagon. A putative humoral factor including pancreatic hyperplasia after proximal small bowel resection," Dig Dis Sci. 39(7):1532-36 (1994).
Ban et al., "Cardioprotective and vasodilatory actions of glucagon-like peptide 1 receptor are mediated through both glucagon-like peptide 1 receptor-dependent and -independent pathways," Circulation. 117(18):2340-2350 (2008).
Barragán et al., "Changes in arterial blood pressure and heart rate induced by glucagon-like peptide-1-(7-36) amide in rats," Am J Physiol. 266(3 Pt1):E459-66 (1994).
Bedford et al., "Amino acid structure and 'difficult sequences' in solid phase peptide synthesis," Int J Peptide Protein Res. 40(3-4):300-7 (1992).
Behme et al., "Glucagon-like peptide 1 improved glycemic control in Type 1 diabetes," BMC Endocr Disord. 3(1):3 (2003) (9 pages).
Benjamin et al., "Glucagon-like peptide-2 enhances intestinal epithelial barrier function of both transcellular and paracellular pathways in the mouse," Gut. 47(1):112-9 (2000).
Bloom, "Gut hormones in adaptation," Gut. 28(Suppl):31-5 (1987).
Booth et al., "Teduglutide ([Gly2]GLP-2) protects small intestinal stem cells from radiation damage," Cell Prolif. 37(6):385-400 (2004).
Boushey et al., "Glucagon-like peptide (GLP)-2 reduces chemotherapy-associated mortality and enhances cell survival in cells expressing a transfected GLP-2 receptor," Cancer Res. 61(2):687-93 (2001).
Boushey et al., "Glucagon-like peptide 2 decreases mortality and reduces the severity of indomethacin-induced murine enteritis," Am J Physiol. 227(5 Pt 1):E937-47 (1999).
Bowie et al., "Deciphering the message in protein sequences: tolerance to amino acid substitutions," Science. 247(4948):1306-10 (1990).
Brubaker et al., "Alterations in proglucagon processing and inhibition of proglucagon gene expression in transgenic mice which contain a chimeric proglucagon-SV40 T antigen gene," J Biol Chem. 267(29):20728-33 (1992).
Burcelin et al., "Long-lasting antidiabetic effect of a dipeptidyl peptidase IV-resistant analog of glucagon-like peptide-1," Metabolism. 48(2):252-258 (1999).
Buse et al., "The effect of epinephrine, glucagon, and the nutritional state on the oxidation of branched chain amino acids and pyruvate by isolated hearts and diaphragms of the rat," J Biol Chem. 248(2):697-706 (1973).
Buse, "Progressive use of medical therapies in type 2 diabetes," Diabetes Spectrum. 13(4):211-20 (2000).
Byrne et al., "Inhibitory effects of hyperglycaemia on fed jejunal motility: potential role of hyperinsulinaemia," Eur J Clin Invest. 28(1):72-78 (1998).
Carpenter et al., "Rational design of stable lyophilized protein formulations: some practical advice," Pharm Res. 14(8):969-75 (1997).
Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).
Cheeseman, "Upregulation of SGLT-1 transport activity in rat jejunum induced by GLP-2 infusion in vivo," Am J Physiol. 273(6 Pt 2):R1965-71 (1997).
Chen et al., "Evidence that the diabetes gene encodes the leptin receptor: identification of a mutation in the leptin receptor gene in db/db mice," Cell. 84(3):491-5 (1996).
Chen et al., "Tissue-specific expression of unique mRNAs that encode proglucagon-derived peptides or exendin 4 in the lizard," J Biol Chem. 272(7):4108-15 (1997).
Christensen et al., "Lixisenatide, a novel GLP-1 receptor agonist for the treatment of type 2 diabetes mellitus," IDrugs 12(8):503-13 (2009).

(56) References Cited

OTHER PUBLICATIONS

Cleland et al., "The development of stable protein formulations: a close look at protein aggregation, deamidation, and oxidation," Crit Rev Ther Drug Carrier Syst. 10(4):307-77 (1993).
Code, "The digestive system," Annu Rev Physiol. 15:107-38 (1953).
Cohen et al., "Oxyntomodulin suppresses appetite and reduces food intake in humans," J Clin Endocrinol Metab. 88(10):4696-4701 (2003).
Coleman, "Effects of parabiosis of obese with diabetes and normal mice," Diabetologia. 9(4):294-8 (1973).
Creson et al., "Powdered duodenal extract in the treatment of peptic ulcer," Am J Gastroenterol. 33:359-65 (1960).
Curriculum Vitae (CV) of Keld Fosgerau, Ph.D. (9 pages), Jan. 11, 2010.
D'Alessio et al., "Glucagon-like peptide 1 enhances glucose tolerance both by stimulation of insulin release and by increasing insulin-independent glucose disposal," J Clin Invest. 93(5):2263-66 (1994).
DaCambra et al., "Structural determinants for activity of glucagon-like peptide-2," Biochemistry. 39(30):8888-94 (2000).
Dakin et al., "Peripheral oxyntomodulin reduces food intake and body weight gain in rats," Endocrinology. 145(6):2687-2695 (2004).
De Boer et al., "The tac promoter: a functional hybrid derived from the trp and lac promoters," Proc Natl Acad Sci USA. 80(1):21-5 (1983).
Deacon et al., "Dipeptidyl peptidase IV inhibition potentiates the insulinotropic effect of glucagon-like peptide 1 in the anesthetized pig," Diabetes. 47(5):764-9 (1998).
Deacon et al., "Dipeptidyl peptidase IV resistant analogues of glucagon-like peptide-1 which have extended metabolic stability and improved biological activity," Diabetologia. 41(3):271-8 (1998).
Decision in Inter Partes Reexam for U.S. Appl. No. 95/000,276, mailed Nov. 25, 2013 (29 pages).
Delgado et al., "The uses and properties of PEG-linked proteins," Crit Rev Ther Drug Carrier Syst. 9(3,4):249-304 (1992).
Dickstein et al., "ESC Guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM)," Eur Heart J. 29(19):2388-442 (2008).
Drucker et al., "Biologic properties and therapeutic potential of glucagon-like peptide-2," JPEN J Patenter Enteral Nutr. 23(5):S98-100 (1999).
Drucker et al., "Human [Gly2]GLP-2 reduces the severity of colonic injury in a murine model of experimental colitis," Am J Physiol. 276(1 Pt 1):G79-91 (1999).
Drucker et al., "Induction of intestinal epithelial proliferation by glucagon-like peptide 2," Proc Nat Acad Sci U.S.A. 93(15):7911-6 (1996).
Drucker et al., "Physiology and pharmacology of the enteroendocrine hormone glucagon-like peptide-2," Annu Rev Physiol. 76:561-83 (2014).
Drucker et al., "Regulation of the biological activity of glucagon-like peptide 2 in vivo by dipeptidyl peptidase IV," Nat Biotechnol. 15(7):673-7 (1997).
Drucker, "Glucagon-like peptide 2," J Clin Endocrinol Metab. 86(4):1759-64 (2001).
Drucker, "Glucagon-like peptides," Diabetes. 47(2):159-69 (1998).
Drucker, "Minireview: The glucagon-like peptides," Endocrinology. 142(2):521-7 (2001).
Edvell et al., "Initiation of increased pancreatic islet growth in young normoglycemic mice (Umeå +/?)," Endocrinology. 140(2):778-83 (1999).
Ehrlich, "DNA cloning in Bacillus subtilis," Proc Natl Acad Sci USA. 75(3):1433-6 (1978).
EMEA Humalog Information: European Public Assessment Report (EPAR) and Scientific Discussions, 2006 (11 pages).

Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
Estall et al., "Dual Regulation of Cell Proliferation and Survival via Activation of Glucagon-Like Peptide-2 Receptor Signaling," J Nutr. 133(11):3708-11 (2003).
European Search Opinion and Extended European Search Report for European Patent Application No. 08016668.9, dated Jan. 27, 2009 (5 pages).
European Search Report for European Patent Application No. 09002937, dated Mar. 15, 2010 (5 pages).
European Search Report for European Patent Application No. 99610043, dated Jan. 18, 2000 (2 pages).
Experimental Report provided in response to opposition filed against European Patent No. 1525219, filed Oct. 5, 2011 (4 pages).
Extended European Search Report for European Patent Application No. 08016668, dated Jan. 14, 2009 (4 pages).
Extended European Search Report for European Patent Application No. 11774431.8, dated Sep. 30, 2013 (11 pages).
Farah et al., "Studies on the pharmacology of glucagon," J Pharmacol Exp Ther. 129:49-55 (1960).
Feinberg et al., "Period and amplitude analysis of 0.5-3 c/sec activity in NREM sleep of young adults," Electroencephalogr Clin Neurophysiol. 44(2):202-13 (1978).
Ferrone et al., "Teduglutide for the treatment of short bowel syndrome," Ann Pharmacother. 40(6):1105-9 (2006).
Fineman et al., "AC2993 (Synthetic Exendin-4) Improved Glycemic Control in Patients With Type 2 Diabetes During 28 Days of Treatment in a Multicenter, Randomized, Triple-Blind, Placebo-Controlled Study," Diabetes 51 (Supplement 2):A85, Abstract 343-OR, Abstract Book 62"d Scientific Sessions. Poster. Jun. 14-18, 2002.
Fineman et al., Abstract 343-OR: "AC2993 (Synthetic Exendin-4) added to existing metformin (Met) and/or Sulfonylurea (SFU) treatment improved glycemic control in patients with type 2 diabetes (DM2) during 28 days of treatment," Diabetes. 51(Supplement 2):A85, Abstract Book, 62nd Scientific Sessions (2002) (3 pages).
Fosgerau et al., "The novel GLP-1-gastrin dual agonist, ZP3022, increases beta-cell mass and prevents diabetes in db/db mice, " Diabetes Obes Metab. 15(1):62-71 (2013).
Francis et al., "PEGylation of cytokines and other therapeutic proteins and peptides: the importance of biological optimisation of coupling techniques," Int J Hematol. 68(1):1-18 (1998).
Gadermann et al., "[Treatment of gastroduodenal ulcerations & inflammations with the tissue extract robadin]," Med Klin (Munich). 54(16):774-8 (1959) (English translation).
Gibson et al., "Irinotecan causes severe small intestinal damage, as well as colonic damage, in the rat with implanted breast cancer," J Gastroenterol Hepatol. 18(9):1095-100 (2003).
Gibson et al., "Relative roles of spatial and intensive cues in the discrimination of spatial tactile stimuli," Percept Pyschophys. 64(7):1095-107 (2002).
Glass et al., "Studies on robuden, extract from stomach and duodenum: its effects upon gastric secretion and clinical course of peptic ulcer," Am J Dig Dis. 4(12):988-1013 (1959).
Gombotz et al. "Biodegradable polymers for protein and peptide drug delivery," Bioconjug Chem. 6(4):332-351 (1995).
Gregor et al., "The role of gut-glucagon-like immunoreactants in the control of gastrointestinal epithelial cell renewal," Digestion. 46(Suppl 2):59-65 (1990).
Greig et al., "Once daily injection of exendin-4 to diabetic mice achieves long-term beneficial effects on blood glucose concentrations," Diabetologia. 42(1):45-50 (1999).
Grey et al., "A growth-stimulating activity derived from the proximal small intestine is associated with an adaptive response, " Can J Physiol Pharmacol. 68(5):646-9 (1990).
Grey et al., "Detection of growth-stimulating activity in the proximal small intestine during weaning in the suckling rat," Biol Neonate. 59(1):37-45 (1991).

(56) References Cited

OTHER PUBLICATIONS

Grey et al., "Evidence for a growth-stimulating fraction in the rat proximal intestine after small bowel resection," Gastroenterology. 89(6):1305-12 (1985).
Grieve et al., "Emerging cardiovascular actions of the incretin hormone glucagon-like peptide-1: Potential therapeutic benefits beyond glycaemic control?," Br J Pharmacol. 157(8):1340-51 (2009).
Grounds of Appeal by F. Hoffmann-La Roche AG for European Patent No. 1525219, filed Aug. 10, 2012 (35 pages).
Grounds of Appeal by Novo Nordisk A/S for European Patent No. 1525219, filed Aug. 3, 2012 (27 pages).
Guan et al., "GLP-2-mediated up-regulation of intestinal blood flow and glucose uptake is nitric oxide-dependent in TPN-fed piglets," Gastroenterology. 125(1):136-47 (2003).
Gunn et al., "Central glucagon-like peptide-I in the control of feeding," Biochem Soc Trans. 24(2):581-4 (1996).
Guo et al., "3'-end-forming signals of yeast mRNA," Mol Cell Biol. 15(11):5983-90 (1995).
Göke et al., "Distribution of GLP-1 binding sites in the rat brain: Evidence that exendin-4 is a ligand of brain GLP-1 binding sites," Eur J Neurosci. 7(11):2294-2300 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Haffner et al., "Intensive lifestyle intervention or metformin on inflammation and coagulation in participants with impaired glucose tolerance," Diabetes. 54(5):1566-72 (2005).
Hamad et al., "Pharmacologic therapy of chronic heart failure," Am J Cardiovasc Drugs. 7(4):235-48 (2007).
Harikae, "The effects of a behavioral program in the obese NIDDM patients-observations on daily activity, degree of obesity and blood sugar control," Bulletin of the School of Nursing, Yamaguchi Prefectural University 2:1-13/E (1998) (Abstract in English).
Heinrich et al., "Pre-proglucagon messenger ribonucleic acid: nucleotide and encoded amino acid sequences of the rat pancreatic complementary deoxyribonucleic acid," Endocrinology. 115(6):2176-81 (1984).
Holst, "Enteroglucagon," Annu Rev Physiol. 59:257-71 (1997).
Holst, "Glucagon-like peptide-1, a gastrointestinal hormone with a pharmaceutical potential," Curr Med Chem. 6(11):1005-17 (1999).
Holst, "The physiology of glucagon-like peptide 1," Physiol Rev. 87(4): 1409-39 (2007).
Hudecz et al., "Synthesis, conformation, biodistribution, and in vitro cytotoxicity of daunomycin-branched polypeptide conjugates," Bioconjug Chem. 3(1):49-57 (1992).
Hui et al., "The short half-life of glucagon-like peptide-1 in plasma does not reflect its long-lasting beneficial effects," Eur J Endocrinol. 146(6):863-9 (2002).
ICH Harmonised Tripartite Guideline, Feb. 5, 1998 (39 pages).
Igaki et al.,"Investigation of effectiveness of low intensity exercise on body fat reduction in diabetics," J.Japan Phys Ther Assoc, 26:270-4 (1999). English abstract included.
Ingwall et al., "Is the failing heart energy starved? On using chemical energy to support cardiac function," Circ Res. 95(2):135-45 (2004).
International Dictionary of Medicine and Biology in Three Volumes: vol. II. John Wiley & Sons, New York,1328 (1986) (3 pages).
International Preliminary Examination Report for International Application No. PCT/DK03/00463, dated Sep. 20, 2004 (5 pages).
International Preliminary Report on Patentability for International Application No. PCT/EP2017/082290, dated Jun. 20, 2019 (14 pages).
International Preliminary Report on Patentability from PCT/GB2006/001633, dated Nov. 6, 2007 (10 pages).
International Preliminary Report on Patentability from PCT/GB2007/004273, dated May 12, 2009 (9 pages).
International Search Report and Written Opinion for International Application No. PCT/IB2012/001090, dated Jan. 25, 2013 (15 pages).
International Search Report and Written Opinion for International Application No. PCT/EP2013/059320, dated Aug. 8, 2013 (11 pages).
International Search Report and Written Opinion for International Patent Application No. PCT/EP2012/071766, dated Feb. 15, 2013 (9 pages).
International Search Report for International Application No. PCT/DK00/00393, dated Nov. 8, 2000 (3 pages).
International Search Report for International Application No. PCT/DK03/00463, dated Oct. 22, 2003 (7 pages).
International Search Report for International Application No. PCT/DK2011/050133 dated Oct. 6, 2011 (5 pages).
International Search Report for International Application No. PCT/DK2011/050018, dated May 30, 2011 (6 pages).
International Search Report from PCT/GB2006/001633, dated Oct. 24, 2006 (6 pages).
International Search Report from PCT/GB2007/004273, dated Apr. 14, 2008 (4 pages).
International Search Report received in connection with International Patent Application No. PCT/EP2017/082290, dated Feb. 13, 2018 (5 pages).
Irwin et al., "Trout and chicken proglucagon: alternative splicing generates mRNA transcripts encoding glucagon-like peptide 2," Mol Endocrinol. 9(3):267-77 (1995).
Ivory et al., "Interleukin-10-independent anti-inflammatory actions of glucagon-like peptide 2," Am J Physiol Gastrointest Liver Physiol. 295(6): G1202-10 (2008).
Jenkins et al., "Mechanisms of small intestinal adaptation," Dig Dis. 12(1):15-27 (1994).
Jeppesen et al., "Teduglutide (ALX-0600), a dipeptidyl peptidase IV resistant glucagon-like peptide 2 analogue, improves intestinal function in short bowel syndrome patients," Gut. 54(9):1224-31 (2005).
Jeppesen, "The use of hormonal growth factors in the treatment of patients with short-bowel syndrome," Drugs. 66(5):581-9 (2006).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation.," Circulation. 119(14):1977-2016 (2009).
Juntti-Berggren et al., "The antidiabetogenic effect of GLP-1 is maintained during a 7-day treatment period and improves diabetic dyslipoproteinemia in NIDDM patients," Diabetes Care. 19(11):1200-6 (1996).
Keefe et al., "Chemotherapy for cancer causes apoptosis that precedes hypoplasia in crypts of the small intestine in humans," Gut. 47(5):632-7 (2000).
Kieffer et al., "The glucagon-like peptides," Endocr Rev. 20(6):876-913 (1999).
Kitamura, "Is the "drug holiday" harmful?," Keio J Med. 25(3):131-7 (1976).
Kiyose et al., "Glucose tolerance screening method using a combination of fasting plasma glucose and hemoglobin A1c," J. Japan Diab Soc, 30:325-331 (1987). English abstract included.
Korc, "Islet growth factors: curing diabetes and preventing chronic pancreatitis?," J Clin Invest. 92(3):1113-4 (1993).
Krchnák et al., "Aggregation of resin-bound peptides during solid-phase peptide synthesis. Prediction of difficult sequences," Int J Pept Protein Res. 42(5):450-4 (1993).
Kyte et al., "A simple method for displaying the hydropathic character of a protein," J Mol Biol. 157(1):105-32 (1982).
Larsen et al., "Glucagon-like peptide-1 infusion must be maintained for 24 h/day to obtain acceptable glycemia in type 2 diabetic patients who are poorly controlled on sulphonylurea treatment," Diabetes Care. 24(8):1416-21 (2001).
Larsen et al., "Incomplete Fmoc deprotection in solid-phase synthesis of peptides," Int J Pept Protein Res. 43(1):1-9 (1994).
Larsen et al., "Sequence-assisted peptide synthesis (SAPS)," J Peptide Res. 52(6):470-6 (1998).
Lee et al., "Enteroendocrine-derived glucagon-like peptide-2 controls intestinal amino acid transport," Mol Metab. 6(3):245-255 (2017).

(56) References Cited

OTHER PUBLICATIONS

Leiter et al., "Influence of dietary carbohydrate on the induction of diabetes in C57BL/KsJ-db/db diabetes mice," J Nutr. 113(1):184-95 (1983).
Lentze, "Intestinal adaptation in short-bowel syndrome," Eur J Pediatr. 148(4):294-9 (1989).
Levey et al., "Activation of adenyl cyclase by glucagon in cat and human heart," Circ Res. 24(2):151-6 (1969).
Lopaschuk et al., "Measurements of fatty acid and carbohydrate metabolism in the isolated working rat heart," Mol Cell Biochem. 172(1-2):137-47 (1997).
Lopez et al., "Mammalian pancreatic preproglucagon contains three glucagon-related peptides," Proc Natl Acad Sci U.S.A. 80(18):5485-9 (1983).
Loyter et al., "Mechanisms of DNA uptake by mammalian cells: fate of exogenously added DNA monitored by the use of fluorescent dyes," Proc Natl Acad Sci USA. 79(2):422-6 (1982).
López-Delgado et al., "Effects of glucagon-like peptide 1 on the kinetics of glycogen synthase a in hepatocytes from normal and diabetic rats," Endocrinology. 139(6):2811-17 (1998).
Manning et al., "Stability of protein pharmaceuticals," Pharm Res. 6(11):903-18 (1989).
Matthes et al., "Simultaneous rapid chemical synthesis of over one hundred oligonucleotides on a microscale," EMBO J. 3(4):801-5 (1984).
Mayer et al., "Effect of glucagon on cyclic 3',5'-AMP, phosphorylase activity and contractility of heart muscle of the rat," Circ Res. 26(2):225-33 (1970).
Meier et al., "Absence of a memory effect for the insulinotropic action of glucagon-like peptide 1 (GLP-1) in healthy volunteers," Horm Metab Res. 35(9):551-6 (2003).
Meier et al., "Glucagon-like peptide 2 stimulates glucagon secretion, enhances lipid absorption, and inhibits gastric acid secretion in humans," Gastroenterology. 130(1):44-54 (2006).
Mentlein et al., "Dipeptidyl-peptidase IV hydrolyses gastric inhibitory polypeptide, glucagon-like peptide-1(7-36)amide, peptide histidine methionine and is responsible for their degradation in human serum," Eur J Biochem. 214(3):829-35 (1993).
Meurer et al., "Properties of native and in vitro glycosylated forms of the glucagon-like peptide-1 receptor antagonist exendin (9-39)," Metabolism. 48(6):716-24 (1999).
Meyer et al., Effects of conformation on the Chemical Stability of Pharmaceutically Relevant Polypeptides. *Rational design of stable protein formulations*. Carpenter and Manning, 85-6 (2002).
Miazza et al., "Hyperenteroglucagonaemia and small intestinal mucosal growth after colonic perfusion of glucose in rats," Gut. 26(5):518-24 (1985).
Mojsov, "Structural requirements for biological activity of glucagon-like peptide-I," Int J Pept Protein Res. 40(3-4):333-43 (1992).
Moon et al., "Tyr1 and Ile7 of glucose-dependent insulinotropic polypeptide (GIP) confer differential ligand selectivity toward GIP and glucagon-like peptide-1 receptors," Mol Cells. 30(2):149-54 (2010).
Moore et al.,"GLP-2 receptor agonism ameliorates inflammation and gastrointestinal stasis in murine postoperative ileus," J Pharmacol Exp Ther. 333(2):574-83 (2010).
Myojo et al., "Trophic effects of glicentin on rat small-intestinal mucosa in vivo and in vitro," J Gastroenterol. 32(3):300-5 (1997) (English abstract).
Nauck et al., "Glucagon-like peptide 1 and its potential in the treatment of non-insulin-dependent diabetes mellitus," Horm Metab Res. 29(9):411-6 (1997).
Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem 67(5):1982-91 (1996).
Neubauer et al., "Myocardial phosphocreatine-to-ATP ratio is a predictor of mortality in patients with dilated cardiomyopathy," Circulation. 96(7):2190-6 (1997) (9 pages).

Neumann et al., "Gene transfer into mouse lyoma cells by electroporation in high electric fields," EMBO J. 1(7):841-5 (1982).
Neumann, "Experiences with medications: A review of 12 years of peptic ulcer treatment with Robuden," Schweiz Med Wochenschr. 87(32):1049-1051 (1957) (English translation).
Nikolaidis et al., "Active metabolite of GLP-1 mediates myocardial glucose uptake and improves left ventricular performance in conscious dogs with dilated cardiomyopathy," Am J Physiol Heart Circ Physiol. 289(6):H2401-8 (2005).
Nikolaidis et al., "Recombinant glucagon-like peptide-1 increases myocardial glucose uptake and improves left ventricular performance in conscious dogs with pacing-induced dilated cardiomyopathy," Circulation. 110(8):955-61 (2004).
Notarized Affidavit from the British Library regarding European Journal of Endocrinology, vol. 146, No. 6, Jun. 2002, mailed Apr. 21, 2011 (5 pages).
Notice of Appeal of Opposition Decision for European Patent No. 1525219 by F. Hoffmann-La Roche AG, filed May 21, 2012 (1 page).
Notice of Appeal of Opposition Decision for European Patent No. 1525219 by Novo Nordisk A/S, filed Apr. 23, 2012 (1 page).
Notice of Opposition for European Patent No. EP1877435, mailed on Nov. 22, 2011 (29 pages).
Notice of Opposition to a European Patent for European U.S. Pat. No. 1525219 on behalf of Novo Nordisk A/S, dated Feb. 25, 2010 (24 pages).
Notkin et al., "Gastroduodenal tissue extracts in the treatment of peptic ulcer with special reference to the effectiveness of robuden," Am J Dig Dis. 21(9):251-61 (1954).
O'Shaughnessy et al., "Alpha-difluoromethylornithine as treatment for metastatic breast cancer patients," Clin Cancer Res. 5(11):3438-44 (8 pages) (1999).
Oben et al., "Effect of the entero-pancreatic hormones, gastric inhibitory polypeptide and glucagon-like polypeptide-1(7-36) amide, on fatty acid synthesis in explants of rat adipose tissue," J Endocrinol. 130(2):267-72 (1991).
Office Action issued for Japanese Patent Application No. 2008-509505, dated Sep. 6, 2011 (11 pages).
Opposition to European Patent No. 1525219 on behalf of F. Hoffman-La Roche AG, dated Feb. 25, 2010 (34 pages).
Orskov, "Glucagon-like peptide-1, a new hormone of the entero-insular axis," Diabetologia. 35(8):701-11 (1992).
Owens et al., "Insulins today and beyond," Lancet. 358(9283):739-46 (2001).
Parkes et al., "Insulinotropic actions of exendin-4 and glucagon-like peptide-1 in vivo and in vitro," Metabolism. 50(5):583-9 (2001).
Partial European Search Report for European Patent Application No. 03005786, dated Oct. 23, 2003 (6 pages).
Partial European Search Report for European Patent Application No. 99610043, dated Jan. 18, 2000 (4 pages).
PDR Medical Dictionary. Medical Economics, Montvale, New Jersey, p. 522 (1995) (3 pages).
Pederson et al., "Improved glucose tolerance in Zucker Fatty Rats by oral administration of the dipeptidyl peptidase IV inhibitor isoleucine thiazolidide," Diabetes. 47(8):1253-8 (1998).
Petersen et al., "Administration of the protease-resistant glucagon-like peptide 2 analog, [gly2]GLP-2, prior to and concurrently with the chemotherapeutic agent, 5-fluorouracil, inhibits small intestinal atrophy and attenuates bodyweight loss in mice," Gastroenterol. 128(4; Supplement 2): A188 (2005) (1 page).
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002, *Diabetologia* 45 (Suppl. 1):A147, Abstract No. 447 (2002) (2 pages).
Pocai et al., "Glucagon-like peptide 1/glucagon receptor dual agonism reverses obesity in mice," Diabetes. 58(10):2258-66 (2009).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273(16):9778-84 (1998).

(56) References Cited

OTHER PUBLICATIONS

Poon et al., "Exenatide improves glycemic control and reduces body weight in subjects with type 2 diabetes: a dose-ranging study," Diabetes Technol Ther. 7(3):467-77 (2005).

Pouliot et al., "Follow-up studies on peptic ulcer patients treated with robuden," Can Med Assoc J. 82:524-8 (1960).

Pratesi et al., "Poly-L-aspartic acid as a carrier for doxorubicin: a comparative in vivo study of free and polymer-bound drug," Br J Cancer. 52(6):841-848 (1985).

Prescribing information for Victoza, 6 mg/ml solution for injection in pre-filled pen, as submitted on Aug. 13, 2012 as part of a Grounds of Appeal for European Patent No. 1525219 (31 pages).

Pridal et al., "Absorption of glucagon-like peptide-1 can be protracted by zinc or protamine," Int J Pharm. 136(1-2):53-9 (1996).

Raufman et al., "Exendin-3, a novel peptide from *Heloderma horridum* venom, interacts with vasoactive intestinal peptide receptors and a newly described receptor on dispersed acini from guinea pig pancreas. Description of exendin-3(9-39) amide, a specific exendin receptor antagonist," J Biol Chem. 266(5):2897-902 (1991).

Raufman et al., "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).

Raufman, "Bioactive peptides from lizard venoms," Regul Pept. 61(1):1-18 (1996).

Response to Notice of Opposition for European Patent No. 1877435, filed Jun. 25, 2012 (6 pages).

Richter et al., "GLP-1 stimulates secretion of macromolecules from airways and relaxes pulmonary artery," Am J Physiol. 265(4 Pt 1):L374-81 (1993).

Ritzel et al., "A synthetic glucagon-like peptide-1 analog with improved plasma stability," J Endocrinol. 159(1):93-102 (1998).

Roach et al., "Improved postprandial glycemic control during treatment with humalog Mix25, a novel protamine-based insulin lispro formulation. Humalog Mix25 Study Group," Diabetes Care. 22(8):1258-61 (1999).

Robberecht et al., "Comparative efficacy of seven synthetic glucagon analogs, modified in position 1, 2, and/or 12, on liver and heart adenylate cyclase from rat," Peptides. 7(Suppl 1):109-12 (1986).

Rolin et al., "The long-acting GLP-1 derivative NN2211 ameliorates glycemia and increases beta-cell mass in diabetic mice," Am J Physiol Endocrinol Metab. 283(4):E745-52 (2002).

Rooman et al., "Gastrin stimulates beta-cell neogenesis and increases islet mass from transdifferentiated but not from normal exocrine pancreas tissue," Diabetes. 51(3):686-90 (2002).

Ruiz-Grande et al., "Lipolytic action of glucagon-like peptides in isolated rat adipocytes," Peptides. 13(1):13-6 (1992).

Saraceni et al., "Effects of glucagon-like peptide-1 and long-acting analogues on cardiovascular and metabolic function," Drugs R D. 8(3):145-53 (2007).

Sasaki et al., "Enteroglucagon, but not CCK, plays an important role in pancreatic hyperplasia after proximal small bowel resection," J Gastroenterol Hepatol. 9(6):576-81 (1994).

Sinclair et al., "Proglucagon-derived peptides: mechanisms of action and therapeutic potential," Physiology (Bethesda). 20:357-65 (2005).

Singh et al., "Use of 125I-[Y39]exendin-4 to characterize exendin receptors on dispersed pancreatic acini and gastric chief cells from guinea pig," Regul Pept. 53(1):47-59 (1994).

Skarbaliene et al., "ZP1848, a novel GLP-2 agonist, provides a wide window of therapeutic efficacy in the experimental Crohn's disease model," Gastroenterol. 140(5 Suppl 1):S-519, abstract Su1953 (2011) (1 page).

Sowden et al., "Oxyntomodulin increases intrinsic heart rate in mice independent of the glucagon-like peptide-1 receptor," Am J Physiol Regul Integr Comp Physiol. 292(2): R962-70 (2007) (10 pages).

Sporn et al., "Chemoprevention of cancer," Carcinogenesis. 21(3):525-530 (2000).

Stoffers et al., "Insulinotropic glucagon-like peptide 1 agonists stimulate expression of homeodomain protein IDX-1 and increase islet size in mouse pancreas," Diabetes. 49(5):741-8 (2000).

Suarez-Pinzon et al., "Combination therapy with epidermal growth factor and gastrin increases beta-cell mass and reverses hyperglycemia in diabetic NOD mice," Diabetes. 54(9):2596-601 (2005).

Suarez-Pinzon et al., "Combination therapy with glucagon-like peptide-1 and gastrin induces beta-cell neogenesis from pancreatic duct cells in human islets transplanted in immunodeficient diabetic mice," Cell Transplant. 17(6):631-40 (2008).

Suarez-Pinzon et al., "Combination therapy with glucagon-like peptide-1 and gastrin restores normoglycemia in diabetic NOD mice," Diabetes. 57(12):3281-8 (2008).

Submission in opposition proceedings made following summons to attend oral proceedings for European Patent No. 1877435, filed Jan. 13, 2014 (103 pages).

Suda, "The organ distribution and molecular forms of glucagon-related peptides," Yamagata Med J. 6(2):149-161 (1988) (English translation).

Table filed for European Application No. EP1877435B, on Jan. 14, 2014 (1 page).

Table of Claims anticipated by WO 00/09666, as submitted on Feb. 25, 2010 as part of an Opposition to European Patent No. 1525219 (9 pages).

Table of selected data from International Application No. 97/39031 filed by P during the oral proceedings of European Patent Application No. EP1877435B on Mar. 13, 2014 (1 page).

Tamaki et al., "Apoptosis in normal tissues induced by anti-cancer drugs," J Int Med Res. 31(1):6-16 (2003).

Tang-Christensen et al., "Central administration of GLP-1-(7-36) amide inhibits food and water intake in rats," Am J. Physiol. 271(4 Pt 2):R848-56 (1996).

Tavares et al., "Enzymatic- and renal-dependent catabolism of the intestinotropic hormone glucagon-like peptide-2 in rats," Am J Physiol Endocrinol Metab. 278(1):E134-9 (2000).

Thorkildsen et al., "The exendin analogue ZP10 increases insulin mRNA expression in db/db mice," Nedergaard Symposium, Odense, Denmark, Jan. 24, 2002 (Poster presentation) (1 page).

Thorkildsen et al., "ZP10—A New GLP-1 agonist that increases insulin mRNA expression," Nedergaard Symposium, Odense, Denmark, Jan. 24, 2002 (abstract only) (1 page).

Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002, Poster presentation (1 page).

Thulesen et al., "Glucagon-like peptide 2 (GLP-2) accelerates the growth of colonic neoplasms in mice," Gut. 53(8):1145-50 (2004).

Tomita et al., "Pancreatic islets of obese hyperglycemic mice (ob/ob)," Pancreas. 7(3):367-375 (1992).

Torres et al., "Glucagon-like peptide-2 improves both acute and late experimental radiation enteritis in the rat," Int J Radiat Oncol Biol Phys. 69(5):1563-71 (2007).

Tourrel et al., "Glucagon-like peptide-1 and exendin-4 stimulate beta-cell neogenesis in streptozotocin-treated newborn rats resulting in persistently improved glucose homeostasis at adult age," Diabetes 50(7):1562-70 (2001).

Tourrel et al., "Persistent improvement of type 2 diabetes in the Goto-Kakizaki rat model by expansion of the beta-cell mass during the prediabetic period with glucagon-like peptide-1 or exendin-4," Diabetes. 51(5):1443-52 (2002).

Transition Therapeutics Inc., "Lilly and Transition Therapeutics announce licensing and collaboration agreement. Lilly to acquire exclusive rights to gastrin based therapies program for diabetes," <http://www.transitiontherapeutics.com/media/news.php>, retrieved May 28, 2015 (2 pages).

Transition Therapeutics Inc., "Positive preclinical data with Novo Nordisk A/S long-acting GLP-1 analog and gastrin combination presented at American Diabetes Association Meeting," <http://www.transitiontherapeutics.com/media/news.php>, retrieved on May 28, 2015 (1 page).

Translation of Office Action for Japanese Patent Application No. 2004-518465, dated Nov. 24, 2009 (6 pages).

Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).

(56) References Cited

OTHER PUBLICATIONS

Turton et al., "A role for glucagon-like peptide-1 in the central regulation of feeding," Nature 379(6560):69-72 (1996).
U.S. Appl. No. 14/095,667, filed Dec. 3, 2013 (99 pages).
U.S. Appl. No. 14/116,268, filed Nov. 7, 2013 (164 pages).
Uesaka et al., "Glucagon-like peptide isolated from the eel intestine: Effects on atrial beating," J Exp Bio. 204(Pt 17):3019-26 (2001).
Underwood et al., "Crystal structure of glucagon-like peptide-1 in complex with the extracellular domain of the glucagon-like peptide-1 receptor," J Biol Chem. 285(1):723-30 (2010).
Uttenthal et al., "Molecular forms of glucagon-like peptide-1 in human pancreas and glucagonomas," J Clin Endocrinol Metabol. 61(3):472-479 (1985).
Valverde et al., "Presence and characterization of glucagon-like peptide-1(7-36) amide receptors in solubilized membranes of rat adipose tissue," Endocrinology. 132(1):75-9 (1993).
Villa-Komaroff et al., "A bacterial clone synthesizing proinsulin," Proc Natl Acad Sci USA. 75(8):3727-31 (1978).
Wang et al., "Glucagon-like peptide-1 treatment delays the onset of diabetes in 8 week-old db/db mice," Diabetologia. 45(9):1263-73 (2002).
Wells, "Additivity of mutational effects in proteins," Biochemistry. 29(37):8509-17 (1990).
Wettergren et al., "Truncated GLP-1 (proglucagon 78-107-amide) inhibits gastric and pancreatic functions in man," Dig Dis Sci. 38(4):665-73 (1993).
White, "A review of potential cardiovascular uses of intravenous glucagon administration," J Clin Pharmacol. 39(5):442-7 (1999).
Wiberg et al., "Replication and expression in mammalian cells of transfected DNA; description of an improved erythrocyte ghost fusion technique," Nucleic Acids Res. 11(21):7287-7302 (1983).
Wodarz et al., "Specific therapy regimes could lead to long-term immunological control of HIV," Proc Natl Acad Sci U.S.A. 96(25):14464-9 (1999).
Written Opinion for Singapore Patent Application No. 2012078382, dated Feb. 17, 2015 (12 pages).
Written Opinion of the International Searching Authority from PCT/GB2006/001633, dated Oct. 24, 2006 (9 pages).
Written Opinion of the International Searching Authority from PCT/GB2007/004273, dated Apr. 14, 2008 (8 pages).
Wøjdemann et al., "Inhibition of sham feeding-stimulated human gastric acid secretion by glucagon-like peptide-2," J Clin Endocrinol Metab. 84(7):2513-7 (1999).
Xu et al., "Exendin-4 stimulates both beta-cell replication and neogenesis, resulting in increased beta-cell mass and improved glucose tolerance in diabetic rats," Diabetes. 48(12):2270-6 (1999).
Yabe et al., "Quantitative measurements of cardiac phosphorus metabolites in coronary artery disease by 31P magnetic resonance spectroscopy," Circulation. 92(1):15-23 (1995) (14 pages).
Yazbeck et al., "Growth factor based therapies and intestinal disease: is glucagon-like peptide-2 the new way forward?," Cytokine Growth Factor Rev. 20(2):175-84 (2009.
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes. 48(5):1026-34 (1999).
Young et al., "Physiological and genetic factors affecting transformation of Bacillus subtilis," J Bacteriol. 81:823-9 (1961).
Yusta et al., "Enteroendocrine localization of GLP-2 receptor expression in humans and rodents," Gastroenterology. 119(3):744-55 (2000).
Zalipsky, "Functionalized poly(ethylene glycol) for preparation of biologically relevant conjugates," Bioconjug Chem. 6(2):150-165 (1995).
Zander et al., "Additive glucose-lowering effects of glucagon-like peptide-1 and metformin in type 2 diabetes," Diabetes Care. 24(4):720-5 (2001).
Zhao et al., "Direct effects of glucagon-like peptide-1 on myocardial contractility and glucose uptake in normal and postischemic isolated rat hearts," J Pharmacol Exp Ther. 317(3):1106-13 (2006).
Zhou et al., "Glucagon-like peptide 1 and exendin-4 convert pancreatic AR42J cells into glucagon-and insulin-producing cells," Diabetes. 48(12): 2358-66 (1999).
Ørskov et al., "Glucagon-Like peptides GLP-1 and GLP-2, predicted products of the glucagon gene, are secreted separately from pig small intestine but not pancreas," Endocrinology. 119(4):1467-75 (1986).

ACYLATED GLP-1/GLP-2 DUAL AGONISTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

SEQUENCE LISTING

The instant application contains a Sequence Listing which has been submitted electronically in ASCII format and is hereby incorporated by reference in its entirety. Said ASCII copy, created on Aug. 19, 2019 is named "50412-110004_Sequence_Listing_8.19.2019_ST25" and is 262,589 bytes in size.

BACKGROUND OF THE INVENTION

Field of the Invention

The present invention relates to acylated compounds having agonist activity at the GLP-1 (glucagon-like-peptide 1) and GLP-2 (glucagon-like peptide 2) receptors. The compounds find use, inter alia, in the prophylaxis or treatment of intestinal damage and dysfunction, regulation of body weight, and prophylaxis or treatment of metabolic dysfunction.

Description of Related Art

Intestinal tissue is responsible for the production of both human glucagon-like peptide 1 (GLP-1(7-36)) and human glucagon-like peptide 2 (GLP-2 (1-33)) as they are produced by the same cells. Human GLP-2 is a 33-amino-acid peptide with the following sequence: Hy-His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp-OH (SEQ ID NO: 1). It is derived from specific posttranslational processing of proglucagon in the enteroendocrine L cells of the intestine and in specific regions of the brainstem. GLP-2 binds to a single G-protein-coupled receptor belonging to the class II glucagon secretin family. GLP-2 is co-secreted with GLP-1, oxyntomodulin and glicentin, in response to nutrient ingestion. Human GLP-1 is produced as a 30-amino acid peptide with the following sequence: Hy-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH2 (SEQ ID NO: 2).

GLP-2 has been reported to induce significant growth of the small intestinal mucosal epithelium via the stimulation of stem cell proliferation in the crypts, and by inhibition of apoptosis in the villi (Drucker et al., 1996, Proc. Natl. Acad. Sci. USA 93: 7911-7916). GLP-2 also has growth effects on the colon. Furthermore, GLP-2 inhibits gastric emptying and gastric acid secretion (Wojdemann et al., 1999, J. Clin. Endocrinol. Metab. 84: 2513-2517), enhances intestinal barrier function (Benjamin et al., 2000, Gut 47: 112-119), stimulates intestinal hexose transport via the upregulation of glucose transporters (Cheeseman, 1997, Am. J. Physiol. R1965-71), and increases intestinal blood flow (Guan et al., 2003, Gastroenterology, 125: 136-147).

GLP-1 has been described as a physiological incretin hormone and has thus been mostly reported to augment an insulin response after an oral intake of glucose or fat. It is, however, generally understood that GLP-1 lowers glucagon concentrations, has beneficial effects on inhibition of fast bowel movements (Tolessa et al., 1998, Dig. Dis. Sci. 43(10): 2284-90), and slows gastric emptying.

WO2013/164484 discloses GLP-2 analogues which comprise one or more substitutions compared to h[Gly2]GLP-2 and which may have the property of an altered GLP-1 activity, and their medical use.

WO2016/066818 describes peptides having dual agonist activity at the GLP-1 and GLP-2 receptors, and proposes medical uses thereof. However, there remains a need for further compounds which combine effective agonist activities at both receptors with acceptable levels of stability.

SUMMARY OF THE INVENTION

Broadly, the present invention relates to compounds which have agonist activity at the GLP-1 (glucagon-like peptide 1) and GLP-2 (glucagon-like peptide 2) receptors, e.g. as assessed in in vitro potency assays. Such compounds are referred to in this specification as "GLP-1/GLP-2 dual agonists," or simply "dual agonists." Thus, the compounds of the present invention have activities of both GLP-1 (7-36) and GLP-2 (1-33).

In a first aspect there is provided a GLP-1/GLP-2 dual agonist represented by the formula:

$$R^1-X^*-U-R^2$$

wherein:
$R^1$ is hydrogen (Hy), $C_{1-4}$ alkyl (e.g., methyl), acetyl, formyl, benzoyl or trifluoroacetyl;
$R^2$ is $NH_2$ or OH;
$X^*$ is a peptide of formula I:

(I)
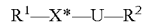
(SEQ ID NO: 3)
H-X2-EG-X5-F-X7-X8-E-X10-X11-TIL-X15-X16-X17-A-X19-X20-X21-FI-X24-WL-X27-X28-X29-KIT-X33 wherein:
X2 is Aib or G;
X5 is T or S;
X7 is T or S;
X8 is S, E or D;
X10 is L, M, V or ψ;
X11 is A, N or S;
X15 is D or E;
X16 is G, E, A or ψ;
X17 is Q, E, K, L or ψ;
X19 is A, V or S;
X20 is R, K or ψ;
X21 is D, L or E;
X24 is A, N or S;
X27 is I, Q, K, H or Y;
X28 is Q, E, A, H, Y, L, K, R or S;
X29 is H, Y, K or Q;
X33 is D or E;
U is absent or a sequence of 1-15 residues each independently selected from K, k, E, A, T, I, L and ψ;
the molecule contains one and only one Ψ, wherein Ψ is a residue of K, k, R, Orn, Dap or Dab in which the side chain is conjugated to a substituent having the formula $Z^1—$ or $Z^1—Z^2—$, wherein
$Z^1—$ is $CH_3—(CH_2)_{10-22}—(CO)—$ or $HOOC—(CH_2)_{10-22}—(CO)—$; and
$—Z^2—$ is selected from $—Z^{S1}—$, $—Z^{S1}—Z^{S2}—$, $—Z^{S2}—Z^{S1}$, $—Z^{S2}—$, $—Z^{S3}—$, $—Z^{S1}Z^{S3}—$, $—Z^{S2}Z^{S3}—$, —$Z^{S3}Z^{S1}$—, —$Z^{S3}Z^{S2}$—, —$Z^{S1}Z^{S2}Z^{S3}$—, —$Z^{S1}Z^{S3}Z^{S2}$—, —$Z^{S2}Z^{S1}Z^{S3}$—, —$Z^{S2}Z^{S3}Z^{S1}$—, —$Z^{S3}Z^{S1}Z^{S2}$—, —$Z^{S3}Z^{S2}Z^{S1}$—, —$Z^{S2}Z^{S3}Z^{S2}$— wherein $Z^{S1}$ is isoGlu, β-Ala, isoLys, or 4-aminobutanoyl;
$Z^{S2}$ is -(Peg3)$_m$- where m is 1, 2, or 3; and
—$Z^{S3}$— is a peptide sequence of 1-6 amino acid units independently selected from the group consisting of A, L, S, T, Y, Q, D, E, K, k, R, H, F and G;
and wherein at least one of X5 and X7 is T;
or a pharmaceutically acceptable salt or solvate thereof.

The various amino acid positions in peptide X* of the formulae provided here are numbered according to their linear position from N- to C-terminus in the amino acid chain.

In the present context, β-Ala and 3-Aminopropanoyl are used interchangeably.

Dual agonists having aspartic acid (Asp, D) at position 3 and glycine (Gly) in position 4 can be very potent agonists at the GLP-1 and GLP-2 receptors. However, this combination of substitutions results in compounds which are unstable and may not be suitable for long term storage in aqueous solution.

Without wishing to be bound by theory, it is believed that the Asp at position 3 may isomerise to iso-Asp via a cyclic intermediate formed between the carboxylic acid functional group of its side chain and the backbone nitrogen atom of the residue at position 4.

It has now been found that molecules having glutamic acid (Glu, E) at position 3 instead of Asp are much less susceptible to such reactions and hence may be considerably more stable when stored in aqueous solution. However, replacement of Asp with Glu at position 3 in molecules having a lipophilic substituent in the middle portion of the peptide (e.g., at or near to positions 16 and 17) tends to reduce the potency at one or both of the GLP-2 receptor and the GLP-1 receptor, even though Glu is present at position 3 of the native GLP-1 molecule. Simultaneously incorporating a Thr residue at one or both of positions 5 and 7 appears to compensate for some or all of the lost potency. It is believed that further improvements in potency are also provided by incorporation of His (H), Tyr (Y), Lys (K) or Gln (Q) at position 29 instead of the Gly (G) and Thr (T) residues present in wild type human GLP-1 and 2 respectively.

In some embodiments of formula I:
X2 is Aib or G;
X5 is T or S;
X7 is T or S;
X8 is S;
X10 is L or ψ;
X11 is A or S;
X15 is D or E;
X16 is G, E, A or ψ;
X17 is Q, E, K, L or ψ;
X19 is A or S;
X20 is R or ψ;
X21 is D, L or E;
X24 is A;
X27 is I, Q, K, or Y;
X28 is Q, E, A, H, Y, L, K, R or S;
X29 is H, Y or Q; and
X33 is D or E.

Where ψ is not at X16 or X17, it may be desirable that X16 is E and X17 is Q.

In some embodiments, X11 is A and X15 is D. In other embodiments, X11 is S and X15 is E. In further embodiments, X11 is A and X15 is E.

In some embodiments, X27 is I.

In some embodiments, X29 is H. In certain of these embodiments, X28 is A and X29 is H, or X28 is E and X29 is H.

In some embodiments, X29 is Q and optionally X27 is Q.

In some embodiments, the residues at X27-X29 have a sequence selected from:
IQH;
IEHF
IAH;
IHH;
IYH;
ILH;
IKH;
IRH;
ISH;
QQH;
YQH;
KQH;
IQQ;
IQY;
IQT; and
IAY.

In some embodiments, X* is a peptide of formula II:

(II)
(SEQ ID NO: 4)
H-X2-EG-X5-F-X7-SELATILD-X16-X17-AAR-X21-FIAWLI-X28-X29-KITD wherein:
X2 is Aib or G;
X5 is T or S;
X7 is T or S;
X16 is G or ψ;
X17 is Q, E, K, L or ψ;
X21 is D or L;
X28 is Q, E, A, H, Y, L, K, R or S;
X29 is H, Y or Q;

In some embodiments of Formula I or Formula II, X16 is ψ and X17 is Q, E, K or L. For example, X17 may be Q, or X17 may be selected from E, K and L. In other embodiments, X16 is G and X17 is ψ.

It may be desirable that X21 is D.

X28 may be selected from Q, E and A, e.g. it may be Q or E. In some residue combinations, Q may be preferred. In others, E may be preferred, including but not limited to when X16 is G and X17 is ψ.

Alternatively, X28 may be selected from A, H, Y, L, K, R and S.

X* may be a peptide of formula III:

(III)
(SEQ ID NO: 5)
H[Aib]EG-X5-F-X7-SE-X10-ATILD-X16-X17-AA-X20-X21-FIAWLI-X28-X29-KITD wherein:
X5 is T or S;
X7 is T or S;
X10 is L or ψ;
X16 is G, E, A or ψ;
X17 is Q, E, K, L or ψ;
X20 is R or ψ;

X21 is D or L;
X28 is E, A or Q;
X29 is H, Y or Q;
and at least one of X5 and X7 is T.

X* may be a peptide of formula IV:

(IV)
(SEQ ID NO: 6)
H[Aib]EG-X5-F-X7-SELATILD-X16-X17-AAR-X21-FIAWLI-
X28-X29-KITD wherein:
X5 is T or S;
X7 is T or S;
X16 is G or ψ;
X17 is E, K, L or ψ;
X21 is D or L;
X28 is E or A;
X29 is H, Y or Q;
and at least one of X5 and X7 is T.

In some embodiments of any of formulae I to IV, X16 is ψ and X17 is E, K or L.

In other embodiments of formula I to IV, X16 is G and X17 is IP.

In either case, the following combinations of residues may also be included:
X21 is D and X28 is E;
X21 is D and X28 is A;
X21 is L and X28 is E; or
X21 is L and X28 is A.

X* may be a peptide of formula V:

(V)
(SEQ ID NO: 7)
H[Aib]EG-X5-F-X7-SELATILD-Ψ-QAARDFIAWLI-X28-X29-
KITD wherein
X5 is T or S;
X7 is T or S;
X28 is Q, E, A, H, Y, L, K, R or S, e.g., Q, E, A, H, Y or L;
X29 is H, Y or Q;
and at least one of X5 and X7 is T.

In some embodiments of formula III, X28 is Q or E. In some embodiments of formula III, X28 is Q. In other embodiments, X28 is A, H, Y, L, K, R or S, e.g. A, H, Y or L.

In any of the formulae or embodiments described above, the dual agonist contains one of the following combinations of residues:
X5 is S and X7 is T;
X5 is T and X7 is S;
X5 is T and X7 is T.

It may be preferred that X5 is S and X7 is T, or X5 is T and X7 is T.

In any of the formulae or embodiments described above, it may be desirable that X29 is H.

In some embodiments, ψ is a Lys residue whose side chain is conjugated to the substituent $Z^1$— or $Z^1$—$Z^2$—.

In some embodiments, $Z^1$—, alone or in combination with —$Z^2$—, is dodecanoyl, tetradecanoyl, hexadecanoyl, octadecanoyl or eicosanoyl.

In some embodiments, $Z^1$—, alone or in combination with —$Z^2$—, is:
13-carboxytridecanoyl, i.e., HOOC—$(CH_2)_{12}$—(CO)—;
15-carboxypentadecanoyl, i.e., HOOC—$(CH_2)_{14}$—(CO)—;
17-carboxyheptadecanoyl, i.e., HOOC—$(CH_2)_{16}$—(CO)—;
19-carboxynonadecanoyl, i.e., HOOC—$(CH_2)_{18}$—(CO)—; or
21-carboxyheneicosanoyl, i.e., HOOC—$(CH_2)_{20}$—(CO)—.

In some embodiments $Z^2$ is absent.

In some embodiments, $Z^2$ comprises $Z^{S1}$ alone or in combination with $Z^{S2}$ and/or $Z^{S3}$.

In such embodiments:
—$Z^{S1}$— is isoGlu, β-Ala, isoLys, or 4-aminobutanoyl;
—$Z^{S2}$—, when present, is -(Peg3)$_m$- where m is 1, 2, or 3; and
—$Z^{S3}$— is a peptide sequence of 1-6 amino acid units independently selected from the group consisting of A, L, S, T, Y, Q, D, E, K, k, R, H, F and G, such as the peptide sequence KEK.

$Z^2$ may have the formula —$Z^{S1}$—$Z^{S3}$—$Z^{S2}$—, where $Z^{S1}$ is bonded to $Z^1$ and $Z^{S2}$ is bonded to the side chain of the amino acid component of ψ.

Thus, in some embodiments, —$Z^2$— is:
isoGlu(Peg3)$_{0-3}$;
β-Ala(Peg3)$_{0-3}$;
isoLys(Peg3)$_{0-3}$; or
4-aminobutanoyl(Peg3)$_{0-3}$.

In further embodiments, —$Z^2$— is:
isoGlu-KEK-(Peg3)$_{0-3}$.

Specific examples of the substituent $Z^1$—$Z^2$— are set out below. In some embodiments, $Z^1$—$Z^2$— is [17-carboxy-heptadecanoyl]-isoGlu. For example, ψ may be K([17-carboxy-heptadecanoyl]-isoGlu). In some embodiments, $Z^1$—$Z^2$— is:
[17-Carboxy-heptadecanoyl]-isoGlu-KEK-Peg3- (SEQ ID NO: 413);
[17-carboxy-heptadecanoyl]-isoGlu-Peg3-;
[19-Carboxy-nonadecanoyl]-isoGlu-;
[19-Carboxy-nonadecanoyl]-isoGlu-KEK-;
[19-carboxy-nonadecanoyl]-isoGlu-KEK-Peg3- (SEQ ID NO: 414);
[19-carboxy-nonadecanoyl]-isoGlu-KEK-Peg3-Peg3- (SEQ ID NO: 434);
[19-carboxy-nonadecanoyl]-isoGlu-Peg3-Peg3-;
[19-carboxy-nonadecanoyl]-isoLys-Peg3-Peg3-Peg3-;
[Hexadecanoyl]-βAla-;
[Hexadecanoyl]-isoGlu-; or
Octadecanoyl-.

For example, ψ may be:
K([17-Carboxy-heptadecanoyl]-isoGlu-KEK-Peg3);
K([17-carboxy-heptadecanoyl]-isoGlu-Peg3);
K([19-Carboxy-nonadecanoyl]-isoGlu);
K([19-Carboxy-nonadecanoyl]-isoGlu-KEK);
K([19-Carboxy-nonadecanoyl]-isoGlu-KEK-Peg3);
K([19-carboxy-nonadecanoyl]-isoGlu-KEK-Peg3-Peg3);
K([19-carboxy-nonadecanoyl]-isoGlu-Peg3-Peg3);
K([19-carboxy-nonadecanoyl]-isoLys-Peg3-Peg3-Peg3);
K([Hexadecanoyl]-βAla-;
K([Hexadecanoyl]-isoGlu); or
K(Octadecanoyl).

When present, U represents a peptide sequence of 1-15 residues each independently selected from K (i.e., L-lysine), k (i.e., D-lysine) E (Glu), A (Ala), T (Thr), I (Ile), L (Leu) and P. For example, U may be 1-10 amino acids in length, 1-7 amino acids in length, 3-7 amino acids in length, 1-6 amino acids in length, or 3-6 amino acids in length.

Typically, U includes at least one charged amino acid (K, k or E) and preferably two or more charged amino acids. In some embodiments it includes at least 2 positively charged amino acids (K or k), or at least 1 positively charged amino acid (K or k) and at least one negatively charged amino acid (E). In some embodiments, all amino acid residues of U (except for ψ, if present) are charged. For example, U may be a chain of alternately positively and negatively charged amino acids.

In certain embodiments, U comprises residues selected only from K, k, E and ψ.

In certain embodiments, U comprises residues selected only from K, k, and ψ.

When U comprises only lysine residues (whether K or k), all residues may have an L-configuration or all may have a D-configuration. Examples include $K_{1-15}$, $K_{1-10}$ and $K_{1-7}$, e.g., $K_3$, $K_4$, $K_5$, $K_6$ and $K_7$, especially $K_5$ and $K_6$. Further examples include $k_{1-15}$, $k_{1-10}$ and $k_{1-7}$, e.g. $k_3$, $k_4$, $k_5$, $k_6$ and $k_7$, especially $k_5$ and $k_6$.

Further examples of peptide sequences U include KEK (SEQ ID NO: 8), EKEKEK (SEQ ID NO: 9), EkEkEk (SEQ ID NO: 11), AKAAEK (SEQ ID NO: 12), AKEKEK (SEQ ID NO: 13) and ATILEK (SEQ ID NO: 14).

In any case, one of those residues may be exchanged for ψ. Where the sequence U contains a residue ψ, it may be desirable that the C-terminal residue of U is ψ. Thus, further examples of sequences U include $K_{1-14}$-ψ, $K_{1-9}$-ψ and $K_{1-6}$-ψ, e.g., $K_2$-ψ, $K_3$-ψ, $K_4$-ψ, $K_5$-ψ and $K_6$-ψ, especially $K_4$-ψ and $K_5$-ψ. Yet further examples include $k_{1-14}$-ψ, $k_{1-9}$-ψ, and $k_{1-6}$-ψ, e.g. $k_2$-ψ, $k_3$-ψ, $k_{1-5}$-ψ and $k_6$-ψ especially $k_4$-ψ and $k_5$-ψ. Yet further examples include KEψ (SEQ ID NO: 15), EKEKEψ (SEQ ID NO: 16), EkEkEψ (SEQ ID NO: 17), AKAAEψ (SEQ ID NO: 18), AKEKEψ (SEQ ID NO: 19), and ATILEψ (SEQ ID NO: 20).

In some embodiments, U is absent.

In some embodiments, $R^1$ is Hy and/or $R^2$ is OH.

The peptide X* or the peptide X*—U may have the sequence:

```
                                         (SEQ ID NO: 21)
H[Aib]EGTFSSELATILDΨEAARDFIAWLIEHKITD;

(SEQ ID NO: 22)
H[Aib]EGSFTSELATILDΨEAARDFIAWLIEHKITD;

(SEQ ID NO: 23)
H[Aib]EGTFTSELATILDΨEAARDFIAWLIEHKITD;

(SEQ ID NO: 24)
H[Aib]EGTFSSELATILDΨKAARDFIAWLIEHKITD;

(SEQ ID NO: 25)
H[Aib]EGSFTSELATILDΨKAARDFIAWLIEHKITD;

(SEQ ID NO: 26)
H[Aib]EGTFTSELATILDΨKAARDFIAWLIEHKITD;

(SEQ ID NO: 27)
H[Aib]EGTFSSELATILDGΨAARDFIAWLIEHKITD;

(SEQ ID NO: 28)
H[Aib]EGSFTSELATILDGΨAARDFIAWLIEHKITD;

(SEQ ID NO: 29)
H[Aib]EGTFTSELATILDGΨAARDFIAWLIEHKITD;

(SEQ ID NO: 30)
H[Aib]EGTFSSELATILDΨLAARDFIAWLIEHKITD;

(SEQ ID NO: 31)
H[Aib]EGSFTSELATILDΨLAARDFIAWLIEHKITD;

(SEQ ID NO: 32)
H[Aib]EGTFTSELATILDΨLAARDFIAWLIEHKITD;

(SEQ ID NO: 33)
H[Aib]EGTFSSELATILDΨLAARDFIAWLIAHKITD;

(SEQ ID NO: 34)
H[Aib]EGSFTSELATILDΨLAARDFIAWLIAHKITD;

(SEQ ID NO: 35)
H[Aib]EGTFTSELATILDΨLAARDFIAWLIAHKITD;

(SEQ ID NO: 36)
H[Aib]EGTFTSELATILDΨEAARLFIAWLIEHKITD;

(SEQ ID NO: 37)
H[Aib]EGTFSSELATILDΨQAARDFIAWLIQHKITD;

(SEQ ID NO: 38)
H[Aib]EGSFTSELATILDΨQAARDFIAWLIQHKITD;

(SEQ ID NO: 39)
H[Aib]EGTFTSELATILDΨQAARDFIAWLIQHKITD;

(SEQ ID NO: 40)
H[Aib]EGTFSSELATILDΨQAARDFIAWLIEHKITD;

(SEQ ID NO: 41)
H[Aib]EGSFTSELATILDΨQAARDFIAWLIAHKITD;

(SEQ ID NO: 42)
H[Aib]EGSFTSELATILDΨQAARDFIAWLIAHKITD;

(SEQ ID NO: 43)
H[Aib]EGTFTSELATILDΨQAARDFIAWLIAHKITD;

(SEQ ID NO: 44)
H[Aib]EGSFTSELATILDΨQAARDFIAWLIEHKITD;

(SEQ ID NO: 45)
H[Aib]EGTFTSELATILDΨQAARDFIAWLIEHKITD;

(SEQ ID NO: 46)
H[Aib]EGSFTSELATILDΨQAARDFIAWLIHHKITD;

(SEQ ID NO: 47)
H[Aib]EGSFTSELATILDΨQAARDFIAWLIYHKITD;

(SEQ ID NO: 48)
H[Aib]EGSFTSELATILDΨQAARDFIAWLILHKITD;

(SEQ ID NO: 49)
H[Aib]EGSFTSELATILDΨQAARDFIAWLIKHKITD;

(SEQ ID NO: 50)
H[Aib]EGSFTSELATILDΨQAARDFIAWLIRHKITD;

(SEQ ID NO: 51)
H[Aib]EGSFTSELATILDΨQAARDFIAWLISHKITD;

(SEQ ID NO: 52)
H[Aib]EGSFTSELATILDΨQAARDFIAWLQQHKITD;

(SEQ ID NO: 53)
H[Aib]EGSFTSELATILDΨQAARDFIAWLYQHKITD;

(SEQ ID NO: 54)
H[Aib]EGSFTSELATILDΨQAARDFIAWLKQHKITD;

(SEQ ID NO: 55)
H[Aib]EGSFTSELATILDΨQAARDFIAWLIQQKITD;

(SEQ ID NO: 56)
H[Aib]EGSFTSELATILDΨQAARDFIAWLIQYKITD;

(SEQ ID NO: 57)
H[Aib]EGTFSSELSTILEΨQASREFIAWLIAYKITE;

(SEQ ID NO: 58)
H[Aib]EGTFSSELATILDEQAARDFIAWLIAHKITDkkkkkΨ;

(SEQ ID NO: 59)
H[Aib]EGTFTSELATILDEQAARDFIAWLIAHKITDkkkkkΨ;

(SEQ ID NO: 60)
H[Aib]EGSFTSELATILDEQAARDFIAWLIEHKITDkkkkkΨ;
```

-continued (SEQ ID NO: 61)
H[Aib]EGSFTSEΨATILDEQAARDFIAWLIEHKITD;

(SEQ ID NO: 62)
H[Aib]EGSFTSELATILEGΨAARDFIAWLIEHKITD;

(SEQ ID NO: 63)
H[Aib]EGSFTSELATILDEQAAΨDFIAWLIEHKITD;

(SEQ ID NO: 64)
H[Aib]EGTFTSELATILDEQAAΨDFIAWLIEHKITD;

(SEQ ID NO: 65)
H[Aib]EGTFTSEψATILDEQAARDFIAWLIEHKITD;

(SEQ ID NO: 66)
H[Aib]EGSFTSELATILDAψAARDFIAWLIEHKITD;
or (SEQ ID NO: 67)
H[Aib]EGSFTSELATILDAKAAψDFIAWLIEHKITD.

The peptide X* or the peptide X*—U may have the sequence:

(SEQ ID NO: 68)
H[Aib]EGTFSSELATILD[K*]EAARDFIAWLIEHKITD;

(SEQ ID NO: 69)
H[Aib]EGSFTSELATILD[K*]EAARDFIAWLIEHKITD;

(SEQ ID NO: 70)
H[Aib]EGTFTSELATILD[K*]EAARDFIAWLIEHKITD;

(SEQ ID NO: 71)
H[Aib]EGTFSSELATILD[K*]KAARDFIAWLIEHKITD;

(SEQ ID NO: 72)
H[Aib]EGSFTSELATILD[K*]KAARDFIAWLIEHKITD;

(SEQ ID NO: 73)
H[Aib]EGTFTSELATILD[K*]KAARDFIAWLIEHKITD;

(SEQ ID NO: 74)
H[Aib]EGTFSSELATILDG[K*]AARDFIAWLIEHKITD;

(SEQ ID NO: 75)
H[Aib]EGSFTSELATILDG[K*]AARDFIAWLIEHKITD;

(SEQ ID NO: 76)
H[Aib]EGTFTSELATILDG[K*]AARDFIAWLIEHKITD;

(SEQ ID NO: 77)
H[Aib]EGTFSSELATILD[K*]LAARDFIAWLIEHKITD;

(SEQ ID NO: 78)
H[Aib]EGSFTSELATILD[K*]LAARDFIAWLIEHKITD;

(SEQ ID NO: 79)
H[Aib]EGTFTSELATILD[K*]LAARDFIAWLIEHKITD;

(SEQ ID NO: 80)
H[Aib]EGTFSSELATILD[K*]LAARDFIAWLIAHKITD;

(SEQ ID NO: 81)
H[Aib]EGSFTSELATILD[K*]LAARDFIAWLIAHKITD;

(SEQ ID NO: 82)
H[Aib]EGTFTSELATILD[K*]LAARDFIAWLIAHKITD;

(SEQ ID NO: 83)
H[Aib]EGTFTSELATILD[K*]EAARLFIAWLIEHKITD;

(SEQ ID NO: 84)
H[Aib]EGTFSSELATILD[K*]QAARDFIAWLIQHKITD;

(SEQ ID NO: 85)
H[Aib]EGSFTSELATILD[K*]QAARDFIAWLIQHKITD;

(SEQ ID NO: 86)
H[Aib]EGTFTSELATILD[K*]QAARDFIAWLIQHKITD;

(SEQ ID NO: 87)
H[Aib]EGTFSSELATILD[K*]QAARDFIAWLIEHKITD;

(SEQ ID NO: 88)
H[Aib]EGTFSSELATILD[K*]QAARDFIAWLIAHKITD;

(SEQ ID NO: 89)
H[Aib]EGSFTSELATILD[K*]QAARDFIAWLIAHKITD;

(SEQ ID NO: 90)
H[Aib]EGTFTSELATILD[K*]QAARDFIAWLIAHKITD;

(SEQ ID NO: 91)
H[Aib]EGSFTSELATILD[K*]QAARDFIAWLIEHKITD;

(SEQ ID NO: 92)
H[Aib]EGTFTSELATILD[K*]QAARDFIAWLIEHKITD;

(SEQ ID NO: 93)
H[Aib]EGSFTSELATILD[K*]QAARDFIAWLIHHKITD;

(SEQ ID NO: 94)
H[Aib]EGSFTSELATILD[K*]QAARDFIAWLIYHKITD;

(SEQ ID NO: 95)
H[Aib]EGSFTSELATILD[K*]QAARDFIAWLILHKITD;

(SEQ ID NO: 96)
H[Aib]EGSFTSELATILD[K*]QAARDFIAWLIKHKITD;

(SEQ ID NO: 97)
H[Aib]EGSFTSELATILD[K*]QAARDFIAWLIRHKITD;

(SEQ ID NO: 98)
H[Aib]EGSFTSELATILD[K*]QAARDFIAWLISHKITD;

(SEQ ID NO: 99)
H[Aib]EGSFTSELATILD[K*]QAARDFIAWLQQHKITD;

(SEQ ID NO: 100)
H[Aib]EGSFTSELATILD[K*]QAARDFIAWLYQHKITD;

(SEQ ID NO: 101)
H[Aib]EGSFTSELATILD[K*]QAARDFIAWLKQHKITD;

(SEQ ID NO: 102)
H[Aib]EGSFTSELATILD[K*]QAARDFIAWLIQQKITD;

(SEQ ID NO: 103)
H[Aib]EGSFTSELATILD[K*]QAARDFIAWLIQYKITD;

(SEQ ID NO: 104)
H[Aib]EGTFSSELSTILE[K*]QASREFIAWLIAYKITE;

(SEQ ID NO: 105)
H[Aib]EGTFSSELATILDEQAARDFIAWLIAHKITDkkkkk[K*];

(SEQ ID NO: 106)
H[Aib]EGTFTSELATILDEQAARDFIAWLIAHKITDkkkkk[K*];

(SEQ ID NO: 107)
H[Aib]EGSFTSELATILDEQAARDFIAWLIEHKITDkkkkk[K*];

(SEQ ID NO: 108)
H[Aib]EGSFTSE[K*]ATILDEQAARDFIAWLIEHKITD;

(SEQ ID NO: 109)
H[Aib]EGSFTSELATILEG[K*]AARDFIAWLIEHKITD;

-continued

H[Aib]EGSFTSELATILDEQAA[K*]DFIAWLIEHKITD;
(SEQ ID NO: 110)

H[Aib]EGTFTSELATILDEQAA[K*]DFIAWLIEHKITD;
(SEQ ID NO: 111)

H[Aib]EGTFTSE[K*]ATILDEQAARDFIAWLIEHKITD;
(SEQ ID NO: 112)

H[Aib]EGSFTSELATILDA[K*]AARDFIAWLIEHKITD;
(SEQ ID NO: 113)

or

H[Aib]EGSFTSELATILDAKAA[K*]DFIAWLIEHKITD;
(SEQ ID NO: 114)

wherein K* or k* indicates an L or D lysine residue respectively in which the side chain is conjugated to the substituent $Z^1$— or $Z^1Z^2$—.

For example, the peptide X* or the peptide X*—U may have the sequence:

H[Aib]EGTFSSELATILD[K([17-carboxy-heptadecanoyl]-isoGlu)]EAARDFIAWLIEHKITD;
(SEQ ID NO: 115)

H[Aib]EGSFTSELATILD[K([17-carboxy-heptadecanoyl]-isoGlu)]EAARDFIAWLIEHKITD;
(SEQ ID NO: 116)

H[Aib]EGTFTSELATILD[K([17-carboxy-heptadecanoyl]-isoGlu)]EAARDFIAWLIEHKITD;
(SEQ ID NO: 117)

H[Aib]EGTFSSELATILD[K([17-carboxy-heptadecanoyl]-isoGlu)]KAARDFIAWLIEHKITD;
(SEQ ID NO: 118)

H[Aib]EGSFTSELATILD[K([17-carboxy-heptadecanoyl]-isoGlu)]KAARDFIAWLIEHKITD;
(SEQ ID NO: 119)

H[Aib]EGTFTSELATILD[K([17-carboxy-heptadecanoyl]-isoGlu)]KAARDFIAWLIEHKITD;
(SEQ ID NO: 120)

H[Aib]EGTFSSELATILDG[K([17-carboxy-heptadecanoyl]-isoGlu)]AARDFIAWLIEHKITD;
(SEQ ID NO: 121)

H[Aib]EGSFTSELATILDG[K([17-carboxy-heptadecanoyl]-isoGlu)]AARDFIAWLIEHKITD;
(SEQ ID NO: 122)

H[Aib]EGTFTSELATILDG[K([17-carboxy-heptadecanoyl]-isoGlu)]AARDFIAWLIEHKITD;
(SEQ ID NO: 123)

H+Aib+EGTFSSELATILD[K([17-carboxy-heptadecanoyl]-isoGlu)]LAARDFIAWLIEHKITD;
(SEQ ID NO: 124)

H+Aib+EGSFTSELATILD[K([17-carboxy-heptadecanoyl]-isoGlu)]LAARDFIAWLIEHKITD;
(SEQ ID NO: 125)

H+Aib+EGTFTSELATILD[K([17-carboxy-heptadecanoyl]-isoGlu)]LAARDFIAWLIEHKITD;
(SEQ ID NO: 126)

H+Aib+EGTFSSELATILD[K([17-carboxy-heptadecanoyl]-isoGlu)]LAARDFIAWLIAHKITD;
(SEQ ID NO: 127)

H+Aib+EGSFTSELATILD[K([17-carboxy-heptadecanoyl]-isoGlu)]LAARDFIAWLIAHKITD;
(SEQ ID NO: 128)

H+Aib+EGTFTSELATILD[K([17-carboxy-heptadecanoyl]-isoGlu)]LAARDFIAWLIAHKITD;
(SEQ ID NO: 129)

H[Aib]EGTFTSELATILD[K([17-carboxy-heptadecanoyl]-isoGlu)]EAARLFIAWLIEHKITD;
(SEQ ID NO: 130)

H[Aib]EGTFSSELATILD[K([17-carboxy-heptadecanoyl]-isoGlu)]QAARDFIAWLIQHKITD;
(SEQ ID NO: 131)

H[Aib]EGSFTSELATILD[K([17-carboxy-heptadecanoyl]-isoGlu)]QAARDFIAWLIQHKITD;
(SEQ ID NO: 132)

H[Aib]EGTFTSELATILD[K([17-carboxy-heptadecanoyl]-isoGlu)]QAARDFIAWLIQHKITD;
(SEQ ID NO: 133)

H[Aib]EGTFSSELATILD[K([17-carboxy-heptadecanoyl]-isoGlu)]QAARDFIAWLIEHKITD;
(SEQ ID NO: 134)

H[Aib]EGTFSSELATILD[K([17-carboxy-heptadecanoyl]-isoGlu)]QAARDFIAWLIAHKITD;
(SEQ ID NO: 135)

H[Aib]EGSFTSELATILD[K([17-carboxy-heptadecanoyl]-isoGlu)]QAARDFIAWLIAHKITD;
(SEQ ID NO: 136)

(SEQ ID NO: 137)
H[Aib]EGTFTSELATILD[K([17-carboxy-heptadecanoyl]-isoGlu)]QAARDFIAWLIAHKITD;

(SEQ ID NO: 138)
H[Aib]EGSFTSELATILD[K([17-carboxy-heptadecanoyl]-isoGlu)]QAARDFIAWLIEHKITD;

(SEQ ID NO: 139)
H[Aib]EGTFTSELATILD[K([17-carboxy-heptadecanoyl]-isoGlu)]QAARDFIAWLIEHKITD;

(SEQ ID NO: 140)
H[Aib]EGSFTSELATILD[K([17-carboxy-heptadecanoyl]-isoGlu)]QAARDFIAWLIHHKITD;

(SEQ ID NO: 141)
H[Aib]EGSFTSELATILD[K([17-carboxy-heptadecanoyl]-isoGlu)]QAARDFIAWLIYHKITD;

(SEQ ID NO: 142)
H[Aib]EGSFTSELATILD[K([17-carboxy-heptadecanoyl]-isoGlu)]QAARDFIAWLILHKITD;

(SEQ ID NO: 143)
H[Aib]EGSFTSELATILD[K([17-carboxy-heptadecanoyl]-isoGlu)]QAARDFIAWLIKHKITD;

(SEQ ID NO: 144)
H[Aib]EGSFTSELATILD[K([17-carboxy-heptadecanoyl]-isoGlu)]QAARDFIAWLIRHKITD;

(SEQ ID NO: 145)
H[Aib]EGSFTSELATILD[K([17-carboxy-heptadecanoyl]-isoGlu)]QAARDFIAWLISHKITD;

(SEQ ID NO: 146)
H[Aib]EGSFTSELATILD[K([Hexadecanoyl]-βAla)]QAARDFIAWLQQHKITD;

(SEQ ID NO: 147)
H[Aib]EGSFTSELATILD[K([17-carboxy-heptadecanoyl]iso-Glu-Peg3)]QAARDFIAWLYQHKITD;

(SEQ ID NO: 148)
H[Aib]EGSFTSELATILD[K([19-carboxy-nonadecanoyl]iso-Glu-Peg3-Peg3)]QAARDFIAWLKQHKITD;

(SEQ ID NO: 149)
H[Aib]EGSFTSELATILD[K([19-carboxy-nonadecanoyl]iso-Lys-Peg3-Peg3-Peg3)]QAARDFIAWLIQQKITD;

(SEQ ID NO: 150)
H[Aib]EGSFTSELATILD[K(Octadecanoyl)]QAARDFIAWLIQYKITD;

(SEQ ID NO: 151)
H[Aib]EGTFSSELSTILE[K(Hexadecanoyl-isoGlu)]QASREFIAWLIAYKITE;

(SEQ ID NO: 152)
H[Aib]EGTFSSELATILDEQAARDFIAWLIAHKITDkkkkkk([17-carboxy-Heptadecanoyl]-isoGlu)];

(SEQ ID NO: 153)
H[Aib]EGTFTSELATILDEQAARDFIAWLIAHKITDkkkkkk([17-carboxy-Heptadecanoyl]-isoGlu)];

(SEQ ID NO: 154)
H[Aib]EGSFTSELATILDEQAARDFIAWLIEHKITDkkkkkk([17-carboxy-Heptadecanoyl]-isoGlu)];

(SEQ ID NO: 155)
H[Aib]EGTFTSELATILD[K([19-Carboxy-nonadecanoyl]-isoGlu)]QAARDFIAWLIQHKITD;

(SEQ ID NO: 156)
H[Aib]EGSFTSE[K([19-carboxy-nonadecanoyl]iso-Glu-Peg3-Peg3)]ATILDEQAARDFIAWLIEHKITD;

(SEQ ID NO: 157)
H[Aib]EGSFTSELATILD[K([19-carboxy-nonadecanoyl]iso-Glu-Peg3-Peg3)]KAARDFIAWLIEHKITD;

(SEQ ID NO: 158)
H[Aib]EGSFTSELATILEG[K([19-carboxy-nonadecanoyl]iso-Glu-Peg3-Peg3)]AARDFIAWLIEHKITD;

(SEQ ID NO: 159)
H[Aib]EGSFTSELATILDEQAA[K([19-carboxy-nonadecanoyl]iso-Glu-Peg3-Peg3)]DFIAWLIEHKITD;

(SEQ ID NO: 160)
H[Aib]EGTFTSELATILDEQAA[K([19-carboxy-nonadecanoyl]iso-Glu-Peg3-Peg3)]DFIAWLIEHKITD;

-continued (SEQ ID NO: 161)
H[Aib]EGTFSSELATILD[K([17-Carboxy-heptadecanoyl]-isoGlu-KEK-
Peg3)]QAARDFIAWLIQHKITD;

(SEQ ID NO: 162)
H[Aib]EGTFSSELATILD[K([19-Carboxy-nonadecanoyl]-isoGlu-KEK-
Peg3)]QAARDFIAWLIQHKITD;

(SEQ ID NO: 163)
H[Aib]EGTFSSELATILD[K([17-Carboxy-heptadecanoyl]-isoGlu-KEK-
Peg3)]QAARDFIAWLIEHKITD;

(SEQ ID NO: 164)
H[Aib]EGTFSSELATILD[K([19-Carboxy-nonadecanoyl]-isoGlu-KEK-
Peg3)]QAARDFIAWLIEHKITD;

(SEQ ID NO: 165)
H[Aib]EGTFTSELATILD[K([19-Carboxy-nonadecanoyl]-isoGlu-KEK)]QAARDFIAWLIQHKITD;

(SEQ ID NO: 166)
H[Aib]EGTFTSELATILD[K([19-Carboxy-nonadecanoyl]-isoGlu-KEK-
Peg3)]QAARDFIAWLIQHKITD;

(SEQ ID NO: 167)
H[Aib]EGSFTSE[K([19-Carboxy-nonadecanoyl]-isoGlu-KEK-
Peg3)]ATILDEQAARDFIAWLIEHKITD;

(SEQ ID NO: 168)
H[Aib]EGTFTSE[K([19-Carboxy-nonadecanoyl]-isoGlu-KEK-
Peg3)]ATILDEQAARDFIAWLIEHKITD;

(SEQ ID NO: 169)
H[Aib]EGSFTSE[K([19-carboxy-nonadecanoyl]iso-Glu-KEK-Peg3-
Peg3)]ATILDEQAARDFIAWLIEHKITD;

(SEQ ID NO: 170)
H[Aib]EGTFTSELATILD[K([19-Carboxy-nonadecanoyl]-isoGlu-KEK-
Peg3)]QAARDFIAWLIEHKITD;

(SEQ ID NO: 171)
H[Aib]EGSFTSELATILD[K([19-Carboxy-nonadecanoyl]-isoGlu-KEK-
Peg3)]QAARDFIAWLIEHKITD;

(SEQ ID NO: 172)
H[Aib]EGSFTSELATILD[K([19-Carboxy-nonadecanoyl]-isoGlu-KEK-
Peg3)]QAARDFIAWLIAHKITD;

(SEQ ID NO: 173)
H[Aib]EGSFTSELATILD[K([19-Carboxy-nonadecanoyl]-isoGlu-KEK-
Peg3)]KAARDFIAWLIEHKITD;

(SEQ ID NO: 174)
H[Aib]EGSFTSELATILD[K([19-carboxy-nonadecanoyl]iso-Glu-KEK-Peg3-
Peg3)]QAARDFIAWLIEHKITD;

(SEQ ID NO: 175)
H[Aib]EGSFTSELATILEG[K([19-Carboxy-nonadecanoyl]-isoGlu-KEK-
Peg3)]AARDFIAWLIEHKITD;

(SEQ ID NO: 176)
H[Aib]EGSFTSELATILDA[K([19-Carboxy-nonadecanoyl]-isoGlu-KEK-
Peg3)]AARDFIAWLIEHKITD;

(SEQ ID NO: 177)
H[Aib]EGSFTSELATILDA[K([19-carboxy-nonadecanoyl]iso-Glu-KEK-Peg3-
Peg3)]AARDFIAWLIEHKITD;

(SEQ ID NO: 178)
H[Aib]EGSFTSELATILDEQAA[K([19-Carboxy-nonadecanoyl]-isoGlu-KEK-
Peg3)]DFIAWLIEHKITD;

(SEQ ID NO: 179)
H[Aib]EGTFTSELATILDEQAA[K([19-Carboxy-nonadecanoyl]-isoGlu-KEK-
Peg3)]DFIAWLIEHKITD;

(SEQ ID NO: 180)
H[Aib]EGSFTSELATILDEQAA[K([19-carboxy-nonadecanoyl]iso-Glu-KEK-Peg3-
Peg3)]DFIAWLIEHKITD;

-continued (SEQ ID NO: 181)
H[Aib]EGTFTSELATILDEQAA[K([19-carboxy-nonadecanoyl]iso-Glu-KEK-Peg3-Peg3)]DFIAWLIEHKITD;
or (SEQ ID NO: 182)
H[Aib]EGSFTSELATILDAKAA[K([19-Carboxy-nonadecanoyl]-isoGlu-KEK-Peg3)]DFIAWLIEHKITD.

The dual agonist may be:

(Compound 1)
(SEQ ID NO: 183)
Hy-H[Aib]EGTFSSELATILD[K([17-carboxy-heptadecanoyl]-isoGlu)]EAARDFIAWLIEHKITD-OH;

(Compound 2)
(SEQ ID NO: 184)
Hy-H[Aib]EGSFTSELATILD[K([17-carboxy-heptadecanoyl]-isoGlu)]EAARDFIAWLIEHKITD-OH;

(Compound 3)
(SEQ ID NO: 185)
Hy-H[Aib]EGTFTSELATILD[K([17-carboxy-heptadecanoyl]-isoGlu)]EAARDFIAWLIEHKITD-OH;

(Compound 4)
(SEQ ID NO: 186)
Hy-H[Aib]EGTFSSELATILD[K([17-carboxy-heptadecanoyl]-isoGlu)]KAARDFIAWLIEHKITD-OH;

(Compound 5)
(SEQ ID NO: 187)
Hy-H[Aib]EGSFTSELATILD[K([17-carboxy-heptadecanoyl]-isoGlu)]KAARDFIAWLIEHKITD-OH;

(Compound 6)
(SEQ ID NO: 188)
Hy-H[Aib]EGTFTSELATILD[K([17-carboxy-heptadecanoyl]-isoGlu)]KAARDFIAWLIEHKITD-OH;

(Compound 7)
(SEQ ID NO: 189)
Hy-H[Aib]EGTFSSELATILDG[K([17-carboxy-heptadecanoyl]-isoGlu)]AARDFIAWLIEHKITD-OH;

(Compound 8)
(SEQ ID NO: 190)
Hy-H[Aib]EGSFTSELATILDG[K([17-carboxy-heptadecanoyl]-isoGlu)]AARDFIAWLIEHKITD-OH;

(Compound 9)
(SEQ ID NO: 191)
Hy-H[Aib]EGTFTSELATILDG[K([17-carboxy-heptadecanoyl]-isoGlu)]AARDFIAWLIEHKITD-OH;

(Compound 10)
(SEQ ID NO: 192)
Hy-H[Aib]EGTFSSELATILD[K([17-carboxy-heptadecanoyl]-isoGlu)]LAARDFIAWLIEHKITD-OH;

(Compound 11)
(SEQ ID NO: 193)
Hy-H[Aib]EGSFTSELATILD[K([17-carboxy-heptadecanoyl]-isoGlu)]LAARDFIAWLIEHKITD-OH;

(Compound 12)
(SEQ ID NO: 194)
Hy-H[Aib]EGTFTSELATILD[K([17-carboxy-heptadecanoyl]-isoGlu)]LAARDFIAWLIEHKITD-OH;

(Compound 13)
(SEQ ID NO: 195)
Hy-H[Aib]EGTFSSELATILD[K([17-carboxy-heptadecanoyl]-isoGlu)]LAARDFIAWLIAHKITD-OH;

-continued (Compound 14)
(SEQ ID NO: 196)
Hy-H[Aib]EGSFTSELATILD[K([17-carboxy-heptadecanoyl]-isoGlu)]LAARDFIAWLIAHKITD-OH;

(Compound 15)
(SEQ ID NO: 197)
Hy-H[Aib]EGTFTSELATILD[K([17-carboxy-heptadecanoyl]-isoGlu)]LAARDFIAWLIAHKITD-OH;

(Compound 16)
(SEQ ID NO: 198)
Hy-H[Aib]EGTFTSELATILD[K([17-carboxy-heptadecanoyl]-isoGlu)]EAARLFIAWLIEHKITD-OH;

(Compound 17)
(SEQ ID NO: 199)
Hy-H[Aib]EGTFSSELATILD[K([17-carboxy-heptadecanoyl]-isoGlu)]QAARDFIAWLIQHKITD-OH;

(Compound 18)
(SEQ ID NO: 200)
Hy-H[Aib]EGSFTSELATILD[K([17-carboxy-heptadecanoyl]-isoGlu)]QAARDFIAWLIQHKITD-OH;

(Compound 19)
(SEQ ID NO: 201)
Hy-H[Aib]EGTFTSELATILD[K([17-carboxy-heptadecanoyl]-isoGlu)]QAARDFIAWLIQHKITD-OH;

(Compound 20)
(SEQ ID NO: 202)
Hy-H[Aib]EGTFSSELATILD[K([17-carboxy-heptadecanoyl]-isoGlu)]QAARDFIAWLIEHKITD-OH;

(Compound 21)
(SEQ ID NO: 203)
Hy-H[Aib]EGTFSSELATILD[K([17-carboxy-heptadecanoyl]-isoGlu)]QAARDFIAWLIAHKITD-OH;

(Compound 22)
(SEQ ID NO: 204)
Hy-H[Aib]EGSFTSELATILD[K([17-carboxy-heptadecanoyl]-isoGlu)]QAARDFIAWLIAHKITD-OH;

(Compound 23)
(SEQ ID NO: 205)
Hy-H[Aib]EGTFTSELATILD[K([17-carboxy-heptadecanoyl]-isoGlu)]QAARDFIAWLIAHKITD-OH;

(Compound 24)
(SEQ ID NO: 206)
Hy-H[Aib]EGSFTSELATILD[K([17-carboxy-heptadecanoyl]-isoGlu)]QAARDFIAWLIEHKITD-OH;

(Compound 25)
(SEQ ID NO: 207)
Hy-H[Aib]EGTFTSELATILD[K([17-carboxy-heptadecanoyl]-isoGlu)+QAARDFIAWLIEHKITD-OH;

(Compound 26)
(SEQ ID NO: 208)
Hy-H[Aib]EGSFTSELATILD[K([17-carboxy-heptadecanoyl]-isoGlu)]QAARDFIAWLIHHKITD-OH;

(Compound 27)
(SEQ ID NO: 209)
Hy-H[Aib]EGSFTSELATILD[K([17-carboxy-heptadecanoyl]-isoGlu)]QAARDFIAWLIYHKITD-OH;

(Compound 28)
(SEQ ID NO: 210)
Hy-H[Aib]EGSFTSELATILD[K([17-carboxy-heptadecanoyl]-isoGlu)]QAARDFIAWLILHKITD-OH;

(Compound 29)
(SEQ ID NO: 211)
Hy-H[Aib]EGSFTSELATILD[K([17-carboxy-heptadecanoyl]-isoGlu)]QAARDFIAWLIKHKITD-OH;

-continued (Compound 30)
(SEQ ID NO: 212)
Hy-H[Aib]EGSFTSELATILD[K([17-carboxy-heptadecanoyl]-isoGlu)]QAARDFIAWLIRHKITD-OH;

(Compound 31)
(SEQ ID NO: 213)
Hy-H[Aib]EGSFTSELATILD[K([17-carboxy-heptadecanoyl]-isoGlu)]QAARDFIAWLISHKITD-OH;

(Compound 32)
(SEQ ID NO: 214)
Hy-H[Aib]EGSFTSELATILD[K([Hexadecanoyl]-βAla)]QAARDFIAWLQQHKITD-OH;

(Compound 33)
(SEQ ID NO: 215)
Hy-H[Aib]EGSFTSELATILD[K([17-carboxy-heptadecanoyl]iso-Glu-Peg3)]QAARDFIAWLYQHKITD-OH;

(Compound 34)
(SEQ ID NO: 216)
Hy-H[Aib]EGSFTSELATILD[K([19-carboxy-nonadecanoyl]iso-Glu-Peg3-Peg3)]QAARDFIAWLKQHKITD-OH;

(Compound 35)
(SEQ ID NO: 217)
Hy-H[Aib]EGSFTSELATILD[K([19-carboxy-nonadecanoyl]iso-Lys-Peg3-Peg3)]QAARDFIAWLIQQKITD-OH;

(Compound 36)
(SEQ ID NO: 218)
Hy-H[Aib]EGSFTSELATILD[K(Octadecanoyl)]QAARDFIAWLIQYKITD-OH;

(Compound 37)
(SEQ ID NO: 219)
Hy-H+Aib+ EGTFSSELSTILE[K(Hexadecanoyl-isoGlu)]QASREFIAWLIAYKITE-OH;

(Compound 38)
(SEQ ID NO: 220)
Hy-H[Aib]EGTFSSELATILDEQAARDFIAWLIAHKITDkkkkkk([17-carboxy-Heptadecanoyl-isoGlu)]-[NH2];

(Compound 39)
(SEQ ID NO: 221)
Hy-H[Aib]EGTFTSELATILDEQAARDFIAWLIAHKITDkkkkkk([17-carboxy-Heptadecanoyl-isoGlu)]-[NH2];

(Compound 40)
(SEQ ID NO: 222)
Hy-H[Aib]EGSFTSELATILDEQAARDFIAWLIEHKITDkkkkkk([17-carboxy-Heptadecanoyl]-isoGlu)]-[NH2];

(Compound 41)
(SEQ ID NO: 223)
Hy-H[Aib]EGTFTSELATILD[K([19-Carboxy-nonadecanoyl]-isoGlu)+QAARDFIAWLIQHKITD-OH;

(Compound 42)
(SEQ ID NO: 224)
Hy-H[Aib]EGSFTSE[K([19-carboxy-nonadecanoyl]iso-Glu-Peg3-Peg3)]ATILDEQAARDFIAWLIEHKITD-OH;

(Compound 43)
(SEQ ID NO: 225)
Hy-H[Aib]EGSFTSELATILD[K([19-carboxy-nonadecanoyl]iso-Glu-Peg3-Peg3)]KAARDFIAWLIEHKITD-OH;

(Compound 44)
(SEQ ID NO: 226)
Hy-H[Aib]EGSFTSELATILEG[K([19-carboxy-nonadecanoyl]iso-Glu-Peg3-Peg3)]AARDFIAWLIEHKITD-OH;

(Compound 45)
(SEQ ID NO: 227)
Hy-H[Aib]EGSFTSELATILDEQAA[K([19-carboxy-nonadecanoyl]iso-Glu-Peg3-Peg3)]DFIAWLIEHKITD-OH;

(Compound 46)
(SEQ ID NO: 228)
Hy-H[Aib]EGTFTSELATILDEQAA[K([19-carboxy-nonadecanoyl]iso-Glu-Peg3-Peg3)]DFIAWLIEHKITD-OH;

-continued (Compound 47)
(SEQ ID NO: 229)
Hy-H[Aib]EGTFSSELATILD[K([17-Carboxy-heptadecanoyl]-isoGlu-KEK-
Peg3)]QAARDFIAWLIQHKITD-OH;

(Compound 48)
(SEQ ID NO: 230)
Hy-H[Aib]EGTFSSELATILD[K([19-Carboxy-nonadecanoyl]-isoGlu-KEK-
Peg3)]QAARDFIAWLIQHKITD-OH;

(Compound 49)
(SEQ ID NO: 231)
Hy-H[Aib]EGTFSSELATILD[K([17-Carboxy-heptadecanoyl]-isoGlu-KEK-
Peg3)+QAARDFIAWLIEHKITD-OH;

(Compound 50)
(SEQ ID NO: 232)
Hy-H[Aib]EGTFSSELATILD[K([19-Carboxy-nonadecanoyl]-isoGlu-KEK-
Peg3)]QAARDFIAWLIEHKITD-OH;

(Compound 51)
(SEQ ID NO: 233)
Hy-H[Aib]EGTFTSELATILD[K([19-Carboxy-nonadecanoyl]-isoGlu-
KEK)]QAARDFIAWLIQHKITD-OH;

(Compound 52)
(SEQ ID NO: 234)
Hy-H[Aib]EGTFTSELATILD[K([19-Carboxy-nonadecanoyl]-isoGlu-KEK-
Peg3)]QAARDFIAWLIQHKITD-OH;

(Compound 53)
(SEQ ID NO: 235)
Hy-H[Aib]EGSFTSE[K([19-Carboxy-nonadecanoyl]-isoGlu-KEK-
Peg3)]ATILDEQAARDFIAWLIEHKITD-OH;

(Compound 54)
(SEQ ID NO: 236)
Hy-H[Aib]EGTFTSE[K([19-Carboxy-nonadecanoyl]-isoGlu-KEK-
Peg3)]ATILDEQAARDFIAWLIEHKITD-OH;

(Compound 55)
(SEQ ID NO: 237)
Hy-H[Aib]EGSFTSE[K([19-carboxy-nonadecanoyl]iso-Glu-KEK-Peg3-
Peg3)]ATILDEQAARDFIAWLIEHKITD-OH;

(Compound 56)
(SEQ ID NO: 238)
Hy-H[Aib]EGTFTSELATILD[K([19-Carboxy-nonadecanoyl]-isoGlu-KEK-
Peg3)]QAARDFIAWLIEHKITD-OH;

(Compound 57)
(SEQ ID NO: 239)
Hy-H[Aib]EGSFTSELATILD[K([19-Carboxy-nonadecanoyl]-isoGlu-KEK-
Peg3)]QAARDFIAWLIEHKITD-OH;

(Compound 58)
(SEQ ID NO: 240)
Hy-H[Aib]EGSFTSELATILD[K([19-Carboxy-nonadecanoyl]-isoGlu-KEK-
Peg3)]QAARDFIAWLIAHKITD-OH;

(Compound 59)
(SEQ ID NO: 241)
Hy-H[Aib]EGSFTSELATILD[K([19-Carboxy-nonadecanoyl]-isoGlu-KEK-
Peg3)]KAARDFIAWLIEHKITD-OH;

(Compound 60)
(SEQ ID NO: 242)
Hy-H[Aib]EGSFTSELATILD[K([19-carboxy-nonadecanoyl]iso-Glu-KEK-Peg3-
Peg3)]QAARDFIAWLIEHKITD-OH;

(Compound 61)
(SEQ ID NO: 243)
Hy-H[Aib]EGSFTSELATILEG[K([19-Carboxy-nonadecanoyl]-isoGlu-KEK-
Peg3)]AARDFIAWLIEHKITD-OH;

(Compound 62)
(SEQ ID NO: 244)
Hy-H[Aib]EGSFTSELATILDA[K([19-Carboxy-nonadecanoyl]-isoGlu-KEK-
Peg3)]AARDFIAWLIEHKITD-OH;

(Compound 63)
(SEQ ID NO: 245)
Hy-H[Aib]EGSFTSELATILDA[K([19-carboxy-nonadecanoyl]iso-Glu-KEK-Peg3-Peg3)]AARDFIAWLIEHKITD-OH;

(Compound 64)
(SEQ ID NO: 246)
Hy-H[Aib]EGSFTSELATILDEQAA[K([19-Carboxy-nonadecanoyl]-isoGlu-KEK-Peg3)]DFIAWLIEHKITD-OH;

(Compound 65)
(SEQ ID NO: 247)
Hy-H[Aib]EGTFTSELATILDEQAA[K([19-Carboxy-nonadecanoyl]-isoGlu-KEK-Peg3)]DFIAWLIEHKITD-OH;

(Compound 66)
(SEQ ID NO: 248)
Hy-H[Aib]EGSFTSELATILDEQAA[K([19-carboxy-nonadecanoyl]iso-Glu-KEK-Peg3-Peg3)]DFIAWLIEHKITD-OH;

(Compound 67)
(SEQ ID NO: 249)
Hy-H[Aib]EGTFTSELATILDEQAA[K([19-carboxy-nonadecanoyl]iso-Glu-KEK-Peg3-Peg3)]DFIAWLIEHKITD-OH;
or (Compound 68)
(SEQ ID NO: 250)
Hy-H[Aib]EGSFTSELATILDAKAA[K([19-Carboxy-nonadecanoyl]-isoGlu-KEK-Peg3)]DFIAWLIEHKITD-OH.

The dual agonist may be in the form of a pharmaceutically acceptable salt or solvate, such as a pharmaceutically acceptable acid addition salt.

The invention also provides a composition comprising a dual agonist of the invention, or a pharmaceutically acceptable salt or solvate thereof, together with a carrier, excipient or vehicle. The carrier may be a pharmaceutically acceptable carrier.

The composition may be a pharmaceutical composition. The pharmaceutical composition may be formulated as a liquid suitable for administration by injection or infusion. It may be formulated to achieve slow release of the dual agonist.

The present invention further provides a dual agonist of the invention for use in therapy. In yet another aspect there is provided a dual agonist of the present invention for use as a medicament. Also provided is a dual agonist of the invention for use in a method of medical treatment.

The invention also provides a dual agonist of the invention for use in a method of increasing intestinal mass, improving intestinal function (especially intestinal barrier function), increasing intestinal blood flow, or repairing intestinal damage or dysfunction, e.g., damage to the intestinal epithelium.

The invention also provides a dual agonist of the invention for use in a method of prophylaxis or treatment of malabsorption, ulcers (e.g., peptic ulcers, Zollinger-Ellison Syndrome, drug-induced ulcers, and ulcers related to infections or other pathogens), short-bowel syndrome, cul-de-sac syndrome, inflammatory bowel disease (e.g., Crohn's disease and ulcerative colitis), irritable bowel syndrome (IBS), pouchitis, celiac sprue (for example arising from gluten induced enteropathy or celiac disease), tropical sprue, hypogammaglobulinemic sprue, mucositis induced by chemotherapy or radiation therapy, diarrhea induced by chemotherapy or radiation therapy, low grade inflammation, metabolic endotoxemia, necrotising enterocolitis, primary biliary cirrhosis, hepatitis, fatty liver disease (including parental nutrition associated gut atrophy, PNALD (Parenteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD).

The invention also provides a dual agonist of the invention for use in a method of reducing or inhibiting weight gain, reducing gastric emptying or intestinal transit, reducing food intake, reducing appetite, or promoting weight loss.

The invention also provides a dual agonist of the invention for use in a method of prophylaxis or treatment of obesity, morbid obesity, obesity-linked gallbladder disease, obesity-induced sleep apnea, inadequate glucose control, glucose tolerance, dyslipidemia (e.g., elevated LDL levels or reduced HDL/LDL ratio), diabetes (e.g., Type 2 diabetes, gestational diabetes), pre-diabetes, metabolic syndrome or hypertension.

The invention also provides a method of increasing intestinal mass, improving intestinal function (especially intestinal barrier function), increasing intestinal blood flow, or repairing intestinal damage or dysfunction in a subject in need thereof, the method comprising administering a dual agonist of the invention to the subject.

The invention also provides a method of prophylaxis or treatment of malabsorption, ulcers (e.g., peptic ulcers, Zollinger-Ellison Syndrome, drug-induced ulcers, and ulcers related to infections or other pathogens), short-bowel syndrome, cul-de-sac syndrome, inflammatory bowel disease (Crohn's disease and ulcerative colitis), irritable bowel syndrome (IBS), pouchitis, celiac sprue (for example arising from gluten induced enteropathy or celiac disease), tropical sprue, hypogammaglobulinemic sprue, mucositis induced by chemotherapy or radiation therapy, diarrhea induced by chemotherapy or radiation therapy, low grade inflammation, metabolic endotoxemia, necrotising enterocolitis, primary biliary cirrhosis, hepatitis, fatty liver disease (including parental nutrition associated gut atrophy, PNALD (Parenteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD) in a subject in need thereof, the method comprising administering a dual agonist of the invention to the subject.

The invention also provides a method of reducing or inhibiting weight gain, reducing gastric emptying or intestinal transit, reducing food intake, reducing appetite, or promoting weight loss in a subject in need thereof, the method comprising administering a dual agonist of the invention to the subject.

The invention also provides a method of prophylaxis or treatment of obesity, morbid obesity, obesity-linked gallbladder disease, obesity-induced sleep apnea, inadequate glucose control, glucose tolerance, dyslipidemia (e.g., elevated LDL levels or reduced HDL/LDL ratio), diabetes (e.g., Type 2 diabetes, gestational diabetes), pre-diabetes, metabolic syndrome or hypertension in a subject in need thereof, the method comprising administering a dual agonist of the invention to the subject.

The invention also provides the use of a dual agonist of the invention in the preparation of a medicament for increasing intestinal mass, improving intestinal function (especially intestinal barrier function), increasing intestinal blood flow, or repairing intestinal damage or dysfunction, e.g., damage to the intestinal epithelium.

The invention also provides the use of a dual agonist of the invention in the preparation of a medicament for prophylaxis or treatment of malabsorption, ulcers (e.g., peptic ulcers, Zollinger-Ellison Syndrome, drug-induced ulcers, and ulcers related to infections or other pathogens), short-bowel syndrome, cul-de-sac syndrome, inflammatory bowel disease (Crohn's disease and ulcerative colitis), irritable bowel syndrome (IBS), pouchitis, celiac sprue (for example arising from gluten induced enteropathy or celiac disease), tropical sprue, hypogammaglobulinemic sprue, mucositis induced by chemotherapy or radiation therapy, diarrhea induced by chemotherapy or radiation therapy, low grade inflammation, metabolic endotoxemia, necrotising enterocolitis, primary biliary cirrhosis, hepatitis, fatty liver disease (including parental nutrition associated gut atrophy, PNALD (Parenteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD).

The invention also provides the use of a dual agonist of the invention in the preparation of a medicament for reducing or inhibiting weight gain, reducing gastric emptying or intestinal transit, reducing food intake, reducing appetite, or promoting weight loss.

The invention also provides the use of a dual agonist of the invention in the preparation of a medicament for prophylaxis or treatment of obesity, morbid obesity, obesity-linked gallbladder disease, obesity-induced sleep apnea, inadequate glucose control, glucose tolerance, dyslipidemia (e.g., elevated LDL levels or reduced HDL/LDL ratio), diabetes (e.g., Type 2 diabetes, gestational diabetes), pre-diabetes, metabolic syndrome or hypertension.

A further aspect provides a therapeutic kit comprising a dual agonist, or a pharmaceutically acceptable salt or solvate thereof, according to the invention.

DETAILED DESCRIPTION OF THE PREFERRED EMBODIMENT

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

All patents, published patent applications and non-patent publications referred to in this application are specifically incorporated by reference herein. In case of conflict, the present specification, including its specific definitions, will control.

Each embodiment of the invention described herein may be taken alone or in combination with one or more other embodiments of the invention.

Definitions

Unless specified otherwise, the following definitions are provided for specific terms which are used in the present written description.

Throughout this specification, the word "comprise," and grammatical variants thereof, such as "comprises" or "comprising," will be understood to imply the inclusion of a stated integer or component, or group of integers or components, but not the exclusion of any other integer or component, or group of integers or components.

The singular forms "a," "an," and "the" include the plurals unless the context clearly dictates otherwise.

The term "including" is used to mean "including but not limited to." "Including" and "including but not limited to" may be used interchangeably.

The terms "patient," "subject" and "individual" may be used interchangeably and refer to either a human or a non-human animal. These terms include mammals such as humans, primates, livestock animals (e.g., bovines and porcines), companion animals (e.g., canines and felines) and rodents (e.g., mice and rats).

The term "solvate" in the context of the present invention refers to a complex of defined stoichiometry formed between a solute (in casu, a peptide or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that activates the receptor type in question.

Throughout the present description and claims the conventional three-letter and one-letter codes for naturally occurring amino acids are used, i.e., A (Ala), G (Gly), L (Leu), I (Ile), V (Val), F (Phe), W (Trp), S (Ser), T (Thr), Y (Tyr), N (Asn), Q (Gin), D (Asp), E (Glu), K (Lys), R (Arg), H (His), M (Met), C (Cys) and P (Pro); as well as generally accepted three-letter codes for other α-amino acids, such as sarcosine (Sar), norleucine (Nle), α-aminoisobutyric acid (Aib), 2,3-diaminopropanoic acid (Dap), 2,4-diaminobutanoic acid (Dab) and 2,5-diaminopentanoic acid (ornithine; Orn). Such other α-amino acids may be shown in square brackets "[ ]" (e.g. "[Aib]") when used in a general formula or sequence in the present specification, especially when the rest of the formula or sequence is shown using the single letter code. Unless otherwise specified, amino acid residues in peptides of the invention are of the L-configuration. However, D-configuration amino acids may be incorporated. In the present context, an amino acid code written with a small letter represents the D-configuration of said amino acid, e.g., "k" represents the D-configuration of lysine (K).

Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom [i.e., R$^1$=hydrogen=Hy in the general formulas; corresponding to the presence of a free primary or secondary amino group at the N-terminus], while an "—OH" or an "—NH$_2$" moiety at the C-terminus of the sequence indicates a hydroxy group [e.g., R$^2$=OH in general formulas; corresponding to the presence of a carboxy (COON) group at the C-terminus] or an amino group [e.g., R$^2$=[NH$_2$] in the general formulas; corresponding to the presence of an amido (CONH$_2$) group at the C-terminus], respectively. In each sequence of the invention, a C-terminal "—OH" moiety may be substituted for a C-terminal "—NH$_2$" moiety, and vice-versa.

"Percent (%) amino acid sequence identity" with respect to the GLP-2 polypeptide sequences is defined as the percentage of amino acid residues in a candidate sequence that are identical to the amino acid residues in the wild-type (human) GLP-2 sequence, after aligning the sequences and introducing gaps, if necessary, to achieve the maximum percent sequence identity, and not considering any conservative substitutions as part of the sequence identity. Sequence alignment can be carried out by the skilled person using techniques well known in the art, for example using publicly available software such as BLAST, BLAST2 or Align software. For examples, see Altschul et al., Methods in Enzymology 266: 460-480 (1996) or Pearson et al., Genomics 46: 24-36, 1997.

The percentage sequence identities used herein in the context of the present invention may be determined using these programs with their default settings. More generally, the skilled worker can readily determine appropriate parameters for determining alignment, including any algorithms needed to achieve maximal alignment over the full length of the sequences being compared.

Dual Agonist Compounds

In accordance with the present invention, the dual agonist has at least one GLP-1 and at least one GLP-2 biological activity. Exemplary GLP-1 physiological activities include reducing rate of intestinal transit, reducing rate of gastric emptying, reducing appetite, food intake or body weight, and improving glucose control and glucose tolerance. Exemplary GLP-2 physiological activities include causing an increase in intestinal mass (e.g., of small intestine or colon), intestinal repair, and improving intestinal barrier function (i.e., reducing permeability of the intestine). These parameters can be assessed in in vivo assays in which the mass and the permeability of the intestine, or a portion thereof, is determined after a test animal has been treated with a dual agonist.

The dual agonists have agonist activity at the GLP-1 and GLP-2 receptors, e.g., the human GLP-1 and GLP-2 receptors. EC$_{50}$ values for in vitro receptor agonist activity may be used as a numerical measure of agonist potency at a given receptor. An EC$_{50}$ value is a measure of the concentration (e.g., mol/L) of a compound required to achieve half of that compound's maximal activity in a particular assay. A compound having a numerical EC$_{50}$ at a particular receptor which is lower than the EC$_{50}$ of a reference compound in the same assay may be considered to have higher potency at that receptor than the reference compound.

GLP-1 Activity

In some embodiments, the dual agonist has an EC$_{50}$ at the GLP-1 receptor (e.g., the human GLP-1 receptor) which is below 2.0 nM, below 1.5 nM, below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, below 0.09 nM, below 0.08 nM, below 0.07 nM, below 0.06 nM, below 0.05 nM, below 0.04 nM, e.g., when assessed using the GLP-1 receptor potency assay described in the Examples below.

In some embodiments, the dual agonist has an EC$_{50}$ at the GLP-1 receptor which is between 0.005 and 2.5 nM, between 0.01 nM and 2.5 nM, between 0.025 and 2.5 nM, between 0.005 and 2.0 nM, between 0.01 nM and 2.0 nM, between 0.025 and 2.0 nM, between 0.005 and 1.5 nM, between 0.01 nM and 1.5 nM, between 0.025 and 1.5 nM, between 0.005 and 1.0 nM, between 0.01 nM and 1.0 nM, between 0.025 and 1.0 nM, between 0.005 and 0.5 nM, between 0.01 nM and 0.5 nM, between 0.025 and 0.5 nM, between 0.005 and 0.25 nM, between 0.01 nM and 0.25 nM, between 0.025 and 0.25 nM, e.g., when assessed using the GLP-1 receptor potency assay described in the Examples below.

An alternative measure of GLP-1 agonist activity may be derived by comparing the potency of a dual agonist with the potency of a known (or reference) GLP-1 agonist when both are measured in the same assay. Thus, the relative potency at the GLP-1 receptor may be defined as:

$$[EC_{50}(\text{reference agonist})]/[EC_{50}(\text{dual agonist})].$$

Thus, a value of 1 indicates that the dual agonist and reference agonist have equal potency, a value of >1 indicates that the dual agonist has higher potency (i.e., lower EC$_{50}$) than the reference agonist, and a value of <1 indicates that the dual agonist has lower potency (i.e., higher EC$_{50}$) than the reference agonist.

The reference GLP-1 agonist may, for example, be human GLP-1(7-37), liraglutide (NN2211; VICTOZA®), or Exendin-4, but is preferably liraglutide.

Typically, the relative potency will be between 0.001 and 100, e.g., between 0.001 and 10, between 0.001 and 5, between 0.001 and 1, between 0.001 and 0.5, between 0.001 and 0.1, between 0.001 and 0.05, or between 0.001 and 0.01;

between 0.01 and 10, between 0.01 and 5, between 0.01 and 1, between 0.01 and 0.5, between 0.01 and 0.1, or between 0.01 and 0.05;

between 0.05 and 10, between 0.05 and 5, between 0.05 and 1, between 0.05 and 0.5, or between 0.05 and 0.1;

between 0.1 and 10, between 0.1 and 5, between 0.1 and 1, or between 0.1 and 0.5;

between 0.5 and 10, between 0.5 and 5, or between 0.5 and 1;

between 1 and 10, or between 1 and 5;

or between 5 and 10.

The dual agonists described in the examples below have slightly lower GLP-1 potency than liraglutide and so may, for example, have a relative potency between 0.01 and 1, between 0.01 and 0.5 or between 0.01 and 0.1.

By contrast, the dual agonists of the invention have higher potency at the GLP-1 receptor (e.g., the human GLP-1 receptor) than wild type human GLP-2 (hGLP-2 (1-33)) or [Gly2]-hGLP-2 (1-33) (i.e., human GLP-2 having glycine at position 2, also known as teduglutide). Thus, the relative potency of the dual agonists at the GLP-1 receptor compared to hGLP-2 (1-33) or teduglutide is greater than 1, typically greater than 5 or greater than 10, and may be up to 100, up to 500, or even higher.

GLP-2 Activity

In some embodiments, the dual agonist has an $EC_{50}$ at the GLP-2 receptor (e.g., the human GLP-2 receptor) which is below 2.0 nM, below 1.5 nM, below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, below 0.09 nM, below 0.08 nM, below 0.07 nM, below 0.06 nM, below 0.05 nM, below 0.04 nM, below 0.03 nM, below 0.02 nM, or below 0.01 nM, e.g., when assessed using the GLP-1 receptor potency assay described in the Examples below.

In some embodiments, the dual agonist has an $EC_{50}$ at the GLP-2 receptor which is between 0.005 and 2.0 nM, between 0.01 nM and 2.0 nM, between 0.025 and 2.0 nM, between 0.005 and 1.5 nM, between 0.01 nM and 1.5 nM, between 0.025 and 1.5 nM, between 0.005 and 1.0 nM, between 0.01 nM and 1.0 nM, between 0.025 and 1.0 nM, between 0.005 and 0.5 nM, between 0.01 nM and 0.5 nM, between 0.025 and 0.5 nM, between 0.005 and 0.25 nM, between 0.01 nM and 0.25 nM, between 0.025 and 0.25 nM, e.g., when assessed using the GLP-2 receptor potency assay described in the Examples below.

An alternative measure of GLP-2 agonist activity may be derived by comparing the potency of a dual agonist with the potency of a known (or reference) GLP-2 agonist when both are measured in the same assay. Thus, the relative potency at the GLP-2 receptor may be defined as:

[$EC_{50}$(reference agonist)]/[$EC_{50}$(dual agonist)].

Thus, a value of 1 indicates that the dual agonist and reference agonist have equal potency, a value of >1 indicates that the dual agonist has higher potency (i.e., lower $EC_{50}$) than the reference agonist, and a value of <1 indicates that the dual agonist has lower potency (i.e., higher $EC_{50}$) than the reference agonist.

The reference GLP-2 agonist may, for example, be human GLP-2(1-33) or teduglutide ([Gly2]-hGLP-2 (1-33)), but is preferably teduglutide. Typically, the relative potency will be between 0.001 and 100, e.g., between 0.001 and 10, between 0.001 and 5, between 0.001 and 1, between 0.001 and 0.5, between 0.001 and 0.1, between 0.001 and 0.05, or between 0.001 and 0.01;

between 0.01 and 10, between 0.01 and 5, between 0.01 and 1, between 0.01 and 0.5, between 0.01 and 0.1, or between 0.01 and 0.05;

between 0.05 and 10, between 0.05 and 5, between 0.05 and 1, between 0.05 and 0.5, or between 0.05 and 0.1;

between 0.1 and 10, between 0.1 and 5, between 0.1 and 1, or between 0.1 and 0.5; between 0.5 and 10, between 0.5 and 5, or between 0.5 and 1;

between 1 and 10, or between 1 and 5;

or between 5 and 10.

The dual agonists described in the examples below have slightly lower GLP-2 potency than teduglutide and so may, for example, have a relative potency between 0.01 and 1, between 0.01 and 0.5, or between 0.01 and 0.1.

By contrast, the dual agonists of the invention have higher potency at the GLP-2 receptor (e.g., the human GLP-2 receptor) than human GLP-1(7-37), liraglutide (NN2211; VICTOZA®), or Exendin-4. Thus, the relative potency of the dual agonists at the GLP-2 receptor compared to human GLP-1(7-37), liraglutide (NN2211; VICTOZA®), or Exendin-4 is greater than 1, typically greater than 5 or greater than 10, and may be up to 100, up to 500, or even higher (if the reference GLP-1 agonist even exerts detectable activity at the GLP-2 receptor).

It will be understood that the absolute potencies of the dual agonists at each receptor are much less important than the balance between the GLP-1 and GLP-2 agonist activities. Thus, it is perfectly acceptable for the absolute GLP-1 or GLP-2 potency to be lower than that of known agonists at those receptors, as long as the dual agonist compound exerts acceptable relative levels of potency at both receptors. Any apparent deficiency in absolute potency can be compensated by an increased dose if required.

Substituents

The dual agonist of the present invention contains a residue LP which comprises a residue of Lys, Arg, Orn, Dap or Dab in which the side chain is conjugated to a substituent $Z^1$— or $Z^1$—$Z^2$— wherein $Z^1$ represents a moiety $CH_3$—$(CH_2)_{10-22}$—(CO)— or HOOC—$(CH_2)_{10-22}$—(CO)— and $Z^2$ when present represents a spacer.

The spacer $Z^2$ is selected from —$Z^{S1}$—, —$Z^{S1}$—$Z^{S2}$—, —$Z^{S2}$—$Z^{S1}$—, —$Z^{S2}$—, —$Z^{S3}$—, —$Z^{S1}Z^{S3}$—, —$Z^{S2}Z^{S3}$—, —$Z^{S3}Z^{S1}$—, —$Z^{S3}Z^{S2}$—, —$Z^{S1}Z^{S2}$—, —$Z^{S1}Z^{S3}Z^{S2}$—, —$Z^{S2}Z^{S1}Z^{S3}$—, —$Z^{S2}Z^{S3}Z^{S1}$—, —$Z^{S3}Z^{S1}Z^{S2}$—, —$Z^{S3}Z^{S2}Z^{S1}$, $Z^{S2}Z^{S3}Z^{S2}$— wherein:

$Z^{S1}$ is isoGlu, β-Ala, isoLys, or 4-aminobutanoyl;

$Z^{S2}$ is -(Peg3)$_m$- where m is 1, 2, or 3; and $Z^{S3}$— is a peptide sequence of 1-6 amino acid units selected from the group consisting of A, L, S, T, Y, Q, D, E, K, k, R, H, F and G.

In some embodiments, $Z^2$ is a spacer of the formula —$Z^{S1}$—, —$Z^{S1}$—$Z^{S2}$—, —$Z^{S2}$—$Z^{S1}$, or $Z^{S2}$, where —$Z^{S1}$— is isoGlu, β-Ala, isoLys, or 4-aminobutanoyl; and —$Z^{S2}$— is -(Peg3)$_m$- where m is 1, 2, or 3.

Without wishing to be bound by theory, it is believed that the hydrocarbon chain of $Z^1$ binds albumin in the blood stream, thus shielding the dual agonists of the present invention from enzymatic degradation, which can enhance the half-life of the dual agonists.

The substituent may also modulate the potency of the dual agonists, with respect to the GLP-2 receptor and/or the GLP-1 receptor.

The substituent $Z^1$— or $Z^1$—$Z^2$— is conjugated to the functional group at the distal end of the side-chain from the alpha-carbon of the relevant amino acid residue. The normal ability of the amino acid (Lys, Arg, Orn, Dab, Dap) side-chain in question to participate in interactions mediated by that functional group (e.g. intra- and inter-molecular interactions) may therefore be reduced or completely eliminated by the presence of the substituent. Thus, the overall properties of the dual agonist may be relatively insensitive to changes in the actual amino acid conjugated to the substituent. Consequently, it is believed that any of the residues Lys, Arg, Orn, Dab, or Dap may be present at any position where ψ is permitted. However, in certain embodiments, it may be advantageous that the amino acid to which the substituent is conjugated is Lys or Orn.

The moiety $Z^1$ may be covalently bonded to the functional group in the amino acid side-chain, or alternatively may be conjugated to the amino acid side-chain functional group via a spacer $Z^2$.

The term "conjugated" is used here to describe the covalent attachment of one identifiable chemical moiety to another, and the structural relationship between such moieties. It should not be taken to imply any particular method of synthesis.

The bonds between $Z^1$, $Z^{S1}$, $Z^{S2}$, $Z^{S3}$ and the amino acid side chain to which the substituent is bound (collectively referred to herein as ψ) are peptidic. In other words, the units may be joined by amide condensation reactions.

$Z^1$ comprises a hydrocarbon chain having from 10 to 24 carbon (C) atoms, such as from 10 to 22 C atoms, e.g., from 10 to 20 C atoms. Preferably, it has at least 10 or at least 11 C atoms, and preferably it has 20 C atoms or fewer, e.g., 18 C atoms or fewer. For example, the hydrocarbon chain may contain 12, 13, 14, 15, 16, 17, 18, 19 or 20 carbon atoms. For example, it may contain 18 or 20 carbon atoms.

In some embodiments, $Z^1$ is a group selected from dodecanoyl, tetradecanoyl, hexadecanoyl, octadecanoyl and eicosanoyl, preferably hexadecanoyl, octadecanoyl or eicosanoyl, more preferably octadecanoyl or eicosanoyl.

Alternative $Z^1$ groups are derived from long-chain saturated α,ω-dicarboxylic acids of formula HOOC—$(CH_2)_{12-22}$—COOH, preferably from long-chain saturated α,ω-dicarboxylic acids having an even number of carbon atoms in the aliphatic chain. For example, $Z^1$ may be:
13-carboxytridecanoyl, i.e. HOOC—$(CH_2)_{12}$—(CO)—;
15-carboxypentadecanoyl, i.e. HOOC—$(CH_2)_{14}$—(CO)—;
17-carboxyheptadecanoyl, i.e. HOOC—$(CH_2)_{16}$—(CO)—;
19-carboxynonadecanoyl, i.e. HOOC—$(CH_2)_{18}$—(CO)—; or
21-carboxyheneicosanoyl, i.e. HOOC—$(CH_2)_{20}$—(CO)—.

As mentioned above, $Z^1$ may be conjugated to the amino acid side-chain by a spacer $Z^2$. When present, the spacer is attached to $Z^1$ and to the amino acid side-chain.

The spacer $Z^2$ has the —$Z^{S1}$—, —$Z^{S1}$—$Z^{S2}$—, —$Z^{S2}$—$Z^{S1}$—, —$Z^{S2}$—, —$Z^{S3}$—, —$Z^{S1}Z^{S3}$—, —$Z^{S2}Z^{S3}$—, —$Z^{S3}Z^{S1}$—, —$Z^3Z^{S2}$—, —$Z^{S1}Z^{S2}Z^{S3}$—, —$Z^{S1}Z^{S3}Z^{S2}$—, —$Z^{S2}Z^{S1}Z^{S3}$—, —$Z^{S2}Z^{S3}Z^{S1}$—, —$Z^{S3}Z^{S1}Z^{S2}$—, —$Z^{S3}Z^{S2}Z^{S1}$—, $Z^{S2}Z^{S3}Z^2$—; where
—$Z^{S1}$— is isoGlu, β-Ala, isoLys, or 4-aminobutanoyl;
—$Z^{S2}$— is -(Peg3)$_m$- where m is 1, 2, or 3; and
—$Z^{S3}$— is a peptide sequence of 1-6 amino acid units independently selected from the group consisting of A (Ala), L (Leu), S (Ser), T (Thr), Y (Tyr), Q (Gln), D (Asp), E (Glu), K (L-Lys), k (D-Lys), R (Arg), H (His), F (Phe) and G (Gly).

The terms "isoGlu" and "isoLys" indicate residues of amino acids which participate in bonds via their side chain carboxyl or amine functional groups. Thus, isoGlu participates in bonds via its alpha amino and side chain carboxyl group, while isoLys participates via its carboxyl and side chain amino groups. In the context of the present specification, the terms "γ-Glu" and "isoGlu" are used interchangeably.

The term Peg3 is used to refer to an 8-amino-3,6-dioxaoctanoyl group.

$Z^{S3}$ may, for example, be 3 to 6 amino acids in length, i.e., 3, 4, 5 or 6 amino acids in length.

In some embodiments, the amino acids of $Z^{S3}$ are independently selected from K, k, E, A, T, I and L, e.g., from K, k, E and A, e.g., from K, k and E.

Typically, $Z^{S3}$ includes at least one charged amino acid (K, k, R or E, e.g. K, k or E) and preferably two or more charged amino acids. In some embodiments it includes at least 2 positively charged amino acids (K, k or R, especially K or k), or at least 1 positively charged amino acid (K, k or R, especially K or k) and at least one negatively charged amino acid (E). In some embodiments, all amino acid residues of $Z^{S3}$ are charged. For example, $Z^{S3}$ may be a chain of alternately positively and negatively charged amino acids.

Examples of $Z^{S3}$ moieties include KEK (SEQ ID NO: 8), EKEKEK (SEQ ID NO: 9), kkkkkk (SEQ ID NO: 10), EkEkEk (SEQ ID NO: 11), AKAAEK (SEQ ID NO: 12), AKEKEK (SEQ ID NO: 13) and ATILEK (SEQ ID NO: 14).

Without being bound by theory, it is believed that the incorporation of $Z^{S3}$ into the linker between the fatty acid chain and the peptide backbone may increase the half-life of the dual agonist by enhancing its affinity for serum albumin.

In some embodiments, —$Z^2$— is —$Z^{S1}$— or —$Z^{S1}$—$Z^{S2}$—; in other words, —$Z^2$— is selected from:
isoGlu(Peg3)$_{0-3}$;
β-Ala(Peg3)$_{0-3}$;
isoLys(Peg3)$_{0-3}$; and
4-aminobutanoyl(Peg3)$_{0-3}$.

Thus, certain examples of substituents $Z^1$— include [Dodecanoyl], [Tetradecanoyl], [Hexadecanoyl], [Octadecanoyl], [Eicosanoyl], [13-Carboxy-tridecanoyl], [15-Carboxy-pentadecanoyl], [17-Carboxy-heptadecanoyl], [19-Carboxy-nonadecanoyl], [21-carboxy-heneicosanoyl].

More broadly, —$Z_{S2}$— may be —$Z^{S1}$—, —$Z^{S1}$—$Z^{S2}$—, —$Z^{S3}$—$Z^{S1}$—, —$Z^{S1}$—$Z^{S3}$—, —$Z^{S1}$—$Z^{S3}$—$Z^{S2}$—, —$Z^{S3}$—$Z^{S2}$—$Z^{S1}$—. Thus, —$Z^2$— may be selected from the group consisting of:
isoGlu(Peg3)$_{0-3}$;
β-Ala(Peg3)$_{0-3}$;
isoLys(Peg3)$_{0-3}$;
4-aminobutanoyl(Peg3)$_{0-3}$;
isoGlu(KEK)(Peg3)$_{0-3}$;
β-Ala(KEK)(Peg3)$_{0-3}$;
isoLys(KEK)(Peg3)$_{0-3}$;
4-aminobutanoyl(KEK)(Peg3)$_{0-3}$;
KEK(isoGlu);
KEK(β-Ala);
KEK(isoLys);
KEK(4-aminobutanoyl);
isoGlu(KEK);
β-Ala(KEK);
isoLys(KEK);
4-aminobutanoyl(KEK);
KEK(isoGlu)(Peg3)$_{0-3}$;
KEK(β-Ala)(Prg3)$_{0-3}$;
KEK(isoLys)(Peg3)$_{0-3}$; and
KEK(4-aminobutanoyl)(Peg3)$_{0-3}$;

Certain examples of substituents $Z^1$—$Z^2$— include:
[Dodecanoyl]-isoGlu, [Tetradecanoyl]-isoGlu, [Hexadecanoyl]-isoGlu, [Octadecanoyl]-isoGlu, [Eicosanoyl]-isoGlu,
[Hexadecanoyl]-βAla, [Octadecanoyl]-βAla, [Eicosanoyl]-βAla, [Tetradecanoyl]-βAla, [Dodecanoyl]-βAla,
[Dodecanoyl]isoGlu-Peg3, [Tetradecanoyl]-isoGlu-Peg3, [Hexadecanoyl]isoGlu-Peg3, [Octadecanoyl]-isoGlu-Peg3, [Eicosanoyl]-isoGlu-Peg3,
[Dodecanoyl]-βAla-Peg3, [Tetradecanoyl]-βAla-Peg3, [Hexadecanoyl]-βAla-Peg3, [Octadecanoyl]-βAla-Peg3, [Eicosanoyl]-βAla-Peg3,
[Dodecanoyl]-isoGlu-Peg3-Peg3, [Tetradecanoyl]-isoGlu-Peg3-Peg3, [Hexadecanoyl]isoGlu-Peg3-Peg3, [Octadecanoyl]-isoGlu-Peg3-Peg3, [Eicosanoyl]isoGlu-Peg3-Peg3,
[Dodecanoyl]-βAla-Peg3-Peg3, [Tetradecanoyl]-βAla-Peg3-Peg3, [Hexadecanoyl]-βAla-Peg3-Peg3, [Octadecanoyl]-βAla-Peg3-Peg3, [Eicosanoyl]-βAla-Peg3-Peg3,
[Dodecanoyl]-isoGlu-Peg3-Peg3-Peg3, [Tetradecanoyl]-isoGlu-Peg3-Peg3-Peg3, [Hexadecanoyl]-isoGlu-Peg3-Peg3-Peg3, [Octadecanoyl]isoGlu-Peg3-Peg3-Peg3, [Eicosanoyl]isoGlu-Peg3-Peg3-Peg3,
[Dodecanoyl]-βAla-Peg3-Peg3-Peg3, [Tetradecanoyl]-βAla-Peg3-Peg3-Peg3, [Hexadecanoyl]-βAla-Peg3-Peg3-Peg3, [Octadecanoyl]-βAla-Peg3-Peg3-Peg3, [Eicosanoyl]-βAla-Peg3-Peg3-Peg3,

[Dodecanoyl]-isoLys, [Tetradecanoyl]-isoLys, [Hexadecanoyl]-isoLys, [Octadecanoyl]-isoLys, [Eicosanoyl]-isoLys,
[Hexadecanoyl]-[4-aminobutanoyl], [Octadecanoyl]-[4-aminobutanoyl], [Eicosanoyl]-[4-aminobutanoyl], [Tetradecanoyl]-[4-aminobutanoyl], [Dodecanoyl]-[4-aminobutanoyl],
[Dodecanoyl]isoLys-Peg3, [Tetradecanoyl]-isoLys-Peg3, [Hexadecanoyl]-isoLys-Peg3, [Octadecanoyl]-isoLys-Peg3, [Eicosanoyl]-isoLys-Peg3,
[Dodecanoyl]-[4-aminobutanoyl]-Peg3, [Tetradecanoyl]-[4-aminobutanoyl]-Peg3, [Hexadecanoyl]-[4-aminobutanoyl]-Peg3,
[Octadecanoyl]-[4-aminobutanoyl]-Peg3, [Eicosanoyl]-[4-aminobutanoyl]-Peg3,
[Dodecanoyl]-isoLys-Peg3-Peg3, [Tetradecanoyl]-isoLys-Peg3-Peg3, [Hexadecanoyl]-isoLys-Peg3-Peg3, [Octadecanoyl]-isoLys-Peg3-Peg3, [Eicosanoyl]-isoLys-Peg3-Peg3,
[Dodecanoyl]-[4-aminobutanoyl]-Peg3-Peg3, [Tetradecanoyl]-[4-aminobutanoyl]-Peg3-Peg3, [Hexadecanoyl]-[4-aminobutanoyl]-Peg3-Peg3, [Octadecanoyl]-[4-aminobutanoyl]-Peg3-Peg3, [Eicosanoyl]-[4-aminobutanoyl]-Peg3-Peg3,
[Dodecanoyl]-isoLys-Peg3-Peg3-Peg3, [Tetradecanoyl]-isoLys-Peg3-Peg3-Peg3, [Hexadecanoyl]-isoLys-Peg3-Peg3-Peg3, [Octadecanoyl]-isoLys-Peg3-Peg3-Peg3, [Eicosanoyl]-isoLys-Peg3-Peg3-Peg3,
[Dodecanoyl]-[4-aminobutanoyl]-Peg3-Peg3-Peg3, [Tetradecanoyl]-[4-aminobutanoyl]-Peg3-Peg3-Peg3, [Hexadecanoyl]-[4-aminobutanoyl]-Peg3-Peg3-Peg3, [Octadecanoyl]-[4-aminobutanoyl]-Peg3-Peg3-Peg3, [Eicosanoyl]-[4-aminobutanoyl]-Peg3-Peg3-Peg3,
[13-carboxy-tridecanoyl]-isoGlu, [15-carboxy-Pentadecanoyl]-isoGlu, [17-carboxy-Heptadecanoyl]-isoGlu, [19-carboxy-Nonadecanoyl]-isoGlu, [21-carboxy-heneicosanoyl]-isoGlu,
[17-carboxy-Heptadecanoyl]-βAla, [19-carboxy-Nonadecanoyl]-βAla, [21-carboxy-heneicosanoyl]-βAla, [15-carboxy-Pentadecanoyl]-βAla, [13-carboxy-tridecanoyl]-βAla,
[13-carboxy-tridecanoyl]-isoGlu-Peg3, [15-carboxy-Pentadecanoyl]-isoGlu-Peg3, [17-carboxy-Heptadecanoyl]-isoGlu-Peg3, [19-carboxy-Nonadecanoyl]-isoGlu-Peg3, [21-carboxy-heneicosanoyl]-isoGlu-Peg3,
[13-carboxy-tridecanoyl]-βAla-Peg3, [15-carboxy-Pentadecanoyl]-βAla-Peg3, [17-carboxy-Heptadecanoyl]-βAla-Peg3, [19-carboxy-Nonadecanoyl]-βAla-Peg3, [21-carboxy-heneicosanoyl]-βAla-Peg3,
[13-carboxy-tridecanoyl]-isoGlu-Peg3-Peg3, [15-carboxy-Pentadecanoyl]-isoGlu-Peg3-Peg3, [17-carboxy-Heptadecanoyl]-isoGlu-Peg3-Peg3, [19-carboxy-Nonadecanoyl]-isoGlu-Peg3-Peg3, [21-carboxy-heneicosanoyl]-isoGlu-Peg3-Peg3,
[13-carboxy-tridecanoyl]-βAla-Peg3-Peg3, [15-carboxy-Pentadecanoyl]-βAla-Peg3-Peg3, [17-carboxy-Heptadecanoyl]-βAla-Peg3-Peg3, [19-carboxy-Nonadecanoyl]-βAla-Peg3-Peg3, [21-carboxy-heneicosanoyl]-βAla-Peg3-Peg3,
[13-carboxy-tridecanoyl]-isoGlu-Peg3-Peg3-Peg3, [15-carboxy-Pentadecanoyl]-isoGlu-Peg3-Peg3-Peg3, [17-carboxy-Heptadecanoyl]-isoGlu-Peg3-Peg3-Peg3, [19-carboxy-Nonadecanoyl]-isoGlu-Peg3-Peg3-Peg3, [21-carboxy-heneicosanoyl]-isoGlu-Peg3-Peg3-Peg3,
[13-carboxy-tridecanoyl]-βAla-Peg3-Peg3-Peg3, [15-carboxy-Pentadecanoyl]-βAla-Peg3-Peg3-Peg3, [17-carboxy-Heptadecanoyl]-βAla-Peg3-Peg3-Peg3, [19-carboxy-Nonadecanoyl]-βAla-Peg3-Peg3-Peg3, [21-carboxy-heneicosanoyl]-βAla-Peg3-Peg3-Peg3,
[13-carboxy-tridecanoyl]-isoLys, [15-carboxy-Pentadecanoyl]-isoLys, [17-carboxy-Heptadecanoyl]-isoLys, [19-carboxy-Nonadecanoyl]-isoLys, [21-carboxy-heneicosanoyl]-isoLys,
[17-carboxy-Heptadecanoyl]-[4-aminobutanoyl], [19-carboxy-Nonadecanoyl]-[4-aminobutanoyl], [21-carboxy-heneicosanoyl]-[4-aminobutanoyl], [15-carboxy-Pentadecanoyl]-[4-aminobutanoyl], [13-carboxy-tridecanoyl]-[4-aminobutanoyl],
[13-carboxy-tridecanoyl]-isoLys-Peg3, [15-carboxy-Pentadecanoyl]-isoLys-Peg3, [17-carboxy-Heptadecanoyl]-isoLys-Peg3, [19-carboxy-Nonadecanoyl]-isoLys-Peg3, [21-carboxy-heneicosanoyl]-isoLys-Peg3,
[13-carboxy-tridecanoyl]-[4-aminobutanoyl]-Peg3, [15-carboxy-Pentadecanoyl]-[4-aminobutanoyl]-Peg3, [17-carboxy-Heptadecanoyl]-[4-aminobutanoyl]-Peg3, [19-carboxy-Nonadecanoyl]-βAla-Peg3, [21-carboxy-heneicosanoyl]-βAla-Peg3,
[13-carboxy-tridecanoyl]-isoLys-Peg3-Peg3, [15-carboxy-Pentadecanoyl]-isoLys-Peg3-Peg3, [17-carboxy-Heptadecanoyl]-isoLys-Peg3-Peg3, [19-carboxy-Nonadecanoyl]-isoLys-Peg3-Peg3, [21-carboxy-heneicosanoyl]-isoLys-Peg3-Peg3,
[13-carboxy-tridecanoyl]-[4-aminobutanoyl]-Peg3-Peg3, [15-carboxy-Pentadecanoyl]-[4-aminobutanoyl]-Peg3-Peg3, [17-carboxy-Heptadecanoy]-[4-aminobutanoyl]-Peg3-Peg3, [19-carboxy-Nonadecanoyl]-[4-aminobutanoyl]-Peg3-Peg3, [21-carboxy-heneicosanoyl]-[4-aminobutanoyl]-Peg3-Peg3,
[13-carboxy-tridecanoyl]-isoLys-Peg3-Peg3-Peg3, [15-carboxy-Pentadecanoyl]-isoLys-Peg3-Peg3-Peg3, [17-carboxy-Heptadecanoyl]-isoLys-Peg3-Peg3-Peg3, [19-carboxy-Nonadecanoyl]-isoLys-Peg3-Peg3-Peg3, [21-carboxy-heneicosanoyl]-isoLys-Peg3-Peg3-Peg3,
[13-carboxy-tridecanoyl]-[4-aminobutanoyl]-Peg3-Peg3-Peg3, [15-carboxy-Pentadecanoyl]-[4-aminobutanoyl]-Peg3-Peg3-Peg3, [17-carboxy-Heptadecanoyl]-[4-aminobutanoyl]-Peg3-Peg3-Peg3, [19-carboxy-Nonadecanoyl]-[4-aminobutanoyl]-Peg3-Peg3-Peg3 and [21-carboxy-heneicosanoyl]-[4-aminobutanoyl]-Peg3-Peg3-Peg3.

Further examples of substituents $Z^1$—$Z^2$— include:
[Dodecanoyl]-isoLys, [Tetradecanoyl]-isoLys, [Hexadecanoyl]-isoLys, [Octadecanoyl]-isoLys, [Eicosanoyl]-isoLys,
[Hexadecanoyl]-[4-aminobutanoyl], [Octadecanoyl]-[4-aminobutanoyl], [Eicosanoyl]-[4-aminobutanoyl], [Tetradecanoyl]-[4-aminobutanoyl], [Dodecanoyl]-[4-aminobutanoyl],
[Hexadecanoyl]-KEK (SEQ ID NO: 251), [Octadecanoyl]-KEK (SEQ ID NO: 252), [Eicosanoyl]-KEK (SEQ ID NO: 253), [Tetradecanoyl]-KEK (SEQ ID NO: 254), [Dodecanoyl]-KEK (SEQ ID NO: 255),
[Dodecanoyl]-Peg3, [Tetradecanoyl]-Peg3, [Hexadecanoyl]-Peg3,
[Octadecanoyl]-Peg3, [Eicosanoyl]-Peg3,
[Dodecanoyl]-Peg3-Peg3, [Tetradecanoyl]-Peg3-Peg3, [Hexadecanoyl]-Peg3-Peg3, [Octadecanoyl]-Peg3-Peg3, [Eicosanoyl]-Peg3-Peg3,
[Dodecanoyl]-Peg3-Peg3-Peg3, [Tetradecanoyl]-Peg3-Peg3-Peg3, [Hexadecanoyl]-Peg3-Peg3-Peg3, [Octadecanoyl]-Peg3-Peg3-Peg3, [Eicosanoyl]-Peg3-Peg3-Peg3,
[Dodecanoyl]-isoLys-Peg3, [Tetradecanoyl]-isoLys-Peg3, [Hexadecanoyl]-isoLys-Peg3, [Octadecanoyl]-isoLys-Peg3, [Eicosanoyl]-isoLys-Peg3,

[Dodecanoyl]-[4-aminobutanoyl]-Peg3, [Tetradecanoyl]-[4-aminobutanoyl]-Peg3, [Hexadecanoyl]-[4-aminobutanoyl]-Peg3, [Octadecanoyl]-[4-aminobutanoyl]-Peg3, [Eicosanoyl]-[4-aminobutanoyl]-Peg3,

[Dodecanoyl]-KEK-Peg3 (SEQ ID NO: 256), [Tetradecanoyl]-KEK-Peg3 (SEQ ID NO: 257), [Hexadecanoyl]-KEK-Peg3 (SEQ ID NO: 258), [Octadecanoyl]-KEK-Peg3 (SEQ ID NO: 259), [Eicosanoyl]-KEK-Peg3 (SEQ ID NO: 260),

[Dodecanoyl]-isoLys-Peg3-Peg3, [Tetradecanoyl]-isoLys-Peg3-Peg3, [Hexadecanoyl]-isoLys-Peg3-Peg3, [Octadecanoyl]-isoLys-Peg3-Peg3, [Eicosanoyl]-isoLys-Peg3-Peg3,

[Dodecanoyl]-[4-aminobutanoyl]-Peg3-Peg3, [Tetradecanoyl]-[4-aminobutanoyl]-Peg3-Peg3, [Hexadecanoyl]-[4-aminobutanoyl]-Peg3-Peg3, [Octadecanoyl]-[4-aminobutanoyl]-Peg3-Peg3, [Eicosanoyl]-[4-aminobutanoyl]-Peg3-Peg3,

[Dodecanoyl]-KEK-Peg3-Peg3 (SEQ ID NO: 261), [Tetradecanoyl]-KEK-Peg3-Peg3 (SEQ ID NO: 262), [Hexadecanoyl]-KEK-Peg3-Peg3 (SEQ ID NO: 263), [Octadecanoyl]-KEK-Peg3-Peg3 (SEQ ID NO: 264), [Eicosanoyl]-KEK-Peg3-Peg3 (SEQ ID NO: 265),

[Dodecanoyl]-isoLys-Peg3-Peg3-Peg3, [Tetradecanoyl]-isoLys-Peg3-Peg3-Peg3, [Hexadecanoyl]-isoLys-Peg3-Peg3-Peg3, [Octadecanoyl]-isoLys-Peg3-Peg3-Peg3, [Eicosanoyl]-isoLys-Peg3-Peg3-Peg3,

[Dodecanoyl]-[4-aminobutanoyl]-Peg3-Peg3-Peg3, [Tetradecanoyl]-[4-aminobutanoyl]-Peg3-Peg3-Peg3, [Hexadecanoyl]-[4-aminobutanoyl]-Peg3-Peg3-Peg3, [Octadecanoyl]-[4-aminobutanoyl]-Peg3-Peg3-Peg3, [Eicosanoyl]-[4-aminobutanoyl]-Peg3-Peg3-Peg3,

[Dodecanoyl]-KEK-Peg3-Peg3-Peg3 (SEQ ID NO: 266), [Tetradecanoyl]-KEK-Peg3-Peg3-Peg3 (SEQ ID NO: 267), [Hexadecanoyl]-KEK-Peg3-Peg3-Peg3 (SEQ ID NO: 268), [Octadecanoyl]-KEK-Peg3-Peg3-Peg3 (SEQ ID NO: 269), [Eicosanoyl]-KEK-Peg3-Peg3-Peg3 (SEQ ID NO: 270),

[Dodecanoyl]-isoGlu-KEK-Peg3 (SEQ ID NO: 271), [Tetradecanoyl]-isoGlu-KEK-Peg3 (SEQ ID NO: 272), [Hexadecanoyl]-isoGlu-KEK-Peg3 (SEQ ID NO: 273), [Octadecanoyl]-isoGlu-KEK-Peg3 (SEQ ID NO: 274), [Eicosanoyl]-isoGlu-KEK-Peg3 (SEQ ID NO: 275),

[Dodecanoyl]-[4-aminobutanoyl]-KEK-Peg3 (SEQ ID NO: 276), [Tetradecanoyl]-[4-aminobutanoyl]-KEK-Peg3 (SEQ ID NO: 277), [Hexadecanoyl]-[4-aminobutanoyl]-KEK-Peg3 (SEQ ID NO: 278), [Octadecanoyl]-[4-aminobutanoyl]-KEK-Peg3 (SEQ ID NO: 279), [Eicosanoyl]-[4-aminobutanoyl]-KEK-Peg3 (SEQ ID NO: 280),

[Dodecanoyl]-isoLys-KEK-Peg3 (SEQ ID NO: 281), [Tetradecanoyl]-isoLys-KEK-Peg3 (SEQ ID NO: 282), [Hexadecanoyl]-isoLys-KEK-Peg3 (SEQ ID NO: 283), [Octadecanoyl]-isoLys-KEK-Peg3 (SEQ ID NO: 284), [Eicosanoyl]-isoLys-KEK-Peg3 (SEQ ID NO: 285),

[Dodecanoyl]-Ala-KEK-Peg3 (SEQ ID NO: 286), [Tetradecanoyl]-Ala-KEK-Peg3 (SEQ ID NO: 287), [Hexadecanoyl]-Ala-KEK-Peg3 (SEQ ID NO: 288), [Octadecanoyl]-Ala-KEK-Peg3 (SEQ ID NO: 289), [Eicosanoyl]-Ala-KEK-Peg3, (SEQ ID NO: 290)

[Dodecanoyl]-isoGlu-KEK-Peg3-Peg3 (SEQ ID NO: 291), [Tetradecanoyl]-isoGlu-KEK-Peg3-Peg3 (SEQ ID NO: 292), [Hexadecanoyl]-isoGlu-KEK-Peg3-Peg3 (SEQ ID NO: 293), [Octadecanoyl]-isoGlu-KEK-Peg3-Peg3 (SEQ ID NO: 294), [Eicosanoyl]-isoGlu-KEK-Peg3-Peg3 (SEQ ID NO: 295),

[Dodecanoyl]-βAla-KEK-Peg3-Peg3 (SEQ ID NO: 296), [Tetradecanoyl]-βAla-KEK-Peg3-Peg3 (SEQ ID NO: 297), [Hexadecanoyl]-βAla-KEK-Peg3-Peg3 (SEQ ID NO: 298), [Octadecanoyl]-βAla-KEK-Peg3-Peg3 (SEQ ID NO: 299), [Eicosanoyl]-βAla-KEK-Peg3-Peg3 (SEQ ID NO: 300),

[Dodecanoyl]-isoLys-KEK-Peg3-Peg3 (SEQ ID NO: 301), [Tetradecanoyl]-isoLys-KEK-Peg3-Peg3 (SEQ ID NO: 302), [Hexadecanoyl]-isoLys-KEK-Peg3-Peg3 (SEQ ID NO: 303), [Octadecanoyl]-isoLys-KEK-Peg3-Peg3 (SEQ ID NO: 304), [Eicosanoyl]-isoLys-KEK-Peg3-Peg3 (SEQ ID NO: 305),

[Dodecanoyl]-[4-aminobutanoyl]-KEK-Peg3-Peg3 (SEQ ID NO: 306), [Tetradecanoyl]-[4-aminobutanoyl]-KEK-Peg3-Peg3 (SEQ ID NO: 307), [Hexadecanoyl]-[4-aminobutanoyl]-KEK-Peg3-Peg3 (SEQ ID NO: 308), [Octadecanoyl]-[4-aminobutanoyl]-KEK-Peg3-Peg3 (SEQ ID NO: 309), [Eicosanoyl]-[4-aminobutanoyl]-KEK-Peg3-Peg3 (SEQ ID NO: 310),

[Dodecanoyl]-isoGlu-KEK-Peg3-Peg3-Peg3 (SEQ ID NO: 311), [Tetradecanoyl]-isoGlu-KEK-Peg3-Peg3-Peg3 (SEQ ID NO: 312), [Hexadecanoyl]-isoGlu-KEK-Peg3-Peg3-Peg3 (SEQ ID NO: 313),

[Octadecanoyl]-isoGlu-KEK-Peg3-Peg3-Peg3 (SEQ ID NO: 314), [Eicosanoyl]-isoGlu-KEK-Peg3-Peg3-Peg3 (SEQ ID NO: 315),

[Dodecanoyl]-βAla-KEK-Peg3-Peg3-Peg3 (SEQ ID NO: 316), [Tetradecanoyl]-βAla-KEK-Peg3-Peg3-Peg3 (SEQ ID NO: 317), [Hexadecanoyl]-βAla-KEK-Peg3-Peg3-Peg3 (SEQ ID NO: 318), [Octadecanoyl]-βAla-KEK-Peg3-Peg3-Peg3 (SEQ ID NO: 319), [Eicosanoyl]-βAla-KEK-Peg3-Peg3-Peg3 (SEQ ID NO: 320),

[Dodecanoyl]-isoLys-KEK-Peg3-Peg3-Peg3 (SEQ ID NO: 321), [Tetradecanoyl]-isoLys-KEK-Peg3-Peg3-Peg3 (SEQ ID NO: 322), [Hexadecanoyl]-isoLys-KEK-Peg3-Peg3-Peg3 (SEQ ID NO: 323),

[Octadecanoyl]-isoLys-KEK-Peg3-Peg3-Peg3 (SEQ ID NO: 324), [Eicosanoyl]-isoLys-KEK-Peg3-Peg3-Peg3 (SEQ ID NO: 325),

[Dodecanoyl]-[4-aminobutanoyl]-KEK-Peg3-Peg3-Peg3 (SEQ ID NO: 326), [Tetradecanoyl]-[4-aminobutanoyl]-KEK-Peg3-Peg3-Peg3 (SEQ ID NO: 327), [Hexadecanoyl]-[4-aminobutanoyl]-KEK-Peg3-Peg3-Peg3 (SEQ ID NO: 328), [Octadecanoyl]-[4-aminobutanoyl]-KEK-Peg3-Peg3-Peg3 (SEQ ID NO: 329), [Eicosanoyl]-[4-aminobutanoyl]-KEK-Peg3-Peg3-Peg3 (SEQ ID NO: 330),

[Dodecanoyl]-KEK-isoGlu-Peg3 (SEQ ID NO: 331), [Tetradecanoyl]-KEK-isoGlu-Peg3 (SEQ ID NO: 332), [Hexadecanoyl]-KEK-isoGlu-Peg3 (SEQ ID NO: 333), [Octadecanoyl]-KEK-isoGlu-Peg3 (SEQ ID NO: 334), [Eicosanoyl]-KEK-isoGlu-Peg3 (SEQ ID NO: 335),

[Dodecanoyl]-KEK-Ala-βPeg3 (SEQ ID NO: 336), [Tetradecanoyl]-KEK-βAla-Peg3 (SEQ ID NO: 337), [Hexadecanoyl]-KEK-βAla-Peg3 (SEQ ID NO: 338), [Octadecanoyl]-KEK-βAla-Peg3, (SEQ ID NO: 339) [Eicosanoyl]-KEK-βAla-Peg3 (SEQ ID NO: 340),

[Dodecanoyl]-KEK-[4-aminobutanoyl]-Peg3 (SEQ ID NO: 341), [Tetradecanoyl]-KEK-[4-aminobutanoyl]-Peg3 (SEQ ID NO: 342), [Hexadecanoyl]-KEK-[4-aminobutanoyl]-Peg3 (SEQ ID NO: 343), [Octadecanoyl]-KEK-[4-aminobutanoyl]-Peg3 (SEQ ID NO: 344), [Eicosanoyl]-KEK-[4-aminobutanoyl]-Peg3 (SEQ ID NO: 345),

[Dodecanoyl]-KEK-isoLys-Peg3 (SEQ ID NO: 346), [Tetradecanoyl]-KEK-isoLys-Peg3 (SEQ ID NO: 347), [Hexadecanoyl]-KEK-isoLys-Peg3 (SEQ ID NO: 348), [Octadecanoyl]-KEK-isoLys-Peg3 (SEQ ID NO: 349), [Eicosanoyl]-KEK-isoLys-Peg3 (SEQ ID NO: 350),

[Dodecanoyl]-KEK-isoGlu-Peg3-Peg3 (SEQ ID NO: 351), [Tetradecanoyl]-KEK-isoGlu-Peg3-Peg3 (SEQ ID NO: 352), [Hexadecanoyl]-KEK-isoGlu-Peg3-Peg3 (SEQ ID NO: 353), [Octadecanoyl]-KEK-isoGlu-Peg3-Peg3 (SEQ ID NO: 354), [Eicosanoyl]-KEK-isoGlu-Peg3-Peg3 (SEQ ID NO: 355),
[Dodecanoyl]-KEK-βAla-Peg3-Peg3 (SEQ ID NO: 356), [Tetradecanoyl]-KEK-βAla-Peg3-Peg3 (SEQ ID NO: 357), [Hexadecanoyl]-KEK-βAla-Peg3-Peg3 (SEQ ID NO: 358), [Octadecanoyl]-KEK-βAla-Peg3-Peg3 (SEQ ID NO: 359), [Eicosanoyl]-βAla-KEK-Peg3-Peg3 (SEQ ID NO: 360),
[Dodecanoyl]-KEK-[4-aminobutanoyl]-Peg3-Peg3 (SEQ ID NO: 361), [Tetradecanoyl]-KEK-[4-aminobutanoyl]-Peg3-Peg3 (SEQ ID NO: 362), [Hexadecanoyl]-KEK-[4-aminobutanoyl]-Peg3-Peg3 (SEQ ID NO: 363), [Octadecanoyl]-KEK-[4-aminobutanoyl]-Peg3-Peg3 (SEQ ID NO: 364), [Eicosanoyl]-KEK-[4-aminobutanoyl]-Peg3-Peg3 (SEQ ID NO: 365),
[Dodecanoyl]-KEK-isoLys-Peg3-Peg3 (SEQ ID NO: 366), [Tetradecanoyl]-KEK-isoLys-Peg3-Peg3 (SEQ ID NO: 367), [Hexadecanoyl]-KEK-isoLys-Peg3-Peg3 (SEQ ID NO: 368), [Octadecanoyl]-KEK-isoLys-Peg3-Peg3 (SEQ ID NO: 369), [Eicosanoyl]-KEK-isoLys-Peg3-Peg3 (SEQ ID NO: 370),
[Dodecanoyl]-KEK-isoGlu-Peg3-Peg3-Peg3 (SEQ ID NO: 371), [Tetradecanoyl]-KEK-isoGlu-Peg3-Peg3-Peg3 (SEQ ID NO: 372), [Hexadecanoyl]-KEK-isoGlu-Peg3-Peg3-Peg3 (SEQ ID NO: 373),
[Octadecanoyl]-KEK-isoGlu-Peg3-Peg3-Peg3 (SEQ ID NO: 374), [Eicosanoyl]-KEK-isoGlu-Peg3-Peg3-Peg3 (SEQ ID NO: 375),
[Dodecanoyl]-KEK-βAla-Peg3-Peg3-Peg3 (SEQ ID NO: 376), [Tetradecanoyl]-KEK-βAla-Peg3-Peg3-Peg3 (SEQ ID NO: 377), [Hexadecanoyl]-βAla-KEK-Peg3-Peg3-Peg3 (SEQ ID NO: 378),
[Octadecanoyl]-KEK-βAla-Peg3-Peg3-Peg3 (SEQ ID NO: 379), [Eicosanoyl]-KEK-βAla-Peg3-Peg3-Peg3 (SEQ ID NO: 380),
[Dodecanoyl]-KEK-[4-aminobutanoyl]-Peg3-Peg3-Peg3 (SEQ ID NO: 381), [Tetradecanoyl]-KEK-[4-aminobutanoyl]-Peg3-Peg3-Peg3 (SEQ ID NO: 382), [Hexadecanoyl]-KEK-[4-aminobutanoyl]-Peg3-Peg3-Peg3 (SEQ ID NO: 383), [Octadecanoyl]-KEK-[4-aminobutanoyl]-Peg3-Peg3-Peg3 (SEQ ID NO: 384), [Eicosanoyl]-KEK-[4-aminobutanoyl]-Peg3-Peg3-Peg3 (SEQ ID NO: 385),
[Dodecanoyl]-KEK-isoLys-Peg3-Peg3-Peg3 (SEQ ID NO: 386), [Tetradecanoyl]-KEK-isoLys-Peg3-Peg3-Peg3 (SEQ ID NO: 387), [Hexadecanoyl]-KEK-isoLys-Peg3-Peg3-Peg3 (SEQ ID NO: 388),
[Octadecanoyl]-KEK-isoLys-Peg3-Peg3-Peg3 (SEQ ID NO: 389), [Eicosanoyl]-KEK-isoLys-Peg3-Peg3-Peg3 (SEQ ID NO: 390),
[13-carboxy-tridecanoyl]-isoGlu, [15-carboxy-Pentadecanoyl]-isoGlu, [17-carboxy-Heptadecanoyl]-isoGlu, [19-carboxy-Nonadecanoyl]-isoGlu, [21-carboxy-hen21-carboxy-heneicosanoyl]-isoGlu,
[17-carboxy-Heptadecanoyl]-Ala, [19-carboxy-Nonadecanoyl]-Ala, [21-carboxy-heneicosanoyl]-Ala, [15-carboxy-Pentadecanoyl]-Ala, [13-carboxy-triclecanoyl]-Ala,
[13-carboxy-tridecanoyl]-isoLys, [15-carboxy-Pentadecanoyl]-isoLys, [17-carboxy-Heptadecanoyl]-isoLys, [19-carboxy-Nonadecanoyl]-isoLys, [21-carboxy-heneicosanoyl]-isoLys,
[17-carboxy-Heptadecanoyl]-[4-aminobutanoyl], [19-carboxy-Nonadecanoyl]-[4-aminobutanoyl], [21-carboxy-heneicosanoyl]-[4-aminobutanoyl], [15-carboxy-Pentadecanoyl]-[4-aminobutanoyl], [13-carboxy-triclecanoyl]-[4-aminobutanoyl],
[17-carboxy-Heptadecanoyl]-KEK (SEQ ID NO: 391), [19-carboxy-Nonadecanoyl]-KEK (SEQ ID NO: 392), [21-carboxy-heneicosanoyl]-KEK (SEQ ID NO: 393), [15-carboxy-Pentadecanoyl]-KEK (SEQ ID NO: 394), [13-carboxy-tridecanoyl]-KEK (SEQ ID NO: 395),
[13-carboxy-tridecanoyl]-Peg3, [15-carboxy-Pentadecanoyl]-Peg3, [17-carboxy-Heptadecanoyl]-Peg3, [19-carboxy-Nonadecanoyl]-Peg3, [21-carboxy-heneicosanoyl]-Peg3,
[13-carboxy-tridecanoyl]-Peg3-Peg3, [15-carboxy-Pentadecanoyl]-Peg3-Peg3, [17-carboxy-Heptadecanoyl]-Peg3-Peg3, [19-carboxy-Nonadecanoyl]-Peg3-Peg3, [21-carboxy-heneicosanoyl]-Peg3-Peg3,
[13-carboxy-tridecanoyl]-Peg3-Peg3-Peg3, [15-carboxy-Pentadecanoyl]-Peg3-Peg3-Peg3, [17-carboxy-Heptadecanoyl]-Peg3-Peg3-Peg3, [19-carboxy-Nonadecanoyl]-Peg3-Peg3-Peg3, [21-carboxy-heneicosanoyl]-Peg3-Peg3-Peg3,
[13-carboxy-tridecanoyl]-isoGlu-Peg3, [15-carboxy-Pentadecanoyl]-isoGlu-Peg3, [17-carboxy-Heptadecanoyl]-isoGlu-Peg3, [19-carboxy-Nonadecanoyl]-isoGlu-Peg3, [21-carboxy-heneicosanoyl]-isoGlu-Peg3,
[13-carboxy-tridecanoyl]-βAla-Peg3, [15-carboxy-Pentadecanoyl]-βAla-Peg3, [17-carboxy-Heptadecanoyl]-βAla-Peg3, [19-carboxy-Nonadecanoyl]-βAla-Peg3, [21-carboxy-heneicosanoyl]-βAla-Peg3,
[13-carboxy-tridecanoyl]-isoLys-Peg3, [15-carboxy-Pentadecanoyl]-isoLys-Peg3, [17-carboxy-Heptadecanoyl]-isoLys-Peg3, [19-carboxy-Nonadecanoyl]-isoLys-Peg3, [21-carboxy-heneicosanoyl]-isoLys-Peg3,
[13-carboxy-tridecanoyl]-[4-aminobutanoyl]-Peg3, [15-carboxy-Pentadecanoyl]-[4-aminobutanoyl]-Peg3, [17-carboxy-Heptadecanoyl]-[4-aminobutanoyl]-Peg3, [19-carboxy-Nonadecanoyl]-[4-aminobutanoyl]-Peg3, [21-carboxy-heneicosanoyl]-[4-aminobutanoyl]-Peg3,
[13-carboxy-tridecanoyl]-KEK-Peg3 (SEQ ID NO: 396), [15-carboxy-Pentadecanoyl]-KEK-Peg3 (SEQ ID NO: 397), [17-carboxy-Heptadecanoyl]-KEK-Peg3 (SEQ ID NO: 398), [19-carboxy-Nonadecanoyl]-KEK-Peg3 (SEQ ID NO: 399), [21-carboxy-heneicosanoyl]-KEK-Peg3 (SEQ ID NO: 400),
[13-carboxy-tridecanoyl]-isoGlu-Peg3-Peg3, [15-carboxy-Pentadecanoyl]-isoGlu-Peg3-Peg3, [17-carboxy-Heptadecanoyl]-isoGlu-Peg3-Peg3, [19-carboxy-Nonadecanoyl]-isoGlu-Peg3-Peg3, [21-carboxy-heneicosanoyl]-isoGlu-Peg3-Peg3,
[13-carboxy-tridecanoyl]-βAla-Peg3-Peg3, [15-carboxy-Pentadecanoyl]-βAla-Peg3-Peg3, [17-carboxy-Heptadecanoyl]-βAla-Peg3-Peg3, [19-carboxy-Nonadecanoyl]-βAla-Peg3-Peg3, [21-carboxy-heneicosanoyl]-βAla-Peg3-Peg3,
[13-carboxy-tridecanoyl]-isoLys-Peg3-Peg3, [15-carboxy-Pentadecanoyl]-isoLys-Peg3-Peg3, [17-carboxy-Heptadecanoyl]-isoLys-Peg3-Peg3, [19-carboxy-Nonadecanoyl]-isoLys-Peg3-Peg3, [21-carboxy-heneicosanoyl]-isoLys-Peg3-Peg3,
[13-carboxy-tridecanoyl]-[4-aminobutanoyl]-Peg3-Peg3, [15-carboxy-Pentadecanoyl]-[4-aminobutanoyl]-Peg3-Peg3, [17-carboxy-Heptadecanoyl]-[4-aminobutanoyl]-Peg3-Peg3, [19-carboxy-Nonadecanoyl]-[4-aminobutanoyl]-Peg3-Peg3, [21-carboxy-heneicosanoyl]-[4-aminobutanoyl]-Peg3-Peg3,
[13-carboxy-tridecanoyl]-KEK-Peg3-Peg3 (SEQ ID NO: 401), [15-carboxy-Pentadecanoyl]-KEK-Peg3-Peg3 (SEQ ID NO: 402), [17-carboxy-Heptadecanoyl]-KEK-Peg3-Peg3 (SEQ ID NO: 403), [19-carboxy-Nonadecanoyl]-KEK-Peg3-Peg3 (SEQ ID NO: 404), [21-carboxy-heneicosanoyl]-KEK-Peg3-Peg3 (SEQ ID NO: 405),

[13-carboxy-tridecanoyl]-isoGlu-Peg3-Peg3-Peg3, [15-carboxy-Pentadecanoyl]-isoGlu-Peg3-Peg3-Peg3, [17-carboxy-Heptadecanoyl]-isoGlu-Peg3-Peg3-Peg3, [19-carboxy-Nonadecanoyl]-isoGlu-Peg3-Peg3-Peg3, [21-carboxy-heneicosanoyl]-isoGlu-Peg3-Peg3-Peg3, [13-carboxy-tridecanoyl]-βAla-Peg3-Peg3-Peg3, [15-carboxy-Pentadecanoyl]-βAla-Peg3-Peg3-Peg3, [17-carboxy-Heptadecanoyl]-βAla-Peg3-Peg3-Peg3, [19-carboxy-Nonadecanoyl]-βAla-Peg3-Peg3-Peg3, [21-carboxy-heneicosanoyl]-βAla-Peg3-Peg3-Peg3,
[13-carboxy-tridecanoyl]-isoLys-Peg3-Peg3-Peg3, [15-carboxy-Pentadecanoyl]-isoLys-Peg3-Peg3-Peg3, [17-carboxy-Heptadecanoyl]-isoLys-Peg3-Peg3-Peg3, [19-carboxy-Nonadecanoyl]-isoLys-Peg3-Peg3-Peg3, [21-carboxy-heneicosanoyl]-isoLys-Peg3-Peg3-Peg3,
[13-carboxy-tridecanoyl]-[4-aminobutanoyl]-Peg3-Peg3-Peg3, [15-carboxy-Pentadecanoyl]-[4-aminobutanoyl]-Peg3-Peg3-Peg3, [17-carboxy-Heptadecanoyl]-[4-aminobutanoyl]-Peg3-Peg3-Peg3, [19-carboxy-Nonadecanoyl]-[4-aminobutanoyl]-Peg3-Peg3-Peg3, [21-carboxy-heneicosanoyl]-[4-aminobutanoyl]-Peg3-Peg3-Peg3,
[13-carboxy-tridecanoyl]-KEK-Peg3-Peg3-Peg3 (SEQ ID NO: 406), [15-carboxy-Pentadecanoyl]-KEK-Peg3-Peg3-Peg3 (SEQ ID NO: 407), [17-carboxy-Heptadecanoyl]-KEK-Peg3-Peg3-Peg3 (SEQ ID NO: 408), [19-carboxy-Nonadecanoyl]-KEK-Peg3-Peg3-Peg3 (SEQ ID NO: 409), [21-carboxy-heneicosanoyl]-KEK-Peg3-Peg3-Peg3 (SEQ ID NO: 410),
[13-carboxy-tridecanoyl]-isoGlu-KEK-Peg3 (SEQ ID NO: 411), [15-carboxy-Pentadecanoyl]-isoGlu-KEK-Peg3 (SEQ ID NO: 412), [17-carboxy-Heptadecanoyl]-isoGlu-KEK-Peg3 (SEQ ID NO: 413), [19-carboxy-Nonadecanoyl]-isoGlu-KEK-Peg3 (SEQ ID NO: 414), [21-carboxy-heneicosanoyl]-isoGlu-KEK-Peg3 (SEQ ID NO: 415),
[13-carboxy-tridecanoyl]-[4-aminobutanoyl]-KEK-Peg3 (SEQ ID NO: 416), [15-carboxy-Pentadecanoyl]-[4-aminobutanoyl]-KEK-Peg3 (SEQ ID NO: 417), [17-carboxy-Heptadecanoyl]-[4-aminobutanoyl]-KEK-Peg3 (SEQ ID NO: 418), [19-carboxy-Nonadecanoyl]-[4-aminobutanoyl]-KEK-Peg3 (SEQ ID NO: 419), [21-carboxy-heneicosanoyl]-[4-aminobutanoyl]-KEK-Peg3 (SEQ ID NO: 420),
[13-carboxy-tridecanoyl]-isoLys-KEK-Peg3 (SEQ ID NO: 421), [15-carboxy-Pentadecanoyl]-isoLys-KEK-Peg3 (SEQ ID NO: 422), [17-carboxy-Heptadecanoyl]-isoLys-KEK-Peg3 (SEQ ID NO: 423), [19-carboxy-Nonadecanoyl]-isoLys-KEK-Peg3 (SEQ ID NO: 424), [21-carboxy-heneicosanoyl]-isoLys-KEK-Peg3 (SEQ ID NO: 425),
[13-carboxy-tridecanoyl]-βAla-KEK-Peg3 (SEQ ID NO: 426), [15-carboxy-Pentadecanoyl]-βAla-KEK-Peg3 (SEQ ID NO: 427), [17-carboxy-Heptadecanoyl]-βAla-KEK-Peg3 (SEQ ID NO: 428), [19-carboxy-Nonadecanoyl]-βAla-KEK-Peg3 (SEQ ID NO: 429), [21-carboxy-heneicosanoyl]-βAla-KEK-Peg3 (SEQ ID NO: 430),
[13-carboxy-tridecanoyl]-isoGlu-KEK-Peg3-Peg3 (SEQ ID NO: 431), [15-carboxy-Pentadecanoyl]-isoGlu-KEK-Peg3-Peg3 (SEQ ID NO: 432), [17-carboxy-Heptadecanoyl]-isoGlu-KEK-Peg3-Peg3 (SEQ ID NO: 433), [19-carboxy-Nonadecanoyl]-isoGlu-KEK-Peg3-Peg3 (SEQ ID NO: 434), [21-carboxy-heneicosanoyl]-isoGlu-KEK-Peg3-Peg3 (SEQ ID NO: 435),
[13-carboxy-tridecanoyl]-βAla-KEK-Peg3-Peg3 (SEQ ID NO: 436), [15-carboxy-Pentadecanoyl]-βAla-KEK-Peg3-Peg3 (SEQ ID NO: 437), [17-carboxy-Heptadecanoyl]-βAla-KEK-Peg3-Peg3 (SEQ ID NO: 438), [19-carboxy-Nonadecanoyl]-βAla-KEK-Peg3-Peg3 (SEQ ID NO: 439), [21-carboxy-heneicosanoyl]-βAla-KEK-Peg3-Peg3 (SEQ ID NO: 440),

[13-carboxy-tridecanoyl]-isoLys-KEK-Peg3-Peg3 (SEQ ID NO: 441), [15-carboxy-Pentadecanoyl]-isoLys-KEK-Peg3-Peg3 (SEQ ID NO: 442), [17-carboxy-Heptadecanoyl]-isoLys-KEK-Peg3-Peg3 (SEQ ID NO: 443), [19-carboxy-Nonadecanoyl]-isoLys-KEK-Peg3-Peg3 (SEQ ID NO: 444), [21-carboxy-heneicosanoyl]-isoLys-KEK-Peg3-Peg3 (SEQ ID NO: 445),
[13-carboxy-tridecanoyl]-[4-aminobutanoyl]-KEK-Peg3-Peg3 (SEQ ID NO: 446), [15-carboxy-Pentadecanoyl]-[4-aminobutanoyl]-KEK-Peg3-Peg3 (SEQ ID NO: 447), [17-carboxy-Heptadecanoyl]-[4-aminobutanoyl]-KEK-Peg3-Peg3 (SEQ ID NO: 448), [19-carboxy-Nonadecanoyl]-[4-aminobutanoyl]-KEK-Peg3-Peg3 (SEQ ID NO: 449), [21-carboxy-heneicosanoyl]-[4-aminobutanoyl]-KEK-Peg3-Peg3 (SEQ ID NO: 450),
[13-carboxy-tridecanoyl]-isoGlu-KEK-Peg3-Peg3-Peg3 (SEQ ID NO: 451), [15-carboxy-Pentadecanoyl]-isoGlu-KEK-Peg3-Peg3-Peg3 (SEQ ID NO: 452), [17-carboxy-Heptadecanoyl]-isoGlu-KEK-Peg3-Peg3-Peg3 (SEQ ID NO: 453), [19-carboxy-Nonadecanoyl]-isoGlu-KEK-Peg3-Peg3-Peg3 (SEQ ID NO: 454), [21-carboxy-heneicosanoyl]-isoGlu-KEK-Peg3-Peg3-Peg3 (SEQ ID NO: 455),
[13-carboxy-tridecanoyl]-βAla-KEK-Peg3-Peg3-Peg3 (SEQ ID NO: 456), [15-carboxy-Pentadecanoyl]-βAla-KEK-Peg3-Peg3-Peg3 (SEQ ID NO: 457), [17-carboxy-Heptadecanoyl]-βAla-KEK-Peg3-Peg3-Peg3 (SEQ ID NO: 458), [19-carboxy-Nonadecanoyl]-βAla-KEK-Peg3-Peg3-Peg3 (SEQ ID NO: 459), [21-carboxy-heneicosanoyl]-βAla-KEK-Peg3-Peg3-Peg3 (SEQ ID NO: 460),
[13-carboxy-tridecanoyl]-isoLys-KEK-Peg3-Peg3-Peg3 (SEQ ID NO: 461), [15-carboxy-Pentadecanoyl]-isoLys-KEK-Peg3-Peg3-Peg3 (SEQ ID NO: 462), [17-carboxy-Heptadecanoyl]-isoLys-KEK-Peg3-Peg3-Peg3 (SEQ ID NO: 463), [19-carboxy-Nonadecanoyl]-isoLys-KEK-Peg3-Peg3-Peg3 (SEQ ID NO: 464), [21-carboxy-heneicosanoyl]-isoLys-KEK-Peg3-Peg3-Peg3 (SEQ ID NO: 465),
[13-carboxy-tridecanoyl]-[4-aminobutanoyl]-KEK-Peg3-Peg3-Peg3 (SEQ ID NO: 466), [15-carboxy-Pentadecanoyl]-[4-aminobutanoyl]-KEK-Peg3-Peg3-Peg3 (SEQ ID NO: 467), [17-carboxy-Heptadecanoyl]-[4-aminobutanoyl]-KEK-Peg3-Peg3-Peg3 (SEQ ID NO: 468), [19-carboxy-Nonadecanoyl]-[4-aminobutanoyl]-KEK-Peg3-Peg3-Peg3 (SEQ ID NO: 469), [21-carboxy-heneicosanoyl]-[4-aminobutanoyl]-KEK-Peg3-Peg3-Peg3 (SEQ ID NO: 470),
[13-carboxy-tridecanoyl]-KEK-isoGlu-Peg3 (SEQ ID NO: 471), [15-carboxy-Pentadecanoyl]-KEK-isoGlu-Peg3 (SEQ ID NO: 472), [17-carboxy-Heptadecanoyl]-KEK-isoGlu-Peg3 (SEQ ID NO: 473), [19-carboxy-Nonadecanoyl]-KEK-isoGlu-Peg3 (SEQ ID NO: 474), [21-carboxy-heneicosanoyl]-KEK-isoGlu-Peg3 (SEQ ID NO: 475),
[13-carboxy-tridecanoyl]-KEK-βAla-Peg3 (SEQ ID NO: 476), [15-carboxy-Pentadecanoyl]-KEK-βAla-Peg3 (SEQ ID NO: 477), [17-carboxy-Heptadecanoyl]-KEK-βAla-Peg3 (SEQ ID NO: 478), [19-carboxy-Nonadecanoyl]-KEK-βAla-Peg3 (SEQ ID NO: 479), [21-carboxy-heneicosanoyl]-KEK-βAla-Peg3 (SEQ ID NO: 480),
[13-carboxy-tridecanoyl]-KEK-[4-aminobutanoyl]-Peg3 (SEQ ID NO: 481), [15-carboxy-Pentadecanoyl]-KEK-[4-aminobutanoyl]-Peg3 (SEQ ID NO: 482), [17-carboxy-Heptadecanoyl]-KEK-[4-aminobutanoyl]-Peg3 (SEQ ID NO: 483), [19-carboxy-Nonadecanoyl]-KEK-[4-aminobutanoyl]-Peg3 (SEQ ID NO: 484), [21-carboxy-heneicosanoyl]-KEK-[4-aminobutanoyl]-Peg3 (SEQ ID NO: 485),
[13-carboxy-tridecanoyl]-KEK-isoLys-Peg3 (SEQ ID NO: 486), [15-carboxy-Pentadecanoyl]-KEK-isoLys-Peg3 (SEQ ID NO: 487), [17-carboxy-Heptadecanoyl]-KEK-isoLys-Peg3 (SEQ ID NO: 488), [19-carboxy-Nonadecanoyl]-

KEK-isoLys-Peg3 (SEQ ID NO: 489), [21-carboxy-heneicosanoyl]-KEK-isoLys-Peg3 (SEQ ID NO: 490),
[13-carboxy-tridecanoyl]-KEK-isoGlu-Peg3-Peg3 (SEQ ID NO: 491), [15-carboxy-Pentadecanoyl]-KEK-isoGlu-Peg3-Peg3 (SEQ ID NO: 492), [17-carboxy-Heptadecanoyl]-KEK-isoGlu-Peg3-Peg3 (SEQ ID NO: 493), [19-carboxy-Nonadecanoyl]-KEK-isoGlu-Peg3-Peg3 (SEQ ID NO: 494), [21-carboxy-heneicosanoyl]-KEK-isoGlu-Peg3-Peg3 (SEQ ID NO: 495),
[13-carboxy-tridecanoyl]-KEK-βAla-Peg3-Peg3 (SEQ ID NO: 496), [15-carboxy-Pentadecanoyl]-KEK-βAla-Peg3-Peg3 (SEQ ID NO: 497), [17-carboxy-Heptadecanoyl]-KEK-βAla-Peg3-Peg3 (SEQ ID NO: 498), [19-carboxy-Nonadecanoyl]-KEK-βAla-Peg3-Peg3 (SEQ ID NO: 499), [21-carboxy-heneicosanoyl]-βAla-KEK-Peg3-Peg3 (SEQ ID NO: 500),
[13-carboxy-tridecanoyl]-KEK-[4-aminobutanoyl]-Peg3-Peg3 (SEQ ID NO: 501), [15-carboxy-Pentadecanoyl]-KEK-[4-aminobutanoyl]-Peg3-Peg3 (SEQ ID NO: 502), [17-carboxy-Heptadecanoyl]-KEK-[4-aminobutanoyl]-Peg3-Peg3 (SEQ ID NO: 503), [19-carboxy-Nonadecanoyl]-KEK-[4-aminobutanoyl]-Peg3-Peg3 (SEQ ID NO: 504), [21-carboxy-heneicosanoyl]-KEK-[4-aminobutanoyl]-Peg3-Peg3 (SEQ ID NO: 505),
[13-carboxy-tridecanoyl]-KEK-isoLys-Peg3-Peg3 (SEQ ID NO: 506), [15-carboxy-Pentadecanoyl]-KEK-isoLys-Peg3-Peg3 (SEQ ID NO: 507), [17-carboxy-Heptadecanoyl]-KEK-isoLys-Peg3-Peg3 (SEQ ID NO: 508), [19-carboxy-Nonadecanoyl]-KEK-isoLys-Peg3-Peg3 (SEQ ID NO: 509), [21-carboxy-heneicosanoyl]-KEK-isoLys-Peg3-Peg3 (SEQ ID NO: 510),
[13-carboxy-tridecanoyl]-KEK-isoGlu-Peg3-Peg3-Peg3 (SEQ ID NO: 511), [15-carboxy-Pentadecanoyl]-KEK-isoGlu-Peg3-Peg3-Peg3 (SEQ ID NO: 512), [17-carboxy-Heptadecanoyl]-KEK-isoGlu-Peg3-Peg3-Peg3 (SEQ ID NO: 513), [19-carboxy-Nonadecanoyl]-KEK-isoGlu-Peg3-Peg3-Peg3 (SEQ ID NO: 514), [21-carboxy-heneicosanoyl]-KEK-isoGlu-Peg3-Peg3-Peg3 (SEQ ID NO: 515),
[13-carboxy-tridecanoyl]-KEK-βAla-Peg3-Peg3-Peg3 (SEQ ID NO: 516), [15-carboxy-Pentadecanoyl]-KEK-βAla-Peg3-Peg3-Peg3 (SEQ ID NO: 517), [17-carboxy-Heptadecanoyl]-βAla-KEK-Peg3-Peg3-Peg3 (SEQ ID NO: 518), [19-carboxy-Nonadecanoyl]-KEK-βAla-Peg3-Peg3-Peg3 (SEQ ID NO: 519), [21-carboxy-heneicosanoyl]-KEK-βAla-Peg3-Peg3-Peg3 (SEQ ID NO: 520),
[13-carboxy-tridecanoyl]-KEK-[4-aminobutanoyl]-Peg3-Peg3-Peg3 (SEQ ID NO: 521), [15-carboxy-Pentadecanoyl]-KEK-[4-aminobutanoyl]-Peg3-Peg3-Peg3 (SEQ ID NO: 522), [17-carboxy-Heptadecanoyl]-KEK-[4-aminobutanoyl]-Peg3-Peg3-Peg3 (SEQ ID NO: 523), [19-carboxy-Nonadecanoyl]-KEK-[4-aminobutanoyl]-Peg3-Peg3-Peg3 (SEQ ID NO: 524), [21-carboxy-heneicosanoyl]-KEK-[4-aminobutanoyl]-Peg3-Peg3-Peg3 (SEQ ID NO: 525),
[13-carboxy-tridecanoyl]-KEK-isoLys-Peg3-Peg3-Peg3 (SEQ ID NO: 526), [15-carboxy-Pentadecanoyl]-KEK-isoLys-Peg3-Peg3-Peg3 (SEQ ID NO: 527), [17-carboxy-Heptadecanoyl]-KEK-isoLys-Peg3-Peg3-Peg3 (SEQ ID NO: 528), [19-carboxy-Nonadecanoyl]-KEK-isoLys-Peg3-Peg3-Peg3 (SEQ ID NO: 529), [21-carboxy-heneicosanoyl]-KEK-isoLys-Peg3-Peg3-Peg3 (SEQ ID NO: 530).

Certain preferred substituents $Z^1$— and $Z^1$—$Z^2$— include:
[Hexadecanoyl], [Octadecanoyl], [17-Carboxy-heptadecanoyl], [19-Carboxy-nonadecanoyl],
[Hexadecanoyl]-isoGlu, [Octadecanoyl]-isoGlu,
[Hexadecanoyl]-βAla, [Octadecanoyl]-βAla,
[Hexadecanoyl]-isoGlu-Peg3,
[Hexadecanoyl]-βAla-Peg3,
[Hexadecanoyl]-isoGlu-Peg3-Peg3,
[Hexadecanoyl]-βAla-Peg3-Peg3,
[Hexadecanoyl]-βAla-Peg3-Peg3-Peg3,
[Hexadecanoyl]-isoLys,
[Hexadecanoyl]-[4-aminobutanoyl],
[Hexadecanoyl]-isoLys-Peg3,
[Hexadecanoyl]-[4-aminobutanoyl]-Peg3,
[Hexadecanoyl]-isoLys-Peg3-Peg3,
[Hexadecanoyl]-[4-aminobutanoyl]-Peg3-Peg3,
[Hexadecanoyl]-isoLys-Peg3-Peg3-Peg3,
[Hexadecanoyl]-[4-aminobutanoyl]-Peg3-Peg3-Peg3,
[17-carboxy-Heptadecanoyl]-isoGlu,
[19-carboxy-Nonadecanoyl]-isoGlu,
[17-carboxy-Heptadecanoyl]-βAla,
[19-carboxy-Nonadecanoyl]-βAla,
[17-carboxy-Heptadecanoyl]-isoGlu-Peg3,
[19-carboxy-Nonadecanoyl]-isoGlu-Peg3,
[17-carboxy-Heptadecanoyl]-βAla-Peg3,
[19-carboxy-Nonadecanoyl]-βAla-Peg3,
[17-carboxy-Heptadecanoyl]-isoGlu-Peg3-Peg3,
[19-carboxy-Nonadecanoyl]-isoGlu-Peg3-Peg3,
[17-carboxy-Heptadecanoyl]-βAla-Peg3-Peg3,
[19-carboxy-Nonadecanoyl]-βAla-Peg3-Peg3,
[17-carboxy-Heptadecanoyl]-isoGlu-Peg3-Peg3-Peg3,
[19-carboxy-Nonadecanoyl]-isoGlu-Peg3-Peg3-Peg3,
[17-carboxy-Heptadecanoyl]-βAla-Peg3-Peg3-Peg3,
[19-carboxy-Nonadecanoyl]-βAla-Peg3-Peg3-Peg3,
[17-carboxy-Heptadecanoyl]-isoLys,
[19-carboxy-Nonadecanoyl]-isoLys,
[17-carboxy-Heptadecanoyl]-[4-aminobutanoyl],
[19-carboxy-Nonadecanoyl]-[4-aminobutanoyl],
[17-carboxy-Heptadecanoyl]-isoLys-Peg3,
[19-carboxy-Nonadecanoyl]-isoLys-Peg3,
[17-carboxy-Heptadecanoyl]-[4-aminobutanoyl]-Peg3,
[19-carboxy-Nonadecanoyl]-[4-aminobutanoyl]-Peg3,
[17-carboxy-Heptadecanoyl]-isoLys-Peg3-Peg3,
[19-carboxy-Nonadecanoyl]-isoLys-Peg3-Peg3,
[17-carboxy-Heptadecanoyl]-[4-aminobutanoyl]-Peg3-Peg3,
[19-carboxy-Nonadecanoyl]-[4-aminobutanoyl]-Peg3-Peg3,
[17-carboxy-Heptadecanoyl]-isoLys-Peg3-Peg3-Peg3,
[19-carboxy-Nonadecanoyl]-isoLys-Peg3-Peg3-Peg3,
[17-carboxy-Heptadecanoyl]-[4-aminobutanoyl]-Peg3-Peg3-Peg3,
[19-carboxy-Nonadecanoyl]-[4-aminobutanoyl]-Peg3-Peg3-Peg3.

More preferred substituents $Z^1$—$Z^2$— include:
[Hexadecanoyl]-isoGlu,
[Hexadecanoyl]-βAla,
[Hexadecanoyl]-isoGlu-Peg3,
[Hexadecanoyl]-βAla-Peg3,
[Hexadecanoyl]-isoGlu-Peg3-Peg3,
[Hexadecanoyl]-isoLys,
[Hexadecanoyl]-isoLys-Peg3,
[Hexadecanoyl]-isoLys-Peg3,
[17-carboxy-Heptadecanoyl]-isoGlu,
[19-carboxy-Nonadecanoyl]-isoGlu,
[17-carboxy-Heptadecanoyl]-isoGlu-Peg3,
[19-carboxy-Nonadecanoyl]-isoGlu-Peg3,
[17-carboxy-Heptadecanoyl]-isoGlu-Peg3-Peg3,
[19-carboxy-Nonadecanoyl]-isoGlu-Peg3-Peg3,
[17-carboxy-Heptadecanoyl]-isoGlu-Peg3-Peg3-Peg3,
[19-carboxy-Nonadecanoyl]-isoGlu-Peg3-Peg3-Peg3,
[17-carboxy-Heptadecanoyl]-isoLys,
[19-carboxy-Nonadecanoyl]-isoLys,

[17-carboxy-Heptadecanoyl]-isoLys-Peg3,
[19-carboxy-Nonadecanoyl]-isoLys-Peg3,
[17-carboxy-Heptadecanoyl]-isoLys-Peg3-Peg3,
[19-carboxy-Nonadecanoyl]-isoLys-Peg3-Peg3,
[17-carboxy-Heptadecanoyl]-isoLys-Peg3-Peg3-Peg3,
[19-carboxy-Nonadecanoyl]-isoLys-Peg3-Peg3-Peg3.

Yet further preferred substituents $Z^1$—$Z^2$— include:
[Hexadecanoyl]-KEK (SEQ ID NO: 251), [Octadecanoyl]-KEK (SEQ ID NO: 252),
[Hexadecanoyl]-βAla-Peg3,
[Hexadecanoyl]-KEK-Peg3 (SEQ ID NO: 258),
[Hexadecanoyl]-KEK-Peg3-Peg3 (SEQ ID NO: 263),
[Hexadecanoyl]-KEK-Peg3-Peg3-Peg3 (SEQ ID NO: 268),
[17-carboxy-Heptadecanoyl]-KEK (SEQ ID NO: 391),
[19-carboxy-Nonadecanoyl]-KEK (SEQ ID NO: 392),
[17-carboxy-Heptadecanoyl]-KEK-Peg3 (SEQ ID NO: 398),
[19-carboxy-Nonadecanoyl]-KEK-Peg3 (SEQ ID NO: 399),
[17-carboxy-Heptadecanoyl]-KEK-Peg3-Peg3 (SEQ ID NO: 403),
[19-carboxy-Nonadecanoyl]-KEK-Peg3-Peg3 (SEQ ID NO: 404),
[17-carboxy-Heptadecanoyl]-isoGlu-KEK (SEQ ID NO: 531),
[19-carboxy-Nonadecanoyl]-isoGlu-KEK (SEQ ID NO: 532),
[17-carboxy-Heptadecanoyl]-isoLys-KEK (SEQ ID NO: 533),
[19-carboxy-Nonadecanoyl]-isoLys-KEK (SEQ ID NO: 534),
[17-carboxy-Heptadecanoyl]-βAla-KEK (SEQ ID NO: 535),
[19-carboxy-Nonadecanoyl]-βAla-KEK (SEQ ID NO: 536),
[17-carboxy-Heptadecanoyl]-KEK-Peg3-Peg3-Peg3 (SEQ ID NO: 408),
[19-carboxy-Nonadecanoyl]-KEK-Peg3-Peg3-Peg3 (SEQ ID NO: 409),
[17-carboxy-Heptadecanoyl]-[4-aminobutanoyl]-KEK (SEQ ID NO: 537),
[19-carboxy-Nonadecanoyl]-[4-aminobutanoyl]-KEK (SEQ ID NO: 538),
[17-carboxy-Heptadecanoyl]-[4-aminobutanoyl]-KEK-Peg3-Peg3-Peg3 (SEQ ID NO: 468),
[19-carboxy-Nonadecanoyl]-[4-aminobutanoyl]-KEK-Peg3-Peg3-Peg3 (SEQ ID NO: 469),
[17-carboxy-Heptadecanoyl]-[4-aminobutanoyl]-KEK-Peg3-Peg3 (SEQ ID NO: 448),
[19-carboxy-Nonadecanoyl]-[4-aminobutanoyl]-KEK-Peg3-Peg3 (SEQ ID NO: 449)
[Hexadecanoyl]-isoGlu-KEK-Peg3 (SEQ ID NO: 273),
[Hexadecanoyl]-isoGlu-KEK-Peg3-Peg3 (SEQ ID NO: 293),
[17-carboxy-Heptadecanoyl]-isoGlu-KEK-Peg3-Peg3 (SEQ ID NO: 433),
[19-carboxy-Nonadecanoyl]-isoGlu-KEK-Peg3-Peg3 (SEQ ID NO: 434).

Examples of ψ comprising different substituents (fatty acids, FA), conjugated to the amino acid side-chain, optionally by a spacer, are illustrated below:

Fatty acids FA

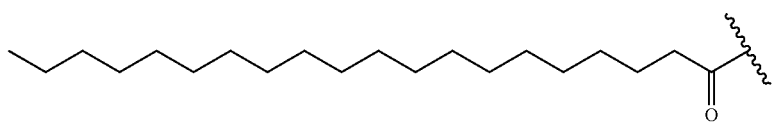

Eicosanoyl

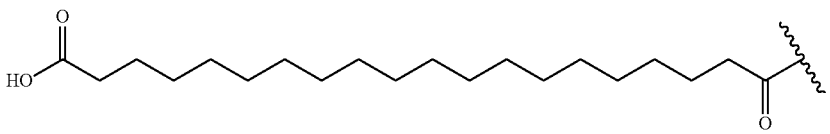

19-carboxy-nonadecanoyl

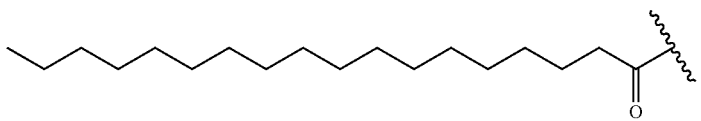

Octadecanoyl

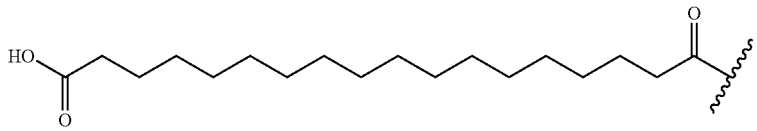

17-carboxy-heptadecanoyl

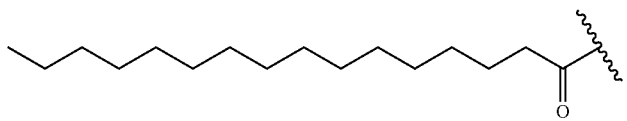

Hexadecanoyl

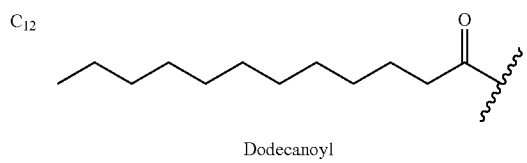
Dodecanoyl
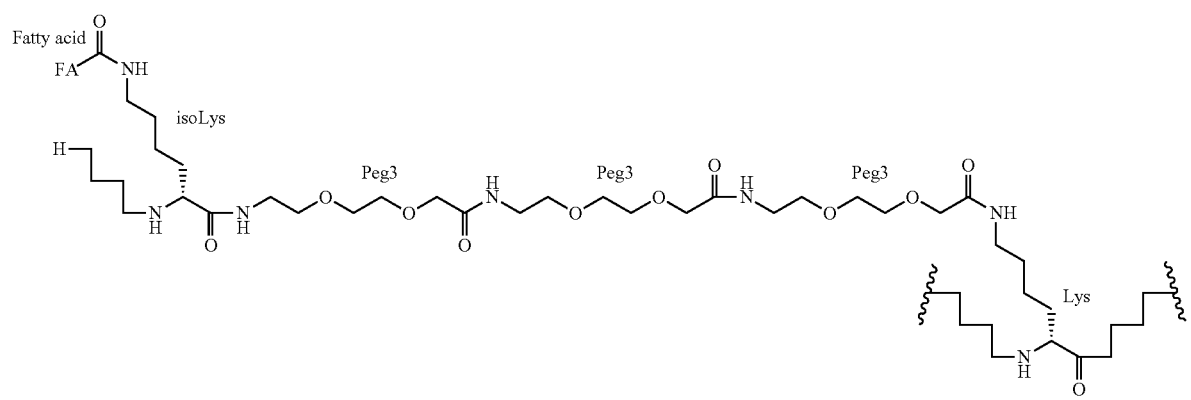
[K([Fatty acid]-isoLys-Peg3-Peg3Peg3)]
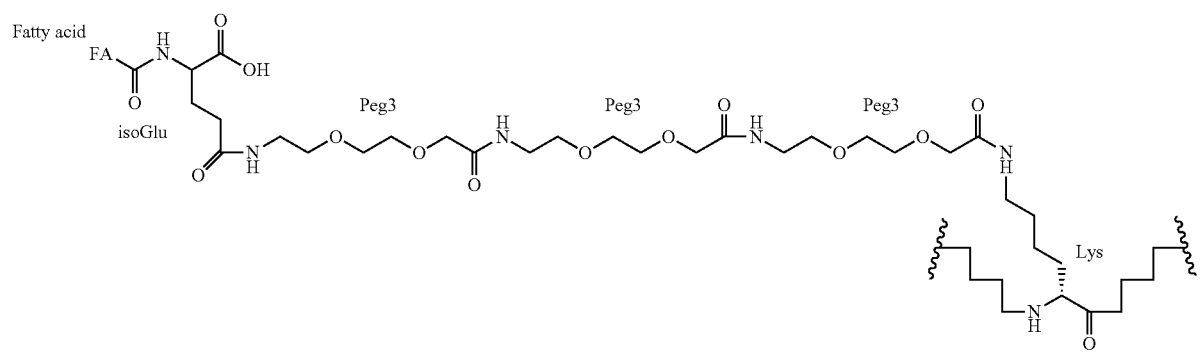
[K([Fatty acid]-isoGlu-Peg3-Peg3Peg3)]

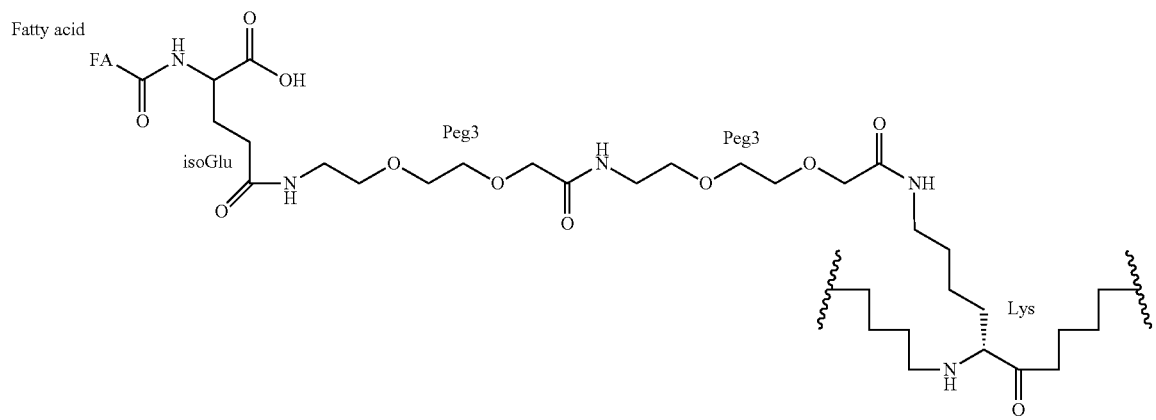
[K([Fatty acid]-isoGlu-Peg3-Peg3)]
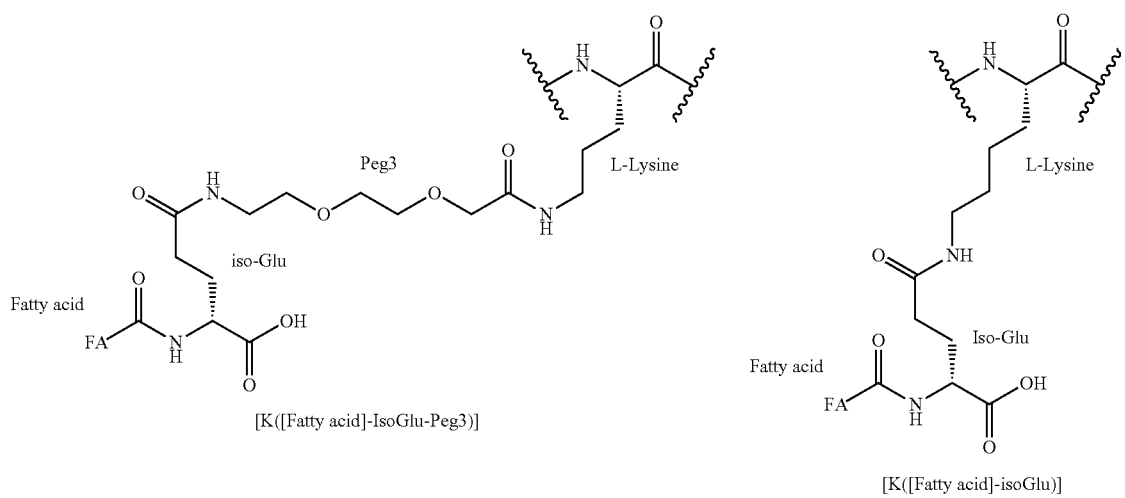
[K([Fatty acid]-IsoGlu-Peg3)]
[K([Fatty acid]-isoGlu)]
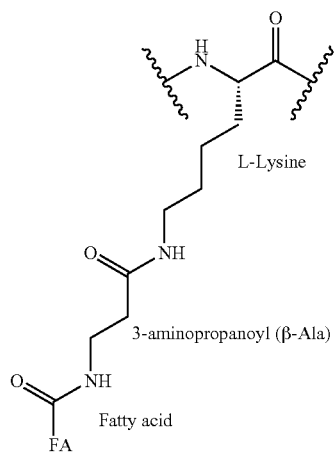
[K([Fatty acid-[3-aminopropanoyl])]

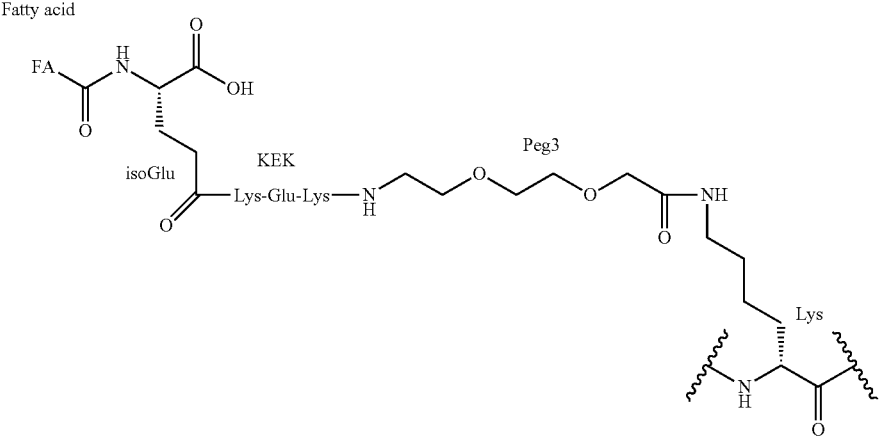

[K([Fatty acid]-isoGlu-KEK-Peg3)]

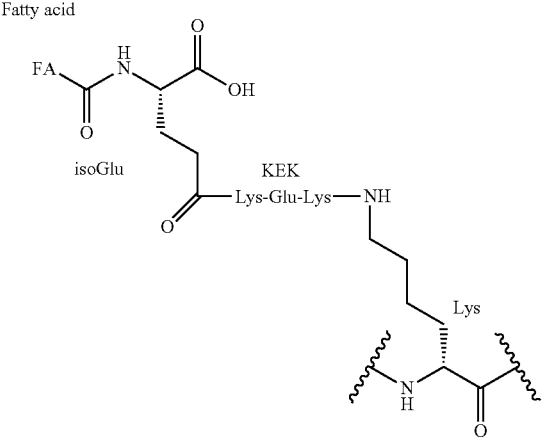

[K([Fatty acid]-isoGlu-KEK)]

Furthermore, the substituent [Hexadecanoyl]-isoGlu, conjugated to the side chain of a lysine residue, is illustrated below:

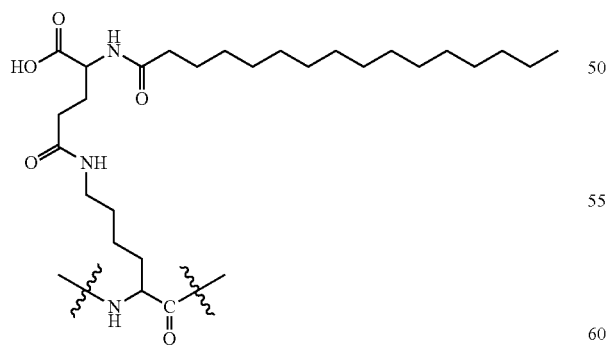

Thus, the side chain of the Lys residue is covalently attached to the side-chain carboxyl group of the isoGlu spacer —Z2-(—$Z^{S1}$—) via an amide linkage. A hexadecanoyl group ($Z^1$) is covalently attached to the amino group of the isoGlu spacer via an amide linkage.

The substituent [Hexadecanoyl]-[4-aminobutanoyl]-conjugated to the side chain of a lysine residue, is illustrated below
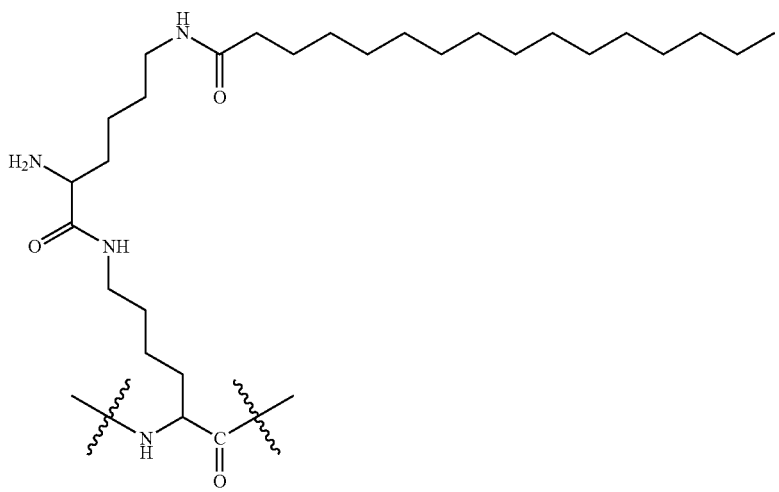 [SMILES: *NC(CCCCNC(=O)C(N)CCCCNC(=O)CCCCCCCCCCCCCCC)C(*)=O]
The substituent [(Hexadecanoyl)iso-Lys]-conjugated to the side chain of a lysine residue, is illustrated below
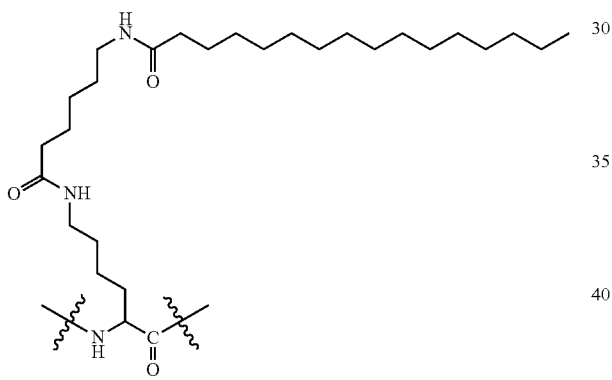
The substituent [(Hexadecanoyl)β-Ala]-conjugated to the side chain of a lysine residue, is illustrated below
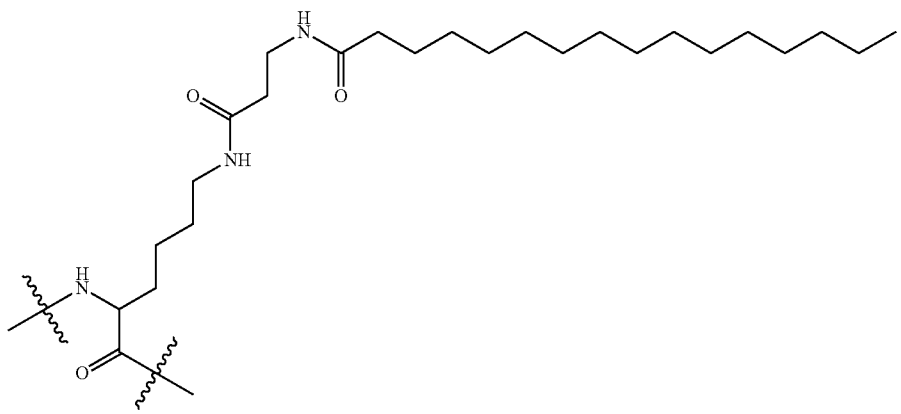 [SMILES: *NC(CCCCNC(=O)CCNC(=O)CCCCCCCCCCCCCCC)C(*)=O]

Some further specific examples of —$Z^2$—$Z^1$ combinations are illustrated below. In each case, — indicates the point of attachment to the side chain of the amino acid component of IP:
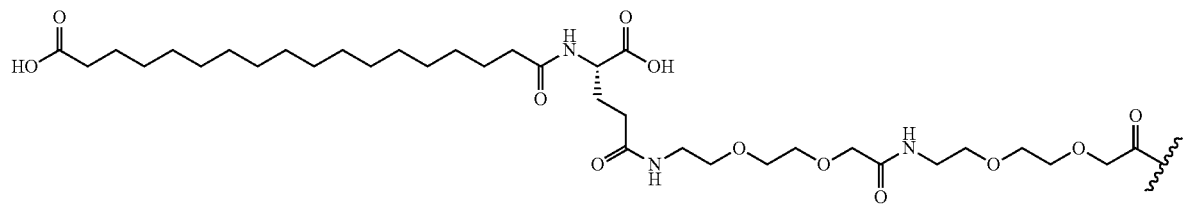
[17-Carboxy-heptadecanoyl]-isoGlu-Peg3-Peg3
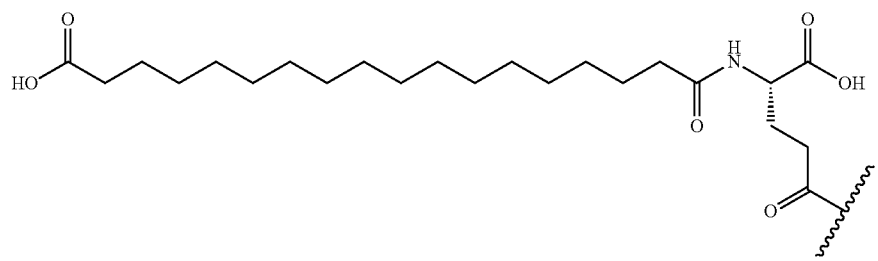
[17-Carboxy-heptadecanoyl]-isoGlu
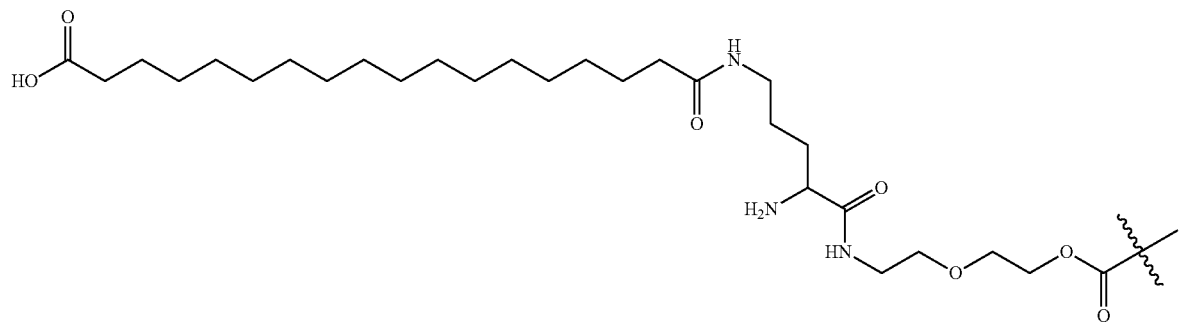
[17-carboxy-heptadecanoyl]-iso-Lys-Peg3
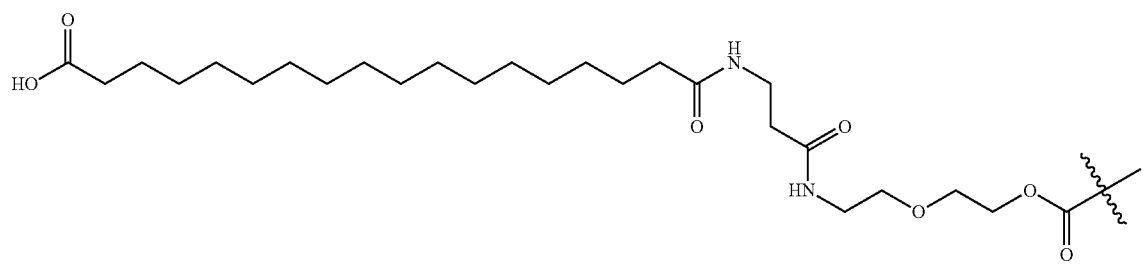
[17-carboxy-heptadecanoyl]-β-Ala-Peg3

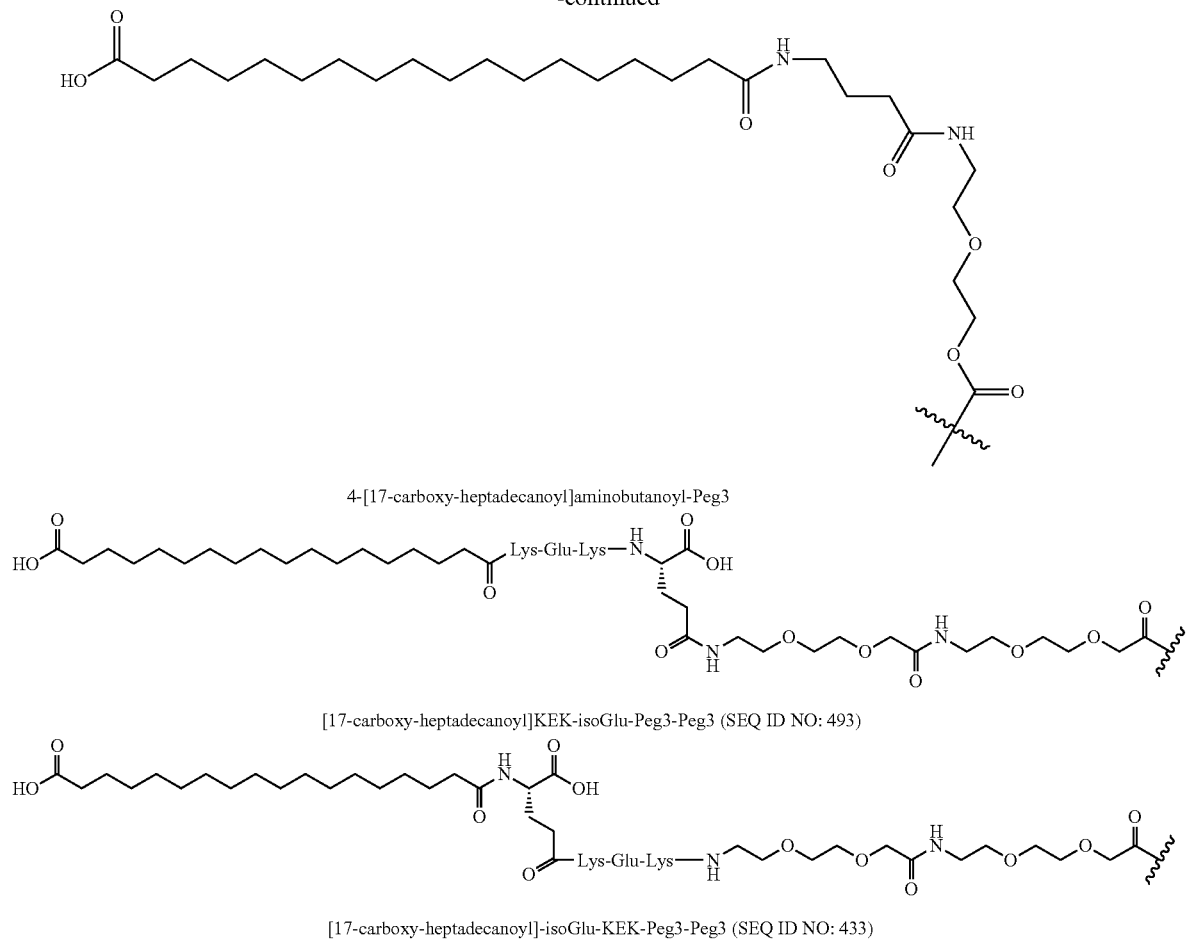

4-[17-carboxy-heptadecanoyl]aminobutanoyl-Peg3

[17-carboxy-heptadecanoyl]KEK-isoGlu-Peg3-Peg3 (SEQ ID NO: 493)

[17-carboxy-heptadecanoyl]-isoGlu-KEK-Peg3-Peg3 (SEQ ID NO: 433)

The skilled person will be well-aware of suitable techniques for preparing the substituents employed in the context of the invention and conjugating them to the side chain of the appropriate amino acid in the dual agonist peptide. For examples of suitable chemistry, see WO98/08871, WO00/55184, WO00/55119, Madsen et al., J. Med. Chem. 50:6126-32 (2007), and Knudsen et al., J. Med Chem. 43:1664-1669 (2000), incorporated herein by reference.

Synthesis of Dual Agonists

It is preferred to synthesize dual agonists of the invention by means of solid-phase or liquid-phase peptide synthesis methodology. In this context, reference may be made to WO 98/11125 and, among many others, Fields, G. B. et al., 2002, "Principles and practice of solid-phase peptide synthesis". In: Synthetic Peptides (2nd Edition), and the Examples herein.

In accordance with the present invention, a dual agonist of the invention may be synthesized or produced in a number of ways, including for example, a method which comprises:
(a) synthesizing the dual agonist by means of solid-phase or liquid-phase peptide synthesis methodology and recovering the synthesized dual agonist thus obtained; or
(b) expressing a precursor peptide sequence from a nucleic acid construct that encodes the precursor peptide, recovering the expression product, and modifying the precursor peptide to yield a compound of the invention.

The precursor peptide may be modified by introduction of one or more non-proteinogenic amino acids, e.g., Aib, Orn, Dap, or Dab, introduction of a lipophilic substituent $Z^1$ or $Z^1$—$Z^2$— at a residue ψ, introduction of the appropriate terminal groups $R^1$ and $R^2$, etc.

Expression is typically performed from a nucleic acid encoding the precursor peptide, which may be performed in a cell or a cell-free expression system comprising such a nucleic acid.

It is preferred to synthesize the analogues of the invention by means of solid-phase or liquid-phase peptide synthesis. In this context, reference is made to WO 98/11125 and, among many others, Fields, G B et al., 2002, "Principles and practice of solid-phase peptide synthesis". In: Synthetic Peptides (2nd Edition), and the Examples herein.

For recombinant expression, the nucleic acid fragments encoding the precursor peptide will normally be inserted in suitable vectors to form cloning or expression vectors. The vectors can, depending on purpose and type of application, be in the form of plasmids, phages, cosmids, mini-chromosomes, or virus, but also naked DNA which is only expressed transiently in certain cells is an important vector.

Preferred cloning and expression vectors (plasmid vectors) are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment, optionally a nucleic acid sequence encoding a leader peptide enabling secretion (to the extracellular phase or, where applicable, into the periplasma), the nucleic acid fragment encoding the precursor peptide, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the precursor peptide. Such transformed cells can be cultured cells or cell lines used for propagation of the nucleic acid fragments and vectors, and/or used for recombinant production of the precursor peptides.

Preferred transformed cells are micro-organisms such as bacteria [such as the species *Escherichia* (e.g., *E. coli*), *Bacillus* (e.g., *Bacillus subtilis*), *Salmonella*, or *Mycobacterium* (preferably non-pathogenic, e.g., *M. bovis* BCG), yeasts (e.g., *Saccharomyces cerevisiae* and *Pichia pastoris*), and protozoans. Alternatively, the transformed cells may be derived from a multicellular organism, i.e., it may be fungal cell, an insect cell, an algal cell, a plant cell, or an animal cell such as a mammalian cell. For the purposes of cloning and/or optimized expression it is preferred that the transformed cell is capable of replicating the nucleic acid fragment of the invention. Cells expressing the nucleic fragment can be used for small-scale or large-scale preparation of the peptides of the invention.

When producing the precursor peptide by means of transformed cells, it is convenient, although far from essential, that the expression product is secreted into the culture medium.

Pharmaceutical Compositions and Administration

An aspect of the present invention relates to a composition comprising a dual agonist according to the invention, or a pharmaceutically acceptable salt or solvate thereof, together with a carrier. In one embodiment of the invention, the composition is a pharmaceutical composition and the carrier is a pharmaceutically acceptable carrier. The present invention also relates to a pharmaceutical composition comprising a dual agonist according to the invention, or a salt or solvate thereof, together with a carrier, excipient or vehicle. Accordingly, the dual agonist of the present invention, or salts or solvates thereof, especially pharmaceutically acceptable salts or solvates thereof, may be formulated as compositions or pharmaceutical compositions prepared for storage or administration, and which comprise a therapeutically effective amount of a dual agonist of the present invention, or a salt or solvate thereof.

Suitable salts formed with bases include metal salts, such as alkali metal or alkaline earth metal salts, for example sodium, potassium or magnesium salts; ammonia salts and organic amine salts, such as those formed with morpholine, thiomorpholine, piperidine, pyrrolidine, a lower mono-, di- or tri-alkylamine (e.g., ethyl-tert-butyl-, diethyl-, diisopropyl-, triethyl-, tributyl- or dimethylpropylamine), or a lower mono-, di- or tri-(hydroxyalkyl)amine (e.g., mono-, di- or triethanolamine). Internal salts may also be formed. Similarly, when a compound of the present invention contains a basic moiety, salts can be formed using organic or inorganic acids. For example, salts can be formed from the following acids: formic, acetic, propionic, butyric, valeric, caproic, oxalic, lactic, citric, tartaric, succinic, fumaric, maleic, malonic, mandelic, malic, phthalic, hydrochloric, hydrobromic, phosphoric, nitric, sulphuric, benzoic, carbonic, uric, methanesulphonic, naphthalenesulphonic, benzenesulphonic, toluenesulphonic, p-toluenesulphonic (i.e. 4-methylbenzene-sulphonic), camphorsulphonic, 2-aminoethanesulphonic, aminomethylphosphonic and trifluoromethanesulphonic acid (the latter also being denoted triflic acid), as well as other known pharmaceutically acceptable acids. Amino acid addition salts can also be formed with amino acids, such as lysine, glycine, or phenylalanine.

In one embodiment, a pharmaceutical composition of the invention is one wherein the dual agonist is in the form of a pharmaceutically acceptable acid addition salt.

As will be apparent to one skilled in the medical art, a "therapeutically effective amount" of a dual agonist compound or pharmaceutical composition thereof of the present invention will vary depending upon, inter alia, the age, weight and/or gender of the subject (patient) to be treated. Other factors that may be of relevance include the physical characteristics of the specific patient under consideration, the patient's diet, the nature of any concurrent medication, the particular compound(s) employed, the particular mode of administration, the desired pharmacological effect(s) and the particular therapeutic indication. Because these factors and their relationship in determining this amount are well known in the medical arts, the determination of therapeutically effective dosage levels, the amount necessary to achieve the desired result of treating and/or preventing and/or remedying malabsorption and/or low-grade inflammation described herein, as well as other medical indications disclosed herein, will be within the ambit of the skilled person.

As used herein, the term "a therapeutically effective amount" refers to an amount which reduces symptoms of a given condition or pathology, and preferably which normalizes physiological responses in an individual with that condition or pathology. Reduction of symptoms or normalization of physiological responses can be determined using methods routine in the art and may vary with a given condition or pathology. In one aspect, a therapeutically effective amount of one or more dual agonists, or pharmaceutical compositions thereof, is an amount which restores a measurable physiological parameter to substantially the same value (preferably to within 30%, more preferably to within 20%, and still more preferably to within 10% of the value) of the parameter in an individual without the condition or pathology in question.

In one embodiment of the invention, administration of a compound or pharmaceutical composition of the present invention is commenced at lower dosage levels, with dosage levels being increased until the desired effect of preventing/treating the relevant medical indication is achieved. This would define a therapeutically effective amount. For the dual agonists of the present invention, alone or as part of a pharmaceutical composition, such human doses of the active dual agonist may be between about 0.01 µmol/kg and 500 µmol/kg body weight, between about 0.01 µmol/kg and 300 µmol/kg body weight, between 0.01 µmol/kg and 100 µmol/kg body weight, between 0.1 µmol/kg and 50 µmol/kg body weight, between 1 µmol/kg and 10 µmol/kg body weight, between 5 µmol/kg and 5 µmol/kg body weight, between 10 µmol/kg and 1 µmol/kg body weight, between 50 µmol/kg and 0.1 µmol/kg body weight, between 100 µmol/kg and 0.01 µmol/kg body weight, between 0.001 µmol/kg and 0.5 µmol/kg body weight, between 0.05 µmol/kg and 0.1 µmol/kg body weight.

The therapeutic dosing and regimen most appropriate for patient treatment will of course vary with the disease or condition to be treated, and according to the patient's weight and other parameters. Without wishing to be bound by any particular theory, it is expected that doses, in the µg/kg range, and shorter or longer duration or frequency of treatment may produce therapeutically useful results, such as a statistically significant increase particularly in small bowel mass. In some instances, the therapeutic regimen may include the administration of maintenance doses appropriate for preventing tissue regression that occurs following cessation of initial treatment. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

Medical Conditions

In a broad aspect, the present invention provides a dual agonist of the invention for use as a medicament.

In a further aspect, the present invention relates to a dual agonist of the invention for use in therapy.

The dual agonists described in this specification have biological activities of both GLP-1 and GLP-2.

GLP-2 induces significant growth of the small intestinal mucosal epithelium via the stimulation of stem cell proliferation in the crypts and inhibition of apoptosis on the villi (Drucker et al. Proc Natl Acad Sci USA. 1996, 93:7911-6). GLP-2 also has growth effects on the colon. GLP-2 also inhibits gastric emptying and gastric acid secretion (Wojdemann et al. J Clin Endocrinol Metab. 1999, 84:2513-7), enhances intestinal barrier function (Benjamin et al. Gut. 2000, 47:112-9.), stimulates intestinal hexose transport via the upregulation of glucose transporters (Cheeseman, Am J Physiol. 1997, R1965-71), and increases intestinal blood flow (Guan et al. Gastroenterology. 2003, 125, 136-47).

The beneficial effects of GLP-2 in the small intestine have raised considerable interest as to the use of GLP-2 in the treatment of intestinal disease or injury (Sinclair and Drucker, Physiology 2005: 357-65). Furthermore, GLP-2 has been shown to prevent or reduce mucosal epithelial damage in a wide number of preclinical models of gut injury, including chemotherapy-induced enteritis, ischemia-reperfusion injury, dextran sulfate-induced colitis and genetic models of inflammatory bowel disease (Sinclair and Drucker Physiology 2005: 357-65). The GLP-2 analogue teduglutide (Gly2-hGLP-2) is approved for treatment of short bowel syndrome under the trade names GATTEX® and REVESTIVE®.

GLP-1 is a peptide hormone known for its important role in glucose homeostasis. When secreted from the gastrointestinal tract in response to nutrient ingestion, GLP-1 potentiates glucose-stimulated insulin secretion from the β-cells (Kim and Egan, 2008, Pharmacol. Rev. 470-512). Furthermore, GLP-1 or its analogues has been shown to increase somatostatin secretion and suppress glucagon secretion (Hoist J J, 2007, Physiol Rev. 1409-1439).

Besides the primary actions of GLP-1 on glucose-stimulated insulin secretion, GLP-1 is also known as a key regulator of appetite, food intake, and body weight. Moreover, GLP-1 can inhibit gastric emptying and gastrointestinal motility in both rodents and humans, most likely through GLP-1 receptors present in the gastrointestinal tract (Hoist J J, 2007, Physiol Rev. 1409-1439; Hellstrom et al., 2008, Neurogastroenterol. Motil. June; 20(6):649-659). In addition, GLP-1 seems to have insulin-like effects in major extrapancreatic tissues, participating in glucose homeostasis and lipid metabolism in tissues such as muscle, liver, and adipose tissues (Kim and Egan, 2008, Pharmacol.Rev. 470-512).

Thus, the dual agonist compounds of the present invention may be used to increase intestinal mass, improve intestinal function (especially intestinal barrier function), increase intestinal blood flow, or repair intestinal damage or dysfunction (whether structural or functional), e.g., damage to the intestinal epithelium. They may also be used in the prophylaxis or treatment of conditions which may be ameliorated by these effects, and in reducing the morbidity related to gastrointestinal damage.

The dual agonists therefore find use in many gastrointestinal disorders. The term "gastrointestinal" is used here to include the entire gastrointestinal tract, including oesophagus, stomach, small intestine (duodenum, jejunum, ileum) and large intestine (cecum, colon, rectum), but especially the small intestine and colon.

Thus, conditions in which the dual agonists may be of benefit include malabsorption, ulcers (which may be of any etiology, e.g., peptic ulcers, Zollinger-Ellison Syndrome, drug-induced ulcers, and ulcers related to infections or other pathogens), short-bowel syndrome, cul-de-sac syndrome, inflammatory bowel disease (Crohn's disease and ulcerative colitis), irritable bowel syndrome (IBS), pouchitis, celiac sprue (for example arising from gluten induced enteropathy or celiac disease), tropical sprue, hypogammaglobulinemic sprue, and mucositis or diarrhea induced by chemotherapy or radiation therapy.

The dual agonists may also find use in certain conditions which do not primarily affect gastrointestinal tissue but which may be caused or exacerbated by factors arising from intestinal dysfunction. For example, impaired intestinal barrier function (which may be referred to as "leakiness" of the intestine or gut) can lead to transit of materials from the lumen of the gut directly into the bloodstream and thus to the kidney, lung and/or liver. These materials may include food molecules such as fats, which contribute to hepatitis and/or fatty liver diseases, including parenteral nutrition associated gut atrophy, PNALD (Parenteral Nutrition-Associated Liver Disease), NAFLD (Non-Alcoholic Fatty Liver Disease) and NASH (Non-Alcoholic Steatohepatitis). The materials crossing into the bloodstream may also include pathogens such as bacteria, and toxins such as bacterial lipopolysaccharide (LPS), which may contribute to systemic inflammation (e.g. vascular inflammation). Such inflammation is often referred to as "low grade inflammation" and is a contributing factor to the pathogenesis of metabolic endotoxemia (a condition seen in both diabetes and obesity, discussed further below), primary biliary cirrhosis and hepatitis. Entry of pathogens to the bloodstream may also result in conditions such as necrotising enterocolitis.

Low grade inflammation is not characterised by the normal symptoms of acute inflammation such as pain, fever and redness, but can be detected via the presence of inflammatory markers in the blood, such as C-reactive protein and pro-inflammatory cytokines including TNF-alpha (tumour necrosis factor alpha).

The dual agonists may also find use in conditions which primarily affect other tissues but have gastrointestinal side-effects. For example, inflammatory conditions such as pancreatitis result in elevated levels of circulating inflammatory mediators which may in turn induce intestinal damage or intestinal dysfunction, such as impairment of barrier function. In some circumstances, this may lead to more severe systemic inflammatory conditions such as sepsis, or to surgical procedures or mechanical injuries (volvulus) where blood supply to the intestine is interrupted, ultimately leading to ischaemia-reperfusion injuries.

Similarly, graft versus host disease (GVHD) may result in substantial tissue damage to the gastrointestinal tract, resulting in impaired barrier function and other side effects such as diarrhea. Thus, the dual agonists described may be useful for the prophylaxis or treatment of intestinal dysfunction or damage caused by or associated with GVHD, as well as prophylaxis or treatment of side effects such as diarrhea caused by or associated with GVHD.

The dual agonist compounds described herein also find use, inter alia, in reducing or inhibiting weight gain, reducing rate of gastric emptying or intestinal transit, reducing food intake, reducing appetite, or promoting weight loss. The effect on body weight may be mediated in part or wholly via reducing food intake, appetite or intestinal transit.

Thus, the dual agonists of the invention can be used for the prophylaxis or treatment of obesity, morbid obesity, obesity-linked gallbladder disease and obesity-induced sleep apnea.

Independently of their effect on body weight, the dual agonists of the invention may have a beneficial effect on glucose tolerance and/or glucose control. They may also be used to modulate (e.g. improve) circulating cholesterol levels, being capable of lowering circulating triglyceride or LDL levels, and increasing HDL/LDL ratio.

Thus, they may be used for the prophylaxis or treatment of inadequate glucose control, glucose tolerance or dyslipidemia (e.g., elevated LDL levels or reduced HDL/LDL ratio) and associated conditions, including diabetes (e.g., Type 2 diabetes, gestational diabetes), pre-diabetes, metabolic syndrome and hypertension.

Many of these conditions are also associated with obesity or overweight. The effects of the dual agonists on these conditions may therefore follow from their effect on body weight, in whole or in part, or may be independent thereof.

Effects on body weight may be therapeutic or cosmetic.

The dual agonist activity of the compounds described herein may be particularly beneficial in many of the conditions described, as the two activities may complement one another.

For example, malabsorption is a condition arising from abnormality in the absorption of water and/or food nutrients, such as amino acids, sugars, fats, vitamins or minerals, via the gastrointestinal (GI) tract, leading to malnutrition and/or dehydration. Malabsorption may be a result of physical (e.g. traumatic) or chemical damage to the intestinal tract. Dual agonists as described in this specification may be capable of improving intestinal barrier function, reducing gastric emptying, and increasing intestinal absorption while at the same time normalising intestinal transit time. This would not only help patients to increase the absorption of nutrients and liquid, but would also alleviate patients' social problems related to meal-stimulated bowel movements.

Furthermore, intestinal function and metabolic disorders may be closely inter-related, with each contributing to the development or symptoms of the other.

As mentioned above, obesity is linked with low grade inflammation (sometimes designated "obesity-linked inflammation"). It is also generally recognised that obesity (along with other syndromes) causes an increased vascular permeability which allows pathogens and toxins such as LPS to enter the cell wall of the intestinal tract and thereby initiate inflammation. The changes that result from the inflammatory response are essentially the same regardless of the cause and regardless of where the insult arises. The inflammatory response may be acute (short lived) or chronic (longer lasting).

It has been demonstrated that, e.g., obese mice (ob/ob and db/db mice) have a disrupted mucosal barrier function and exhibit increased low-grade inflammation (Brun et al., 2007, Am. J. Physiol. Gastrointest. Liver Physiol., 292: G518-G525, Epub 5 Oct. 2006). These observations were further extended to C57BL6/J mice maintained on a high-fat diet (Cani et al., 2008, Diabetes, vol. 57, 1470-1481) and to non-obese diabetic mice (Hadjiyanni et al., 2009, Endocrinology, 150(2): 592-599).

Cani and colleagues (Gut; 2009, 58:1091-1103,) reported that in ob/ob mice, the modulation of the gut microbiota resulted in decreased intestinal barrier dysfunction and reduced systemic inflammation via a GLP-2 dependent pathway. Further, the increased intestinal permeability observed in obese and diabetic patients is likely to play a more vital role in the disease progression than previously anticipated. Increased intestinal permeability leads to increased bacterial lipopolysaccharide (LPS) transport across the intestinal barrier. This increased LPS activates immune cells, such as circulating macrophages and macrophages residing in organs in the body, causing low-grade chronic inflammation that may be involved in the pathogenesis of many diseases. This phenomenon is called metabolic endotoxemia (ME).

The inflammatory process may also play a role in causing metabolic dysfunction in obese individuals, such as insulin resistance and other metabolic disturbances.

Thus, the dual agonist compounds of the invention may be particularly useful for prophylaxis or treatment of low grade inflammation, especially in obese or overweight individuals, exerting beneficial effects via the GLP-1 agonist component of their activity and/or the GLP-2 component of their activity.

The therapeutic efficacy of treatment with a dual agonist of the invention may be monitored by enteric biopsy to examine the villus morphology, by biochemical assessment of nutrient absorption, by non-invasive determination of intestinal permeability, by patient weight gain, or by amelioration of the symptoms associated with these conditions.

In a further aspect there is provided a therapeutic kit comprising a dual agonist of the invention, or a pharmaceutically acceptable salt or solvate thereof.

The following examples are provided to illustrate preferred aspects of the invention and are not intended to limit the scope of the invention in any way.

EXAMPLES

The following examples are provided to illustrate preferred aspects of the invention and are not intended to limit the scope of the invention.

Materials and Methods

General Peptide Synthesis

List of abbreviations and suppliers are provided in the table below

| | List of abbreviations and suppliers | | |
|---|---|---|---|
| | Abbreviation | Name | Brand/Supplier |
| Resins | | TENTAGEL ™ PHB AA(Proct)-Fmoc | Rapp Polymere |
| | | TENTAGEL ™ SRAM | Rapp Polymere |
| Amino | | Pseudoprolines (E.g. QT, AT, FS) | Jupiter Bioscience Ltd. |
| acids | | Fmoc-L-AA-OH | Senn Chemicals AG |
| Coupling reagents | COMU | (1-Cyano-2-ethoxy-2-oxoethylidenaminooxy)dimethyl-amino-morpholino-carbenium hexafluorophosphate | Watson International Ltd. |
| | DIC | Diisopropylcarbodiimide | Fluka/Sigma Aldrich Co. |
| | HATU | N-[(dimethylamino)-1H-1,2,3-tri-azol[4,5-b]pyridine-1-ylmethylene]-N-methylmethanaminium hexafluorophosphate N-oxide | ChemPep Inc. |
| | HOBt | Hydroxybenzotriazole | Sigma-Aldrich Co. |
| Solvents | Boc$_2$O | Di-tert-butyl pyrocarbonate | Advanced ChemTech |
| reagents | DCM | Dichloromethane | Prolabo (VWR) |
| | DIPEA | Diisopropylethylamine | Fluka/Sigma Aldrich Co. |
| | DMF | N,N-dimethylformamide | Taminco |
| | DODT | 3,6-dioxa-1,8-octanedithiol | Sigma-Aldrich Co. |
| | Et$_2$O | Diethyl ether | Prolabo (VWR) |
| | EtOH | Ethanol | CCS Healthcare AB |
| | | Formic acid (HPLC) | Sigma-Aldrich Co. |
| | H$_2$O | Water, MILLI-Q ™ water | Millipore |
| | MeCN | Acetonitrile (HPLC) | Sigma-Aldrich Co. |
| | NMP | N-methylpyrrolidone | Sigma-Aldrich Co. |
| | | Piperidine | Jubliant Life Sciences Ltd. |
| | TFA | Trifluoroacetic acid (HPLC) | Chemicals Raw Materials Ltd. |
| | TIS | Triisopropylsilane | Sigma-Aldrich Co. |
| | MeOH | Methanol | Sigma-Aldrich Co. |

Apparatus and Synthetic Strategy

Peptides were synthesized batchwise on a peptide synthesizer, such as a CEM LIBERTY™ Peptide Synthesizer or a SYMPHONY® X Synthesizer, according to solid phase peptide synthetic procedures using 9-fluorenylmethyloxy-carbonyl (Fmoc) as N-α-amino protecting group and suitable common protection groups for side-chain functionalities.

As polymeric support-based resins, such as e.g. TENTA-GEL™, was used. The synthesizer was loaded with resin that prior to usage was swelled in DMF.

Coupling

CEM LIBERTY™ Peptide Synthesizer

A solution of Fmoc-protected amino acid (4 equiv.) was added to the resin together with a coupling reagent solution (4 equiv.) and a solution of base (8 equiv.). The mixture was either heated by the microwave unit to 70-75° C. and coupled for 5 minutes or coupled with no heat for 60 minutes. During the coupling nitrogen was bubbled through the mixture.

SYMPHONY® X Synthesizer

The coupling solutions were transferred to the reaction vessels in the following order: amino acid (4 equiv.), HATU (4 equiv.) and DIPEA (8 equiv.). The coupling time was 10 min at room temperature (RT) unless otherwise stated. The resin was washed with DMF (5×0.5 min). In case of repeated couplings the coupling time was in all cases 45 min at RT.

Deprotection

CEM LIBERTY™ Peptide Synthesizer

The Fmoc group was deprotected using piperidine in DMF or other suitable solvents. The deprotection solution was added to the reaction vessel and the mixture was heated for 30 sec. reaching approx. 40° C. The reaction vessel was drained and fresh deprotection solution was added and subsequently heated to 70-75° C. for 3 min. After draining the reaction vessel, the resin was washed with DMF or other suitable solvents.

SYMPHONY® X Synthesizer

Fmoc deprotection was performed for 2.5 minutes using 40% piperidine in DMF and repeated using the same conditions. The resin was washed with DMF (5×0.5 min).

Side-Chain Acylation

A suitable trifunctional amino acid with an orthogonal side chain protecting group according to Fmoc methodology is introduced at the position of the acylation. The N-terminal of the growing peptide chain is then Boc-protected using Boc$_2$O or alternatively by using an N-α-Boc-protected amino acid in the last coupling. While the peptide is still attached to the resin, the orthogonal side chain protecting group is selectively cleaved using a suitable deprotection reagent. The lipophilic moiety is then coupled directly to the free sidechain functionality or alternatively via a linker in between according to suitable coupling protocols.

Cleavage

The dried peptide resin was treated with TFA and suitable scavengers for approximately 2 hours. The volume of the filtrate was reduced and the crude peptide was precipitated after addition of diethylether. The crude peptide precipitate was washed several times with diethylether and finally dried.

HPLC Purification of the Crude Peptide

The crude peptide was purified by preparative reverse phase HPLC using a conventional HPLC apparatus, such as a Gilson GX-281 with 331/332 pump combination, for binary gradient application equipped with a column, such as 5×25 cm Gemini NX 5u C18 110A column, and a fraction collector using a flow 20-40 ml/min with a suitable gradient of buffer A (0.1% Fomic acid, aq.) or A (0.1% TFA, aq.) and buffer B (0.1% Formic acid, 90% MeCN, aq.) or B (0.1% TFA, 90% MeCN, aq.). Fractions were analyzed by analytical HPLC and MS and selected fractions were pooled and lyophilized. The final product was characterized by HPLC and MS.

Analytical HPLC

Final purities were determined by analytic HPLC (Agilent 1100/1200 series) equipped with auto sampler, degasser, 20 µl flow cell and CHROMELEON™ software. The HPLC was operated with a flow of 1.2 ml/min at 40° C. using an analytical column, such as Kinetex 2.6 µm XB-C18 100A 100×4.6 mm column. The compound was detected and quantified at 215 nm. Buffers A (0.1% TFA, aq.) and buffer B (0.1% TFA, 90% MeCN, aq.).

Mass Spectroscopy

Final MS analysis were determined on a conventional mass spectroscopy, e.g., Waters XEVO® G2 Tof, equipped with electrospray detector with lock-mass calibration and MASSLYNX™ software. It was operated in positive mode using direct injection and a cone voltage of 15V (1 TOF), 30 V (2 TOF) or 45 V (3 TOF) as specified on the chromatogram. Precision was 5 ppm with a typical resolution of 15,000-20,000.

GLP-1 and GLP-2 Receptor Efficacy Assays

Peptides of this invention function as both GLP-1 and GLP-2 agonists and thus activate the GLP-1 receptor and GLP-2 receptor, respectively. One useful in vitro assay for measuring GLP-1 and GLP-2 receptor activity is quantitation of cAMP, i.e. 3'-5'-cyclic adenosine monophosphate, which is a second messenger essential in many biological processes, and one of the most ubiquitous mechanisms for regulating cellular functions. An example is the cAMP ALPHASCREEN® assay from Perkin Elmer which has been used to quantitate the cAMP response upon GLP-1 and GLP-2 receptor activation in HEK293 cells stably expressing GLP-1 R or GLP-2 R. Test compounds eliciting an increase in the intracellular level of cAMP can be tested in these assays, and the response normalized relative to a positive and negative control (vehicle) to calculate the EC50 and maximal response from the concentration response curve using the 4-parameter logistic (4PL) nonlinear model for curve fitting.

Example 1: Synthesis of the Compounds

Compounds Synthesised

The following compounds of Table 1 were synthesized using the above techniques.

TABLE 1

| | Compounds synthesized |
|---|---|
| 1 | Hy-H[Aib]EGTFSSELATILD[K([17-carboxy-heptadecanoyl]-isoGlu)]EAARDFIAWLIEHKITD-OH (SEQ ID NO: 183) |
| 2 | Hy-H[Aib]EGSFTSELATILD[K([17-carboxy-heptadecanoyl]-isoGlu)]EAARDFIAWLIEHKITD-OH (SEQ ID NO: 184) |
| 3 | Hy-H[Aib]EGTFTSELATILD[K([17-carboxy-heptadecanoyl]-isoGlu)]EAARDFIAWLIEHKITD-OH (SEQ ID NO: 185) |
| 4 | Hy-H[Aib]EGTFSSELATILD[K([17-carboxy-heptadecanoyl]-isoGlu)]KAARDFIAWLIEHKITD-OH (SEQ ID NO: 186) |
| 5 | Hy-H[Aib]EGSFTSELATILD[K([17-carboxy-heptadecanoyl]-isoGlu)]KAARDFIAWLIEHKITD-OH (SEQ ID NO: 187) |
| 6 | Hy-H[Aib]EGTFTSELATILD[K([17-carboxy-heptadecanoyl]-isoGlu)]KAARDFIAWLIEHKITD-OH (SEQ ID NO: 188) |
| 7 | Hy-H[Aib]EGTFSSELATILDG[K([17-carboxy-heptadecanoyl]-isoGlu)]AARDFIAWLIEHKITD-OH (SEQ ID NO: 189) |
| 8 | Hy-H[Aib]EGSFTSELATILDG[K([17-carboxy-heptadecanoyl]-isoGlu)]AARDFIAWLIEHKITD-OH (SEQ ID NO: 190) |
| 9 | Hy-H[Aib]EGTFTSELATILDG[K([17-carboxy-heptadecanoyl]-isoGlu)]AARDFIAWLIEHKITD-OH (SEQ ID NO: 191) |
| 10 | Hy-H[Aib]EGTFSSELATILD[K([17-carboxy-heptadecanoyl]-isoGlu)]LAARDFIAWLIEHKITD-OH (SEQ ID NO: 192) |
| 11 | Hy-H[Aib]EGSFTSELATILD[K([17-carboxy-heptadecanoyl]-isoGlu)]LAARDFIAWLIEHKITD-OH (SEQ ID NO: 193) |
| 12 | Hy-H[Aib]EGTFTSELATILD[K([17-carboxy-heptadecanoyl]-isoGlu)]LAARDFIAWLIEHKITD-OH (SEQ ID NO: 194) |
| 13 | Hy-H[Aib]EGTFSSELATILD[K([17-carboxy-heptadecanoyl]-isoGlu)]LAARDFIAWLIAHKITD-OH (SEQ ID NO: 195) |
| 14 | Hy-H[Aib]EGSFTSELATILD[K([17-carboxy-heptadecanoyl]-isoGlu)]LAARDFIAWLIAHKITD-OH (SEQ ID NO: 196) |
| 15 | Hy-H[Aib]EGTFTSELATILD[K([17-carboxy-heptadecanoyl]-isoGlu)]LAARDFIAWLIAHKITD-OH (SEQ ID NO: 197) |
| 16 | Hy-H[Aib]EGTFTSELATILD[K([17-carboxy-heptadecanoyl]-isoGlu)]QAARDFIAWLIQHKITD-OH (SEQ ID NO: 199) |
| 18 | Hy-H[Aib]EGSFTSELATILD[K([17-carboxy-heptadecanoyl]-isoGlu)]QAARDFIAWLIQHKITD-OH (SEQ ID NO: 200) |

TABLE 1-continued

| | Compounds synthesized |
|---|---|
| 19 | Hy-H[Aib]EGTFTSELATILD[K([17-carboxy-heptadecanoyl]-isoGlu)]QAARDFIAWLIQHKITD-OH (SEQ ID NO: 201) |
| 20 | Hy-H[Aib]EGTFSSELATILD[K([17-carboxy-heptadecanoyl]-isoGlu)]QAARDFIAWLIEHKITD-OH (SEQ ID NO: 202) |
| 21 | Hy-H[Aib]EGTFSSELATILD[K([17-carboxy-heptadecanoyl]-isoGlu)]QAARDFIAWLIAHKITD-OH (SEQ ID NO: 203) |
| 22 | Hy-H[Aib]EGSFTSELATILD[K([17-carboxy-heptadecanoyl]-isoGlu)]QAARDFIAWLIAHKITD-OH (SEQ ID NO: 204) |
| 23 | Hy-H[Aib]EGTFTSELATILD[K([17-carboxy-heptadecanoyl]-isoGlu)]QAARDFIAWLIAHKITD-OH (SEQ ID NO: 205) |
| 24 | Hy-H[Aib]EGSFTSELATILD[K([17-carboxy-heptadecanoyl]-isoGlu)]QAARDFIAWLIEHKITD-OH (SEQ ID NO: 206) |
| 25 | Hy-H[Aib]EGTFTSELATILD[K([17-carboxy-heptadecanoyl]-isoGlu)]QAARDFIAWLIEHKITD-OH (SEQ ID NO: 207) |
| 26 | Hy-H[Aib]EGSFTSELATILD[K([17-carboxy-heptadecanoyl]-isoGlu)]QAARDFIAWLIHHKITD-OH (SEQ ID NO: 208) |
| 27 | Hy-H[Aib]EGSFTSELATILD[K([17-carboxy-heptadecanoyl]-isoGlu)]QAARDFIAWLIYHKITD-OH (SEQ ID NO: 209) |
| 28 | Hy-H[Aib]EGSFTSELATILD[K([17-carboxy-heptadecanoyl]-isoGlu)]QAARDFIAWLILHKITD-OH (SEQ ID NO: 210) |
| 29 | Hy-H[Aib]EGSFTSELATILD[K([17-carboxy-heptadecanoyl]-isoGlu)]QAARDFIAWLIKHKITD-OH (SEQ ID NO: 211) |
| 30 | Hy-H[Aib]EGSFTSELATILD[K([17-carboxy-heptadecanoyq-isoGlu)]QAARDFIAWLIRHKITD-OH (SEQ ID NO: 212) |
| 31 | Hy-H[Aib]EGSFTSELATILD[K([17-Carboxy-heptadecanoyl]-isoGlu)]QAARDFIAWLISHKITD-OH (SEQ ID NO: 213) |
| 32 | Hy-H[Aib]EGSFTSELATILD[K([Hexadecanoyl]-βAla)]QAARDFIAWLQQHKITD-OH (SEQ ID NO: 214) |
| 33 | Hy-H[Aib]EGSFTSELATILD[K([17-carboxy-heptadecanoyl]-isoGlu-Peg3)+QAARDFIAWLYQHKITD-OH (SEQ ID NO: 215) |
| 34 | Hy-H[Aib]EGSFTSELATILD[K([19-carboxy-nonadecanoyl]-isoGlu-Peg3-Peg3)+QAARDFIAWLKQHKITD-OH (SEQ ID NO: 216) |
| 35 | Hy-H[Aib]EGSFTSELATILD[K([19-carboxy-nonadecanoyl]iso-Lys-Peg3-Peg3)+QAARDFIAWLIQQKITD-OH (SEQ ID NO: 217) |
| 36 | Hy-H[Aib]EGSFTSELATILD[K(Octadecanoyl)]QAARDFIAWLIQYKITD-OH (SEQ ID NO: 218) |
| 37 | Hy-H[Aib]EGTFSSELSTILE[K(Hexadecanoyl-isoGlu)]QASREFIAWLIAYKITE-OH (SEQ ID NO: 219) |
| 38 | Hy-H[Aib]EGTFSSELATILDEQAARDFIAWLIAHKITDkkkkkk([17-carboxy-Heptadecanoyl]-isoGlu)]-[NH2] (SEQ ID NO: 220) |
| 39 | Hy-H[Aib]EGTFTSELATILDEQAARDFIAWLIAHKITDkkkkkk([17-carboxy-Heptadecanoyl]-isoGlu)]-[NH2] (SEQ ID NO: 221) |
| 40 | Hy-H[Aib]EGSFTSELATILDEQAARDFIAWLIEHKITDkkkkkk([17-carboxy-Heptadecanoyl]-isoGlu)]-[NH2] (SEQ ID NO: 222) |
| 41 | Hy-H[Aib]EGTFTSELATILD[K([19-Carboxy-nonadecanoyl]-isoGlu)]QAARDFIAWLIQHKITD-OH (SEQ ID NO: 223) |
| 42 | Hy-H[Aib]EGSFTSE[K([19-carboxy-nonadecanoyl]-isoGlu-Peg3-Peg3)]ATILDEQAARDFIAWLIEHKITD-OH (SEQ ID NO: 224) |
| 43 | Hy-H[Aib]EGSFTSELATILD[K([19-carboxy-nonadecanoyl]-isoGlu-Peg3-Peg3)]KAARDFIAWLIEHKITD-OH (SEQ ID NO: 225) |
| 44 | Hy-H[Aib]EGSFTSELATILEG[K([19-carboxy-nonadecanoyl]-isoGlu-Peg3-Peg3)]AARDFIAWLIEHKITD-OH (SEQ ID NO: 226) |

TABLE 1-continued

Compounds synthesized

| | |
|---|---|
| 45 | Hy-H[Aib]EGSFTSELATILDEQAA[K([19-carboxy-nonadecanoyl]-isoGlu-Peg3-Peg3)(SEQ ID NO: 227) |
| 46 | Hy-H[Aib]EGTFTSELATILDEQAA[K([19-carboxy-nonadecanoyl]-isoGlu-Peg3-Peg3)(SEQ ID NO: 228) |
| 47 | Hy-H[Aib]EGTFSSELATILD[K([17-Carboxy-heptadecanoyl]-isoGlu-KEK-Peg3)]QAARDFIAWLIQHKITD-OH (SEQ ID NO: 229) |
| 48 | Hy-H[Aib]EGTFSSELATILD[K([19-Carboxy-nonadecanoyl]-isoGlu-KEK-Peg3)]QAARDFIAWLIQHKITD-OH (SEQ ID NO: 230) |
| 49 | Hy-H[Aib]EGTFSSELATILD[K([17-Carboxy-heptadecanoyl]-isoGlu-KEK-Peg3)]QAARDFIAWLIEHKITD-OH (SEQ ID NO: 231) |
| 50 | Hy-H[Aib]EGTFSSELATILD[K([19-Carboxy-nonadecanoyl]-isoGlu-KEK-Peg3)]QAARDFIAWLIEHKITD-OH (SEQ ID NO: 232) |
| 51 | Hy-H[Aib]EGTFTSELATILD[K([19-Carboxy-nonadecanoyl]-isoGlu-KEK)]QAARDFIAWLIQHKITD-OH (SEQ ID NO: 233) |
| 52 | Hy-H[Aib]EGTFTSELATILD[K([19-Carboxy-nonadecanoyl]-isoGlu-KEK-Peg3)]QAARDFIAWLIQHKITD-OH (SEQ ID NO: 234) |
| 53 | Hy-H[Aib]EGSFTSE[K([19-Carboxy-nonadecanoyl]-isoGlu-KEK-Peg3)]ATILDEQAARDFIAWLIEHKITD-OH (SEQ ID NO: 235) |
| 54 | Hy-H[Aib]EGTFTSE[K([19-Carboxy-nonadecanoyl]-isoGlu-KEK-Peg3)]ATILDEQAARDFIAWLIEHKITD-OH (SEQ ID NO: 236) |
| 55 | Hy-H[Aib]EGSFTSE[K([19-carboxy-nonadecanoyl]iso-Glu-KEK-Peg3-Peg3)]ATILDEQAARDFIAWLIEHKITD-OH (SEQ ID NO: 237) |
| 56 | Hy-H[Aib]EGTFTSELATILD[K([19-Carboxy-nonadecanoyl]-isoGlu-KEK-Peg3)]QAARDFIAWLIEHKITD-OH (SEQ ID NO: 238) |
| 57 | Hy-H[Aib]EGSFTSELATILD[K([19-Carboxy-nonadecanoyl]-isoGlu-KEK-Peg3)]QAARDFIAWLIEHKITD-OH (SEQ ID NO: 239) |
| 58 | Hy-H[Aib]EGSFTSELATILD[K([19-Carboxy-nonadecanoyl]-isoGlu-KEK-Peg3)]QAARDFIAWLIAHKITD-OH (SEQ ID NO: 240) |
| 59 | Hy-H[Aib]EGSFTSELATILD[K([19-Carboxy-nonadecanoyl]-isoGlu-KEK-Peg3)]KAARDFIAWLIEHKITD-OH (SEQ ID NO: 241) |
| 60 | Hy-H[Aib]EGSFTSELATILD[K([19-carboxy-nonadecanoyl]iso-Glu-KEK-Peg3-Peg3)]QAARDFIAWLIEHKITD-OH (SEQ ID NO: 242) |
| 61 | Hy-H[Aib]EGSFTSELATILEG[K([19-Carboxy-nonadecanoyl]-isoGlu-KEK-Peg3)]AARDFIAWLIEHKITD-OH (SEQ ID NO: 243) |
| 62 | Hy-H[Aib]EGSFTSELATILDA[K([19-Carboxy-nonadecanoyl]-isoGlu-KEK-Peg3)]AARDFIAWLIEHKITD-OH (SEQ ID NO: 244) |
| 63 | Hy-H[Aib]EGSFTSELATILDA[K([19-carboxy-nonadecanoyl]iso-Glu-KEK-Peg3-Peg3)]AARDFIAWLIEHKITD-OH (SEQ ID NO: 245) |
| 64 | Hy-H[Aib]EGSFTSELATILDEQAA[K([19-Carboxy-nonadecanoyl]-isoGlu-KEK-Peg3)(SEQ ID NO: 246) |
| 65 | Hy-H[Aib]EGTFTSELATILDEQAA[K([19-Carboxy-nonadecanoyl]-isoGlu-KEK-Peg3)(SEQ ID NO: 247) |
| 66 | Hy-H[Aib]EGSFTSELATILDEQAA[K([19-carboxy-nonadecanoyl]iso-Glu-KEK-Peg3-Peg3)(SEQ ID NO: 248) |
| 67 | Hy-H[Aib]EGTFTSELATILDEQAA[K([19-carboxy-nonadecanoyl]iso-Glu-KEK-Peg3-Peg3)(SEQ ID NO: 249) |
| 68 | Hy-H[Aib]EGSFTSELATILDAKAA[K([19-Carboxy-nonadecanoyl]-isoGlu-KEK-Peg3)(SEQ ID NO: 250) |

The following reference compounds A and B were also synthesized:

A
(SEQ ID NO: 539)
Hy-H[Aib]DGSFSSELATILD[K([17-carboxy-
heptadecanoyl]-isoGlu)]QAARDFIAWLIQHKITD-OH
B
(SEQ ID NO: 540)
Hy-H[Aib]EGSFSSELATILD[K([17-carboxy-
heptadecanoyl]-isoGlu)]QAARDFIAWLIQHKITD-OH For illustration purposes only, the synthesis of two selected compounds is described in detail below.

Synthesis of Compound 17

(SEQ ID NO: 199)
H-H[Aib]EGTFSSELATILD[K([17-carboxy-heptadecanoyl]-
isoGlu)]QAARDFIAWLIQHKITD-OH Solid phase peptide synthesis was performed on a SYMPHONY® X Synthesizer using standard Fmoc chemistry. TENTAGEL™ S PHB Asp(tBu)Fmoc (1.15 g; 0.23 mmol/g) was swelled in DMF (10 ml) prior to use and the Fmoc-group was deprotected according to the procedure described above.

Coupling

Suitable protected Fmoc-amino acids according to the sequence were coupled as described above using HATU as coupling reagent. All couplings were performed at R.T. In order to facilitate the synthesis, a pseudoproline were used: in position 6 and 7 Fmoc-Phe-Ser(psi Me,Mepro)-OH. Acylation in position 16 was obtained according to the side-chain acylation procedure described above. The pseudoproline was coupled according to the standard procedure described above for Fmoc-amino acids.

Deprotection

Fmoc deprotection was performed according to the procedure described above.

Cleavage of the Peptide from the Solid Support

The peptide-resin was washed with EtOH (3×10 ml) and Et2O (3×10 ml) and dried to constant weight at room temperature (r.t.). The peptide was cleaved from the resin by treatment with TFA/TIS/H$_2$O (95/2.5/2.5; 40 ml, 2 h; r.t.). The volume of the filtrate was reduced and the crude peptide was precipitated after addition of diethylether. The crude peptide precipitate was washed several times with diethylether and finally dried to constant weight at room temperature yield 1100 mg crude peptide product (purity ~40%).

HPLC Purification of the Crude Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 35 ml/min with a gradient of buffer A (0.1% TFA, aq.) and buffer B (0.1% TFA, 90% MeCN, aq.) gradient from 25% B to 60% B in 47 min. Fractions were analyzed by analytical HPLC and MS and relevant fractions were pooled and lyophilized to yield 105.7 mg, with a purity of 91% as characterized by HPLC and MS as described above. Calculated monoisotopic MW=4164.21, found 4164.23.

Synthesis of Compound 4

(SEQ ID NO: 186)
H-H[Aib]EGTFSSELATILD[K([17-carboxy-heptadecanoyl]-
isoGlu)]KAARDFIAWLIEHKITD-OH Solid phase peptide synthesis was performed on a SYMPHONY® X Synthesizer using standard Fmoc chemistry. TENTAGEL™ S PHB Asp(tBu)Fmoc (1.20 g; 0.23 mmol/g) was swelled in DMF (10 ml) prior to use and the Fmoc-group was deprotected according to the procedure described above.

Coupling

Suitable protected Fmoc-amino acids according to the sequence were coupled as described above using HATU as coupling reagent. All couplings were performed at R.T. In order to facilitate the synthesis, a pseudoproline were used: in position 6 and 7 Fmoc-Phe-Ser(psi Me,Mepro)-OH. Acylation in position 16 was obtained according to the side-chain acylation procedure described above. The pseudoproline was coupled according to the standard procedure described above for Fmoc-amino acids.

Deprotection

Fmoc deprotection was performed according to the procedure described above.

Cleavage of the Peptide from the Solid Support

The peptide-resin was washed with EtOH (3×10 ml) and Et2O (3×10 ml) and dried to constant weight at room temperature (r.t.). The peptide was cleaved from the resin by treatment with TFA/TIS/H$_2$O (95/2.5/2.5; 40 ml, 2 h; r.t.). The volume of the filtrate was reduced and the crude peptide was precipitated after addition of diethylether. The crude peptide precipitate was washed several times with diethylether and finally dried to constant weight at room temperature yield 900 mg crude peptide product (purity ~35%).

HPLC Purification of the Crude Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 35 ml/min with a gradient of buffer A (0.1% TFA, aq.) and buffer B (0.1% TFA, 90% MeCN, aq.) gradient from 30% B to 65% B in 47 min. Fractions were analyzed by analytical HPLC and MS and relevant fractions were pooled and lyophilized to yield 100.7 mg, with a purity of 91% as characterized by HPLC and MS as described above. Calculated monoisotopic MW=4165.23, found 4165.26.

Example 2: GLP-1R and GLP-2R EC$_{50}$ Measurements

Generation of cell line expressing human GLP-1 receptors

The cDNA encoding the human glucagon-like peptide 1 receptor (GLP-1 R) (primary accession number P43220) was cloned from the cDNA BC112126 (MGC:138331/IMAGE:8327594). The DNA encoding the GLP-1-R was amplified by PCR using primers encoding terminal restriction sites for subcloning. The 5'-end primers additionally encoded a near Kozak consensus sequence to ensure efficient translation. The fidelity of the DNA encoding the GLP-1-R was confirmed by DNA sequencing. The PCR products encoding the GLP-1-R were subcloned into a mammalian expression vector containing a neomycin (G418) resistance marker. The mammalian expression vectors encoding the GLP-1-R were transfected into HEK293 cells by a standard calcium phosphate transfection method.

48 hours post-transfection, cells were seeded for limited dilution cloning and selected with 1 mg/ml G418 in the culture medium. Following 3 weeks in G418 selection clones were picked and tested in a functional GLP-1 receptor potency assay as described below. One clone was selected for use in compound profiling.

Generation of Cell Line Expressing Human GLP-2 Receptors

The hGLP2-R was purchased from MRC-geneservice, Babraham, Cambridge as an Image clone: 5363415 (11924-I17). For subcloning into a mammalian expression vector, primers for subcloning were obtained from DNA-Technology, Risskov, Denmark. The 5' and 3' primers used for the PCR reaction include terminal restriction sites for cloning and the context of the 5' primer is modified to a Kozak consensus without changing the sequence of the product encoded by the ORF. A standard PCR reaction was run using Image clone 5363415 (11924-117) as a template with the above-mentioned primers and Polymerase HERCULASE® II Fusion in a total vol. of 50 µl. The generated PCR product was purified using GFX PCR and Gel band purification kit, digested with restriction enzymes and cloned into the mammalian expression vector using Rapid DNA Ligation Kit. Ligation reaction was transformed to XL10 Gold Ultracompetent cells and colonies were picked for DNA production using ENDOFREE® Plasmid maxi kit. Subsequent sequence analysis was conducted by MWG Eurofins, Germany. The clone was confirmed to be the hGLP-2 (1-33) receptor, splice variant rs17681684.

HEK293 cells were transfected using the LIPOFECTAMINE® PLUS transfection method. The day before transfection, HEK293 cells were seeded in two T75 flasks at a density of $2 \times 10^6$ cells/T75 flask in cell culturing medium without antibiotics. On the day of transfection, cells were washed with 1×DPBS and medium was replaced with OPTI-MEM® to a volume of 5 mL/T75 flask before addition of LIPOFECTAMINE®-plasmid complexes were added gently and drop wise to the cells in T75 flasks and replaced with growth medium after 3 hours and again to growth medium supplemented with 500 µg/mL G418 after 24 hours. Following 4 weeks in G418 selection, clones were picked and tested in a functional GLP-2 receptor potency assay as described below. One clone was selected for use in compound profiling.

GLP-1 R and GLP-2 Receptor Potency Assays

The cAMP ALPHASCREEN® assay from Perkin Elmer was used to quantitate the cAMP response to activation of the GLP1 and GLP2 receptor, respectively. Exendin-4 was used as reference compound for GLP1 receptor activation and Teduglutide as reference compound for GLP2 receptor activation. Data from test compounds eliciting an increase in the intracellular level of cAMP were normalized relative to the positive and negative control (vehicle) to calculate the $EC_{50}$ and maximal response from the concentration response curve. The results are listed in Table 2.

TABLE 2

| Compound | $EC_{50}$ GLP-1 (nM) | $EC_{50}$ GLP-2 (nM) |
|---|---|---|
| Teduglutide | 39 | 0.027 |
| Liraglutide | 0.029 | N/A |
| A | 0.490 | 0.083 |
| B | 3.900 | 0.280 |
| 1 | 0.630 | 0.350 |
| 2 | 0.130 | 0.250 |

TABLE 2-continued

| Compound | $EC_{50}$ GLP-1 (nM) | $EC_{50}$ GLP-2 (nM) |
|---|---|---|
| 3 | 0.042 | 0.330 |
| 4 | 0.660 | 0.087 |
| 5 | 0.170 | 0.063 |
| 6 | 0.058 | 0.120 |
| 7 | 0.920 | 0.019 |
| 8 | 0.220 | 0.039 |
| 9 | 0.056 | 0.056 |
| 10 | 1.800 | 0.087 |
| 11 | 0.320 | 0.085 |
| 12 | 0.140 | 0.110 |
| 13 | 2.200 | 0.099 |
| 14 | 0.570 | 0.086 |
| 15 | 0.250 | 0.160 |
| 16 | 0.073 | 0.680 |
| 17 | 0.900 | 0.330 |
| 18 | 0.190 | 0.210 |
| 19 | 0.066 | 0.230 |
| 20 | 0.550 | 0.370 |
| 21 | 1.800 | 0.270 |
| 22 | 0.230 | 0.200 |
| 23 | 0.130 | 0.240 |
| 24 | 0.210 | 0.170 |
| 25 | 0.094 | 0.330 |
| 26 | 0.290 | 0.590 |
| 27 | 0.450 | 1.100 |
| 28 | 0.360 | 0.510 |
| 29 | 0.310 | 0.290 |
| 30 | 0.310 | 0.380 |
| 31 | 0.270 | 0.240 |
| 32 | 0.380 | 0.460 |
| 33 | 0.850 | 0.072 |
| 34 | 0.280 | 0.130 |
| 35 | 0.099 | 0.300 |
| 36 | 0.320 | 3.200 |
| 38 | 0.250 | 0.890 |
| 39 | 0.044 | 0.980 |
| 40 | 0.074 | 0.500 |
| 41 | 0.048 | 0.620 |
| 42 | 0.067 | 0.330 |
| 43 | 0.096 | 0.150 |
| 44 | 0.063 | 0.140 |
| 45 | 1.400 | 0.360 |
| 46 | 0.260 | 0.380 |
| 47 | 0.440 | 0.048 |
| 48 | 0.470 | 0.054 |
| 49 | 0.270 | 0.044 |
| 50 | 0.310 | 0.056 |
| 51 | 0.020 | 0.180 |
| 52 | 0.020 | 0.075 |
| 53 | 0.076 | 0.240 |
| 54 | 0.034 | 0.990 |
| 55 | 0.110 | 0.780 |
| 56 | 0.033 | 0.076 |
| 57 | 0.093 | 0.083 |
| 58 | 0.089 | 0.090 |
| 59 | 0.088 | 0.110 |
| 60 | 0.097 | 0.074 |
| 61 | 0.130 | 0.200 |
| 62 | 0.270 | 0.150 |
| 63 | 0.310 | 0.170 |
| 64 | 0.490 | 0.200 |
| 65 | 0.130 | 0.350 |
| 66 | 0.650 | 0.180 |
| 67 | 0.160 | 0.220 |
| 68 | 0.084 | 0.100 |

N/A = no detectable activity

Example 3: Solubility Assessment

A stock solution of the test peptide (2 mg/ml; determined from the weighed amount of peptide) in demineralized water adjusted to pH 2.5 with HCl was prepared, and aliquots were diluted 1:1 in 100 mM acetate buffer (pH 4.0 and pH 5.0), 100 mM histidine buffer (pH 6.0 and pH 7.0) and 100 mM phosphate buffer (pH 6.0, pH 7.0 and pH 7.5), respectively, and loaded in a standard flat-bottom, non-sterile 96-well UV Microplate. The absorbance of samples (single samples, n=1) at 280 and 325 nm was measured in an absorbance-based plate reader, which was preheated to ambient temperature (typically 25° C.). The turbidity absorbance criterion for a peptide solubility of 1 mg/ml was an absorbance at 325 nm of 0.025 absorbance units (which is 5 to 6 times the standard deviation of 8 buffer samples in a plate). Solubility data for peptides of the invention are shown in Table 3, below.

TABLE 3

Solubility data.

| Cdp. | Acetate buffer pH 4 | Acetate buffer pH 5 | Histidine buffer pH 6 | Histidine buffer pH 7 | Phosphate buffer pH 6 | Phosphate buffer pH 7 | Phosphate buffer pH 7.5 |
|---|---|---|---|---|---|---|---|
| Teduglutide | II | II | II | SS | II | II | SS |
| 17 | II | II | SS | SS | SS | SS | SS |
| 18 | II | II | SS | SS | SS | SS | SS |
| 19 | II | II | SS | SS | SS | SS | SS |
| 20 | II | II | SS | SS | SS | SS | SS |
| 22 | II | II | SS | SS | SS | SS | SS |
| 23 | II | II | SS | SS | SS | SS | SS |
| 24 | II | II | SS | SS | SS | SS | SS |
| 25 | II | II | SS | SS | SS | SS | SS |
| 26 | SS | II | II | SS | II | SS | SS |
| 27 | II | II | SS | SS | SS | SS | SS |
| 28 | II | II | SS | SS | SS | SS | SS |

*SS indicates solubility ≥ 1 mg/ml
**II indicates solubility < 1 mg/ml

Example 4: Chemical Stability

Samples of each test peptide were dissolved in MILLIQ™ water, and the pH of the solution was adjusted to pH 6, 7, 7.5 or 9 using either HCl or NaOH. The final peptide concentration was 0.2 mg/ml. Samples were placed in glass vials and incubated at 40° C. The samples were analyzed by RP-HPLC on a C18 column with gradient elution using an acetonitrile/TFA/water eluent system. The area-percentage (area-%) of the main peak after incubation time T=t (relative to time T=0) was determined by UV spectroscopy at 220 nm.

The purity was first determined as follows:

Purity (area-%)=(area of main peak/total area of all peaks)×100.

The purity was then normalized between time points by setting purity at time 0 (T=0) to 100 for each pH value for a given peptide, as follows:

Normalized area-% at time $t$ ($T=t$)=[area-% ($T=t$)/area-% ($T=0$)]×100.

The chemical stability assessment results after 14-day incubation (in the form of normalized purity values) are summarized in Table 4.

TABLE 4

Chemical stability data.

| Compound | pH 6 normalized stability | pH 7 normalized stability |
|---|---|---|
| Teduglutide | | |
| A | C | B |
| B | A | A |
| 18 | A | A |
| 19 | A | A |
| 22 | A | B |
| 23 | A | B |
| 24 | B | A |
| 25 | | A |
| 26 | | A |
| 28 | | A |
| 29 | A | B |
| 30 | | A |
| 31 | A | A |
| 2 | A | A |
| 5 | A | A |
| 11 | | A |
| 14 | | A |
| 53 | | A |
| 42 | | A |
| 55 | | A |
| 58 | | A |
| 67 | | A |
| 68 | | A |
| 32 | | A |
| 33 | | A |
| 34 | | A |

Key: A—>90% normalised stability; B—>80% stability; C—<80% normalized stability.

Example 5: Effect on Fasting Glucose and Intestinal Weight in Normal Mice

Normal chow-fed C57BL/6J male mice were used. The mice were kept in standard housing conditions, light-, temperature-, and humidity-controlled room (12:12 h light-dark cycle, with lights on at 06.00-18.00 h; 20-22° C.; 50-80% relative humidity). Each dosing group consisted of 6 animals. Mice were dosed once daily with 100 nmol/kg with the test compounds or vehicle for 4 days via subcutaneous administration.

On day 0 mice were fasted and blood glucose levels measured after a single s.c. injection with peptides. Animals were sacrificed 24 hours after final dosing on day 3, and small intestinal wet weights were measured.

All test compounds (100 nmol/kg) reduced fasting blood glucose levels compared to vehicle group (Table 5).

All test compounds (100 nmol/kg) increased small intestine wet weight as compared to the vehicle-treated mice (Table 5).

TABLE 5

Effects on fasting blood glucose levels and small intestinal weight.

| Treatment | Fasting blood glucose (mM) | Small intestinal wet weight (g) |
|---|---|---|
| Vehicle | 8.99 | 0.80 |
| Cpd. 18 | 5.26 | 1.37 |
| Cpd. 48 | 5.08 | 1.41 |
| Cpd. 50 | 5.57 | 1.43 |
| Cpd. 5 | 4.60 | 1.35 |
| Cpd. 8 | 5.28 | 1.27 |
| Cpd. 9 | 4.98 | 1.11 |
| Cpd. 52 | 4.69 | 1.09 |

SEQUENCE LISTING

```
<160> NUMBER OF SEQ ID NOS: 540

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 33
<212> TYPE: PRT
<213> ORGANISM: Artificial Sequence
<220> FEATURE:
<223> OTHER INFORMATION: GLP-1/GLP-1 dual agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
<222> LOCATION: (5)..(5)
<223> OTHER INFORMATION: Xaa is T or S
<220> FEATURE:
<221> NAME/KEY: MISC_FEATURE
<222> LOCATION: (7)..(7)
<223> OTHER INFORMATION: Xaa is T or S
<220> FEATURE:
<221> NAME/KEY: MISC_FEATURE
<222> LOCATION: (8)..(8)
<223> OTHER INFORMATION: Xaa is S, E or D
<220> FEATURE:
<221> NAME/KEY: MISC_FEATURE
<222> LOCATION: (10)..(10)
<223> OTHER INFORMATION: Xaa is L, M, V or a residue of K, k (D-lys), R,
      Orn, Dap or Dab in which the side chain is conjugated to a
```

```
                          substituent
<220> FEATURE:
<221> NAME/KEY: MISC_FEATURE
<222> LOCATION: (11)..(11)
<223> OTHER INFORMATION: Xaa is A, N or S
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is G, E, A or a residue of K, k (D-lys), R,
      Orn, Dap or Dab in which the side chain is conjugated to a
      substituent
<220> FEATURE:
<221> NAME/KEY: MISC_FEATURE
<222> LOCATION: (17)..(17)
<223> OTHER INFORMATION: Xaa is Q, E, K, L or a residue of K, k (D-lys),
      R, Orn, Dap or Dab in which the side chain is conjugated to a
      substituent
<220> FEATURE:
<221> NAME/KEY: MISC_FEATURE
<222> LOCATION: (19)..(19)
<223> OTHER INFORMATION: Xaa is A, V or S
<220> FEATURE:
<221> NAME/KEY: MISC_FEATURE
<222> LOCATION: (20)..(20)
<223> OTHER INFORMATION: Xaa is R, K or a residue of K, k (D-lys), R,
      Orn, Dap or Dab in which the side chain is conjugated to a
      substituent
<220> FEATURE:
<221> NAME/KEY: MISC_FEATURE
<222> LOCATION: (21)..(21)
<223> OTHER INFORMATION: Xaa is D, L or E
<220> FEATURE:
<221> NAME/KEY: MISC_FEATURE
<222> LOCATION: (24)..(24)
<223> OTHER INFORMATION: Xaa is A, N or  S
<220> FEATURE:
<221> NAME/KEY: MISC_FEATURE
<222> LOCATION: (27)..(27)
<223> OTHER INFORMATION: Xaa is I, Q, K, H or Y
<220> FEATURE:
<221> NAME/KEY: MISC_FEATURE
<222> LOCATION: (28)..(28)
<223> OTHER INFORMATION: Xaa is Q, E, A, H, Y, L, K, R or S
<220> FEATURE:
<221> NAME/KEY: MISC_FEATURE
<222> LOCATION: (29)..(29)
<223> OTHER INFORMATION: Xaa is H, Y, K or Q
<220> FEATURE:
<221> NAME/KEY: MISC_FEATURE
<222> LOCATION: (33)..(33)
<223> OTHER INFORMATION: Xaa is D or  E

<400> SEQUENCE: 3

His Xaa Glu Gly Xaa Phe Xaa Xaa Glu Xaa Xaa Thr Ile Leu Xaa Xaa
1               5                   10                  15

Xaa Ala Xaa Xaa Xaa Phe Ile Xaa Trp Leu Xaa Xaa Xaa Lys Ile Thr
            20                  25                  30

Xaa

<210> SEQ ID NO 4
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (2)..(2)
<223> OTHER INFORMATION: Xaa is Aib or G
<220> FEATURE:
<221> NAME/KEY: MISC_FEATURE
```

```
<222> LOCATION: (5)..(5)
<223> OTHER INFORMATION: Xaa is T or S
<220> FEATURE:
<221> NAME/KEY: MISC_FEATURE
<222> LOCATION: (7)..(7)
<223> OTHER INFORMATION: Xaa is T or S
<220> FEATURE:
<221> NAME/KEY: MISC_FEATURE
<222> LOCATION: (16)..(16)
<223> OTHER INFORMATION: Xaa is G or a residue of K, k (D-lys), R, Orn,
      Dap or Dab in which the side chain is conjugated to a substituent
<220> FEATURE:
<221> NAME/KEY: MISC_FEATURE
<222> LOCATION: (17)..(17)
<223> OTHER INFORMATION: Xaa is Q, E, K, L or a residue of K, k (D-lys),
      R, Orn, Dap or Dab in which the side chain is conjugated to a
      substituent
<220> FEATURE:
<221> NAME/KEY: MISC_FEATURE
<222> LOCATION: (21)..(21)
<223> OTHER INFORMATION: Xaa is D or L
<220> FEATURE:
<221> NAME/KEY: MISC_FEATURE
<222> LOCATION: (28)..(28)
<223> OTHER INFORMATION: Xaa is Q, E, A, H, Y, L, K, R or S
<220> FEATURE:
<221> NAME/KEY: MISC_FEATURE
<222> LOCATION: (29)..(29)
<223> OTHER INFORMATION: Xaa is H, Y or Q

<400> SEQUENCE: 4

His Xaa Glu Gly Xaa Phe Xaa Ser Glu Leu Ala Thr Ile Leu Asp Xaa
1               5                   10                  15

Xaa Ala Ala Arg Xaa Phe Ile Ala Trp Leu Ile Xaa Xaa Lys Ile Thr
            20                  25                  30

Asp

<210> SEQ ID NO 5
<211> LENGTH: 33
<212> TYPE: PRT
<213> ORGANISM: Artificial Sequence
<220> FEATURE:
<223> OTHER INFORMATION: GLP-1/GLP-2 dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (5)..(5)
<223> OTHER INFORMATION: Xaa is T or S with at leasst one of Xaa at
      position 5 or 7 being a T
<220> FEATURE:
<221> NAME/KEY: MISC_FEATURE
<222> LOCATION: (7)..(7)
<223> OTHER INFORMATION: Xaa is T or S with at leasst one of Xaa at
      position 5 or 7 being a T
<220> FEATURE:
<221> NAME/KEY: MISC_FEATURE
<222> LOCATION: (10)..(10)
<223> OTHER INFORMATION: Xaa is L or a residue of K, k (D-lys), R, Orn,
      Dap or Dab in which the side chain is conjugated to a substituent
<220> FEATURE:
<221> NAME/KEY: MISC_FEATURE
<222> LOCATION: (16)..(16)
<223> OTHER INFORMATION: Xaa is G, E, A or a residue of K, k (D-lys), R,
      Orn, Dap or Dab in which the side chain is conjugated to a
      substituent
<220> FEATURE:
<221> NAME/KEY: MISC_FEATURE
<222> LOCATION: (17)..(17)
<223> OTHER INFORMATION: Xaa is Q, E, K, L or a residue of K, k (D-lys),
      R, Orn, Dap or Dab in which the side chain is conjugated to a
      substituent
<220> FEATURE:
```

```
<221> NAME/KEY: MISC_FEATURE
<222> LOCATION: (20)..(20)
<223> OTHER INFORMATION: Xaa is R or a residue of K, k (D-lys), R, Orn,
      Dap or Dab in which the side chain is conjugated to a substituent
<220> FEATURE:
<221> NAME/KEY: MISC_FEATURE
<222> LOCATION: (21)..(21)
<223> OTHER INFORMATION: Xaa is D or L
<220> FEATURE:
<221> NAME/KEY: MISC_FEATURE
<222> LOCATION: (28)..(28)
<223> OTHER INFORMATION: Xaa is E, A or Q
<220> FEATURE:
<221> NAME/KEY: MISC_FEATURE
<222> LOCATION: (29)..(29)
<223> OTHER INFORMATION: Xaa is H, Y or Q

<400> SEQUENCE: 5

His Xaa Glu Gly Xaa Phe Xaa Ser Glu Xaa Ala Thr Ile Leu Asp Xaa
1               5                   10                  15

Xaa Ala Ala Xaa Xaa Phe Ile Ala Trp Leu Ile Xaa Xaa Lys Ile Thr
            20                  25                  30

Asp

<210> SEQ ID NO 6
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (5)..(5)
<223> OTHER INFORMATION: Xaa is T or S with at least one of Xaa at
      position 5 or 7 being a T
<220> FEATURE:
<221> NAME/KEY: MISC_FEATURE
<222> LOCATION: (7)..(7)
<223> OTHER INFORMATION: Xaa is T or S with at least one of Xaa at
      position 5 or 7 being a T
<220> FEATURE:
<221> NAME/KEY: MISC_FEATURE
<222> LOCATION: (16)..(16)
<223> OTHER INFORMATION: Xaa is G or a residue of K, k (D-lys), R, Orn,
      Dap or Dab in which the side chain is conjugated to a substituent
<220> FEATURE:
<221> NAME/KEY: MISC_FEATURE
<222> LOCATION: (17)..(17)
<223> OTHER INFORMATION: Xaa is E, K, L or a residue of K, k (D-lys), R,
      Orn, Dap or Dab in which the side chain is conjugated to a
      substituent
<220> FEATURE:
<221> NAME/KEY: MISC_FEATURE
<222> LOCATION: (21)..(21)
<223> OTHER INFORMATION: Xaa is D or L
<220> FEATURE:
<221> NAME/KEY: MISC_FEATURE
<222> LOCATION: (28)..(28)
<223> OTHER INFORMATION: Xaa is E or A
<220> FEATURE:
<221> NAME/KEY: MISC_FEATURE
<222> LOCATION: (29)..(29)
<223> OTHER INFORMATION: Xaa is H, Y or Q

<400> SEQUENCE: 6

His Xaa Glu Gly Xaa Phe Xaa Ser Glu Leu Ala Thr Ile Leu Asp Xaa
1               5                   10                  15

Xaa Ala Ala Arg Xaa Phe Ile Ala Trp Leu Ile Xaa Xaa Lys Ile Thr
            20                  25                  30
```

Asp

```
<210> SEQ ID NO 7
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (5)..(5)
<223> OTHER INFORMATION: Xaa is T or S where at least one of Xaa at
      position 5 or 7 is a T
<220> FEATURE:
<221> NAME/KEY: MISC_FEATURE
<222> LOCATION: (7)..(7)
<223> OTHER INFORMATION: Xaa is T or S where at least one of Xaa at
      position 5 or 7 is a T
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent
<220> FEATURE:
<221> NAME/KEY: MISC_FEATURE
<222> LOCATION: (28)..(28)
<223> OTHER INFORMATION: Xaa is Q, E, A, H, Y, L, K, R or S, e.g. Q, E,
      A, H, Y or L
<220> FEATURE:
<221> NAME/KEY: MISC_FEATURE
<222> LOCATION: (29)..(29)
<223> OTHER INFORMATION: Xaa is H, Y or Q

<400> SEQUENCE: 7

His Xaa Glu Gly Xaa Phe Xaa Ser Glu Leu Ala Thr Ile Leu Asp Xaa
1               5                   10                  15

Gln Ala Ala Arg Asp Phe Ile Ala Trp Leu Ile Xaa Xaa Lys Ile Thr
            20                  25                  30

Asp

<210> SEQ ID NO 8
<211> LENGTH: 3
<212> TYPE: PRT
<213> ORGANISM: Artificial Sequence
<220> FEATURE:
<223> OTHER INFORMATION: GLP-1/GLP-2 Dual agonist peptide

<400> SEQUENCE: 8

Lys Glu Lys
1

<210> SEQ ID NO 9
<211> LENGTH: 6
<212> TYPE: PRT
<213> ORGANISM: Artificial Sequence
<220> FEATURE:
<223> OTHER INFORMATION: GLP-1/GLP-2 Dual agonist peptide

<400> SEQUENCE: 9

Glu Lys Glu Lys Glu Lys
1               5

<210> SEQ ID NO 10
<211> LENGTH: 6
<212> TYPE: PRT
```

```
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (1)..(1)
<223> OTHER INFORMATION: Xaa is D-lys
<220> FEATURE:
<221> NAME/KEY: MISC_FEATURE
<222> LOCATION: (2)..(2)
<223> OTHER INFORMATION: Xaa is D-lys
<220> FEATURE:
<221> NAME/KEY: MISC_FEATURE
<222> LOCATION: (3)..(3)
<223> OTHER INFORMATION: Xaa is D-lys
<220> FEATURE:
<221> NAME/KEY: MISC_FEATURE
<222> LOCATION: (4)..(4)
<223> OTHER INFORMATION: Xaa is D-lys
<220> FEATURE:
<221> NAME/KEY: MISC_FEATURE
<222> LOCATION: (5)..(5)
<223> OTHER INFORMATION: Xaa is D-lys
<220> FEATURE:
<221> NAME/KEY: MISC_FEATURE
<222> LOCATION: (6)..(6)
<223> OTHER INFORMATION: Xaa is D-lys

<400> SEQUENCE: 10

Xaa Xaa Glu Xaa Glu Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (2)..(2)
<223> OTHER INFORMATION: Xaa is D-lys
<220> FEATURE:
<221> NAME/KEY: MISC_FEATURE
<222> LOCATION: (4)..(4)
<223> OTHER INFORMATION: Xaa is D-lys
<220> FEATURE:
<221> NAME/KEY: MISC_FEATURE
<222> LOCATION: (6)..(6)
<223> OTHER INFORMATION: Xaa is D-lys

<400> SEQUENCE: 11

Glu Xaa Glu Xaa Glu Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: GLP-1/GLP-2 Dual agonist peptide

<400> SEQUENCE: 12

Ala Lys Ala Ala Glu Lys
1               5

<210> SEQ ID NO 13
<211> LENGTH: 6
<212> TYPE: PRT
<213> ORGANISM: Artificial Sequence
<220> FEATURE:
<223> OTHER INFORMATION: GLP-1/GLP-2 Dual agonist peptide
```

```
<400> SEQUENCE: 13

Ala Lys Glu Lys Glu Lys
1               5

<210> SEQ ID NO 14
<211> LENGTH: 6
<212> TYPE: PRT
<213> ORGANISM: Artificial Sequence
<220> FEATURE:
<223> OTHER INFORMATION: GLP-1/GLP-2 Dual agonist peptide

<400> SEQUENCE: 14

Ala Thr Ile Leu Glu Lys
1               5

<210> SEQ ID NO 15
<211> LENGTH: 3
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (3)..(3)
<223> OTHER INFORMATION: Xaa is a residue of K, k (D-lys), R, Orn, Dap
      or Dab in which the side chain is conjugated to a substituent

<400> SEQUENCE: 15

Lys Glu Xaa
1

<210> SEQ ID NO 16
<211> LENGTH: 6
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (6)..(6)
<223> OTHER INFORMATION: Xaa is a residue of K, k (D-lys), R, Orn, Dap
      or Dab in which the side chain is conjugated to a substituent

<400> SEQUENCE: 16

Glu Lys Glu Lys Glu Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (2)..(2)
<223> OTHER INFORMATION: Xaa is D-lys
<220> FEATURE:
<221> NAME/KEY: MISC_FEATURE
<222> LOCATION: (4)..(4)
<223> OTHER INFORMATION: Xaa is D-lys
<220> FEATURE:
<221> NAME/KEY: MISC_FEATURE
<222> LOCATION: (6)..(6)
<223> OTHER INFORMATION: Xaa is a residue of K, k (D-lys), R, Orn, Dap
      or Dab in which the side chain is conjugated to a substituent

<400> SEQUENCE: 17

Glu Xaa Glu Xaa Glu Xaa
1               5
```

```
<210> SEQ ID NO 18
<211> LENGTH: 6
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (6)..(6)
<223> OTHER INFORMATION: Xaa is a residue of K, k (D-lys), R, Orn, Dap
      or Dab in which the side chain is conjugated to a substituent

<400> SEQUENCE: 18

Ala Lys Ala Ala Glu Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (6)..(6)
<223> OTHER INFORMATION: Xaa is a residue of K, k (D-lys), R, Orn, Dap
      or Dab in which the side chain is conjugated to a substituent

<400> SEQUENCE: 19

Ala Lys Glu Lys Glu Xaa
1               5

<210> SEQ ID NO 20
<211> LENGTH: 6
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MISC_FEATURE
<222> LOCATION: (6)..(6)
<223> OTHER INFORMATION: xaa is a residue of K, k (D-lys), R, Orn, Dap
      or Dab in which the side chain is conjugated to a substituent

<400> SEQUENCE: 20

Ala Thr Ile Leu Glu Xaa
1               5

<210> SEQ ID NO 21
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 21

His Xaa Glu Gly Thr Phe Ser Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30
```

Asp

```
<210> SEQ ID NO 22
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 22

His Xaa Glu Gly Ser Phe Thr Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30
```

Asp

```
<210> SEQ ID NO 23
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 23

His Xaa Glu Gly Thr Phe Thr Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30
```

Asp

```
<210> SEQ ID NO 24
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 24

His Xaa Glu Gly Thr Phe Ser Ser Glu Leu Ala Thr Ile Leu Asp Xaa
1               5                   10                  15
```

Lys Ala Ala Arg Asp Phe Ile Ala Trp Leu Ile Glu His Lys Ile Thr
            20                  25                  30

Asp

<210> SEQ ID NO 25
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 25

His Xaa Glu Gly Ser Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 26
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 26

His Xaa Glu Gly Thr Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 27
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is a residue of K, k (D-lys), R, Orn, Dap
      or Dab in which the side chain is conjugated to a substituent

<400> SEQUENCE: 27

His Xaa Glu Gly Thr Phe Ser Ser Glu Leu Ala Thr Ile Leu Asp Gly

```
1               5                   10                  15

Xaa Ala Ala Arg Asp Phe Ile Ala Trp Leu Ile Glu His Lys Ile Thr
            20                  25                  30

Asp

<210> SEQ ID NO 28
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is a residue of K, k (D-lys), R, Orn, Dap
      or Dab in which the side chain is conjugated to a substituent

<400> SEQUENCE: 28

His Xaa Glu Gly Ser Phe Thr Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 29
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is a residue of K, k (D-lys), R, Orn, Dap
      or Dab in which the side chain is conjugated to a substituent

<400> SEQUENCE: 29

His Xaa Glu Gly Thr Phe Thr Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 30
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 30
```

```
His Xaa Glu Gly Thr Phe Ser Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 31
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 31

His Xaa Glu Gly Ser Phe Thr Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 32
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 32

His Xaa Glu Gly Thr Phe Thr Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 33
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent
```

<400> SEQUENCE: 33

His Xaa Glu Gly Thr Phe Ser Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 34
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 34

His Xaa Glu Gly Ser Phe Thr Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 35
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 35

His Xaa Glu Gly Thr Phe Thr Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 36
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)

```
<223> OTHER INFORMATION: Xaa is a residue of K, k (D-lys), R, Orn, Dap
      or Dab in which the side chain is conjugated to a substituent

<400> SEQUENCE: 36

His Xaa Glu Gly Thr Phe Thr Ser Glu Leu Ala Thr Ile Leu Asp Xaa
1               5                   10                  15

Glu Ala Ala Arg Leu Phe Ile Ala Trp Leu Ile Glu His Lys Ile Thr
            20                  25                  30

Asp

<210> SEQ ID NO 37
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 37

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 38
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 38

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 39
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
```

<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 39

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 40
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 40

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 41
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 41

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 42
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)

```
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 42

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 43
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 43

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 44
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 44

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 45
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 45

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 46
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 46

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile His His Lys Ile Thr
            20                  25                  30

Asp

<210> SEQ ID NO 47
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 47

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Tyr His Lys Ile Thr
            20                  25                  30

Asp

<210> SEQ ID NO 48
<211> LENGTH: 33
<212> TYPE: PRT
<213> ORGANISM: Artificial Sequence
<220> FEATURE:
```

<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
or Dab in which the side chain is conjugated to a substituent

<400> SEQUENCE: 48

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Leu His Lys Ile Thr
            20                  25                  30

Asp

<210> SEQ ID NO 49
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
or Dab in which the side chain is conjugated to a substituent

<400> SEQUENCE: 49

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Lys His Lys Ile Thr
            20                  25                  30

Asp

<210> SEQ ID NO 50
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
or Dab in which the side chain is conjugated to a substituent

<400> SEQUENCE: 50

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Arg His Lys Ile Thr
            20                  25                  30

Asp

<210> SEQ ID NO 51
<211> LENGTH: 33
<212> TYPE: PRT

```
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 51

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ser His Lys Ile Thr
            20                  25                  30

Asp

<210> SEQ ID NO 52
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 52

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Gln Gln His Lys Ile Thr
            20                  25                  30

Asp

<210> SEQ ID NO 53
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 53

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Tyr Gln His Lys Ile Thr
            20                  25                  30

Asp

<210> SEQ ID NO 54
```

```
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 54

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Lys Gln His Lys Ile Thr
            20                  25                  30

Asp

<210> SEQ ID NO 55
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 55

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Gln Lys Ile Thr
            20                  25                  30

Asp

<210> SEQ ID NO 56
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 56

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Tyr Lys Ile Thr
            20                  25                  30

Asp
```

```
<210> SEQ ID NO 57
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is a residue of K, k (D-lys), R, Orn, Dap
      or Dab in which the side chain is conjugated to a substituent

<400> SEQUENCE: 57

His Xaa Glu Gly Thr Phe Ser Ser Glu Leu Ser Thr Ile Leu Glu Xaa
1               5                   10                  15

Gln Ala Ser Arg Glu Phe Ile Ala Trp Leu Ile Ala Tyr Lys Ile Thr
            20                  25                  30

Glu

<210> SEQ ID NO 58
<211> LENGTH: 39
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(38)
<223> OTHER INFORMATION: Xaa at positions 34-38 is D-Lys
<220> FEATURE:
<221> NAME/KEY: MISC_FEATURE
<222> LOCATION: (39)..(39)
<223> OTHER INFORMATION: Xaa is a residue of K, k (D-lys), R, Orn, Dap
      or Dab in which the side chain is conjugated to a substituent

<400> SEQUENCE: 58

His Xaa Glu Gly Thr Phe Ser Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp Xaa Xaa Xaa Xaa Xaa Xaa
        35

<210> SEQ ID NO 59
<211> LENGTH: 39
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(38)
<223> OTHER INFORMATION: Xaa at positions 34-38 is D-Lys
<220> FEATURE:
<221> NAME/KEY: MISC_FEATURE
<222> LOCATION: (39)..(39)
<223> OTHER INFORMATION: Xaa is a residue of K, k (D-lys), R, Orn, Dap
      or Dab in which the side chain is conjugated to a substituent
```

<400> SEQUENCE: 59

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp Xaa Xaa Xaa Xaa Xaa Xaa
        35

<210> SEQ ID NO 60
<211> LENGTH: 39
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(38)
<223> OTHER INFORMATION: Xaa at positions 34-38 is D-Lys
<220> FEATURE:
<221> NAME/KEY: MISC_FEATURE
<222> LOCATION: (39)..(39)
<223> OTHER INFORMATION: Xaa is a residue of K, k (D-lys), R, Orn, Dap
      or Dab in which the side chain is conjugated to a substituent

<400> SEQUENCE: 60

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile Glu His Lys Ile Thr
            20                  25                  30

Asp Xaa Xaa Xaa Xaa Xaa Xaa
        35

<210> SEQ ID NO 61
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is a residue of K, k (D-lys), R, Orn, Dap
      or Dab in which the side chain is conjugated to a substituent

<400> SEQUENCE: 61

His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 62
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:

```
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is a residue of K, k (D-lys), R, Orn, Dap
      or Dab in which the side chain is conjugated to a substituent

<400> SEQUENCE: 62

His Xaa Glu Gly Ser Phe Thr Ser Glu Leu Ala Thr Ile Leu Glu Gly
1               5                   10                  15

Xaa Ala Ala Arg Asp Phe Ile Ala Trp Leu Ile Glu His Lys Ile Thr
            20                  25                  30

Asp

<210> SEQ ID NO 63
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is a residue of K, k (D-lys), R, Orn, Dap
      or Dab in which the side chain is conjugated to a substituent

<400> SEQUENCE: 63

His Xaa Glu Gly Ser Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 64
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is a residue of K, k (D-lys), R, Orn, Dap
      or Dab in which the side chain is conjugated to a substituent

<400> SEQUENCE: 64

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 65
<211> LENGTH: 33
<212> TYPE: PRT
<213> ORGANISM: Artificial Sequence
<220> FEATURE:
```

```
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is a residue of K, k (D-lys), R, Orn, Dap
      or Dab in which the side chain is conjugated to a substituent

<400> SEQUENCE: 65

His Xaa Glu Gly Thr Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 66
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is a residue of K, k (D-lys), R, Orn, Dap
      or Dab in which the side chain is conjugated to a substituent

<400> SEQUENCE: 66

His Xaa Glu Gly Ser Phe Thr Ser Glu Leu Ala Thr Ile Leu Asp Ala
1               5                   10                  15

Xaa Ala Ala Arg Asp Phe Ile Ala Trp Leu Ile Glu His Lys Ile Thr
            20                  25                  30

Asp

<210> SEQ ID NO 67
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is a residue of K, k (D-lys), R, Orn, Dap
      or Dab in which the side chain is conjugated to a substituent

<400> SEQUENCE: 67

His Xaa Glu Gly Ser Phe Thr Ser Glu Leu Ala Thr Ile Leu Asp Ala
1               5                   10                  15

Lys Ala Ala Xaa Asp Phe Ile Ala Trp Leu Ile Glu His Lys Ile Thr
            20                  25                  30

Asp

<210> SEQ ID NO 68
<211> LENGTH: 33
<212> TYPE: PRT
```

```
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 68

His Xaa Glu Gly Thr Phe Ser Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp

<210> SEQ ID NO 69
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 69

His Xaa Glu Gly Ser Phe Thr Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp

<210> SEQ ID NO 70
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 70

His Xaa Glu Gly Thr Phe Thr Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp

<210> SEQ ID NO 71
```

```
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 71

His Xaa Glu Gly Thr Phe Ser Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 72
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 72

His Xaa Glu Gly Ser Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 73
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 73

His Xaa Glu Gly Thr Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp
```

<210> SEQ ID NO 74
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa indicates an L-lysine residue in which the
      side chain is conjugated to the substituent Z1- or Z1Z2

<400> SEQUENCE: 74

His Xaa Glu Gly Thr Phe Ser Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 75
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa indicates an L-lysine residue in which the
      side chain is conjugated to the substituent Z1- or Z1Z2

<400> SEQUENCE: 75

His Xaa Glu Gly Ser Phe Thr Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 76
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa indicates an L-lysine residue in which the
      side chain is conjugated to the substituent Z1- or Z1Z2

<400> SEQUENCE: 76

His Xaa Glu Gly Thr Phe Thr Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 77
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: Xaa indicates an L-lysine residue in which the
      side chain is conjugated to the substituent Z1- or Z1Z2

<400> SEQUENCE: 77

His Xaa Glu Gly Thr Phe Ser Ser Glu Leu Ala Thr Ile Leu Asp Xaa
1               5                   10                  15
Leu Ala Ala Arg Asp Phe Ile Ala Trp Leu Ile Glu His Lys Ile Thr
            20                  25                  30
Asp

<210> SEQ ID NO 78
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 78

His Xaa Glu Gly Ser Phe Thr Ser Glu Leu Ala Thr Ile Leu Asp Xaa
1               5                   10                  15
Leu Ala Ala Arg Asp Phe Ile Ala Trp Leu Ile Glu His Lys Ile Thr
            20                  25                  30
Asp

<210> SEQ ID NO 79
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 79

His Xaa Glu Gly Thr Phe Thr Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 80
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 80

His Xaa Glu Gly Thr Phe Ser Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 81
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 81

His Xaa Glu Gly Ser Phe Thr Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 82
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

```
<400> SEQUENCE: 82

His Xaa Glu Gly Thr Phe Thr Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 83
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 83

His Xaa Glu Gly Thr Phe Thr Ser Glu Leu Ala Thr Ile Leu Asp Xaa
1               5                   10                  15

Glu Ala Ala Arg Leu Phe Ile Ala Trp Leu Ile Glu His Lys Ile Thr
            20                  25                  30

Asp

<210> SEQ ID NO 84
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 84

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 85
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
```

-continued side chain is conjugated to the substituent Z1- or Z1Z2

<400> SEQUENCE: 85

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 86
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 86

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 87
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 87

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 88
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE

```
<222> LOCATION: (16)..(16)
<223> OTHER INFORMATION: Xaa indicates an L-lysine residue in which the
      side chain is conjugated to the substituent Z1- or Z1Z2

<400> SEQUENCE: 88

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 89
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue respectively
      in which the side chain is conjugated to the substituent Z1- or
      Z1Z2
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 89

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 90
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 90

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 91
<211> LENGTH: 33
<212> TYPE: PRT
<213> ORGANISM: Artificial Sequence
```

```
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 91

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 92
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 92

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 93
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 93

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile His His Lys Ile Thr
            20                  25                  30

Asp

<210> SEQ ID NO 94
<211> LENGTH: 33
```

```
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 94

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Tyr His Lys Ile Thr
            20                  25                  30

Asp

<210> SEQ ID NO 95
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 95

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Leu His Lys Ile Thr
            20                  25                  30

Asp

<210> SEQ ID NO 96
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 96

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Lys His Lys Ile Thr
            20                  25                  30

Asp
```

```
<210> SEQ ID NO 97
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 97

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Arg His Lys Ile Thr
            20                  25                  30

Asp

<210> SEQ ID NO 98
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 98

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ser His Lys Ile Thr
            20                  25                  30

Asp

<210> SEQ ID NO 99
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 99

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Gln Gln His Lys Ile Thr
            20                  25                  30

Asp
```

```
<210> SEQ ID NO 100
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 100

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Tyr Gln His Lys Ile Thr
            20                  25                  30

Asp

<210> SEQ ID NO 101
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 101

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Lys Gln His Lys Ile Thr
            20                  25                  30

Asp

<210> SEQ ID NO 102
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 102

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Gln Lys Ile Thr
            20                  25                  30
```

Asp

```
<210> SEQ ID NO 103
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 103
```

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Tyr Lys Ile Thr
            20                  25                  30

Asp

```
<210> SEQ ID NO 104
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa indicates an L-lysine residue in which the
      side chain is conjugated to the substituent Z1- or Z1Z2

<400> SEQUENCE: 104
```

His Xaa Glu Gly Thr Phe Ser Ser Glu Leu Ser Thr Ile Leu Glu Xaa
1               5                   10                  15

Gln Ala Ser Arg Glu Phe Ile Ala Trp Leu Ile Ala Tyr Lys Ile Thr
            20                  25                  30

Glu

```
<210> SEQ ID NO 105
<211> LENGTH: 39
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(38)
<223> OTHER INFORMATION: Xaa at positions 34-38 is D-Lys
<220> FEATURE:
<221> NAME/KEY: MISC_FEATURE
<222> LOCATION: (39)..(39)
<223> OTHER INFORMATION: Xaa indicates an D-lysine residue in which the
      side chain is conjugated to the substituent Z1- or Z1Z2

<400> SEQUENCE: 105
```

-continued

```
His Xaa Glu Gly Thr Phe Ser Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp Xaa Xaa Xaa Xaa Xaa Xaa
        35
```

<210> SEQ ID NO 106
<211> LENGTH: 39
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(38)
<223> OTHER INFORMATION: Xaa at positions 34-38 is D-Lys
<220> FEATURE:
<221> NAME/KEY: MISC_FEATURE
<222> LOCATION: (39)..(39)
<223> OTHER INFORMATION: Xaa indicates an D-lysine residue in which the
      side chain is conjugated to the substituent Z1- or Z1Z2

<400> SEQUENCE: 106

```
His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp Xaa Xaa Xaa Xaa Xaa Xaa
        35
```

<210> SEQ ID NO 107
<211> LENGTH: 39
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(38)
<223> OTHER INFORMATION: Xaa at positions 34-38 is D-Lys
<220> FEATURE:
<221> NAME/KEY: MISC_FEATURE
<222> LOCATION: (39)..(39)
<223> OTHER INFORMATION: Xaa indicates an D-lysine residue in which the
      side chain is conjugated to the substituent Z1- or Z1Z2

<400> SEQUENCE: 107

```
His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile Glu His Lys Ile Thr
            20                  25                  30

Asp Xaa Xaa Xaa Xaa Xaa Xaa
        35
```

<210> SEQ ID NO 108
<211> LENGTH: 33
<212> TYPE: PRT
<213> ORGANISM: Artificial Sequence

```
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa indicates an L-lysine residue in which the
      side chain is conjugated to the substituent Z1- or Z1Z2

<400> SEQUENCE: 108

His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 109
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa indicates an L-lysine residue in which the
      side chain is conjugated to the substituent Z1- or Z1Z2

<400> SEQUENCE: 109

His Xaa Glu Gly Ser Phe Thr Ser Glu Leu Ala Thr Ile Leu Glu Gly
1               5                   10                  15

Xaa Ala Ala Arg Asp Phe Ile Ala Trp Leu Ile Glu His Lys Ile Thr
            20                  25                  30

Asp

<210> SEQ ID NO 110
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa indicates an L-lysine residue in which the
      side chain is conjugated to the substituent Z1- or Z1Z2

<400> SEQUENCE: 110

His Xaa Glu Gly Ser Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 111
<211> LENGTH: 33
```

```
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa indicates an L-lysine residue in which the
      side chain is conjugated to the substituent Z1- or Z1Z2

<400> SEQUENCE: 111

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 112
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa indicates an L-lysine residue in which the
      side chain is conjugated to the substituent Z1- or Z1Z2

<400> SEQUENCE: 112

His Xaa Glu Gly Thr Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 113
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa indicates an L-lysine residue in which the
      side chain is conjugated to the substituent Z1- or Z1Z2

<400> SEQUENCE: 113

His Xaa Glu Gly Ser Phe Thr Ser Glu Leu Ala Thr Ile Leu Asp Ala
1               5                   10                  15

Xaa Ala Ala Arg Asp Phe Ile Ala Trp Leu Ile Glu His Lys Ile Thr
            20                  25                  30

Asp
```

```
<210> SEQ ID NO 114
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa indicates an L-lysine residue in which the
      side chain is conjugated to the substituent Z1- or Z1Z2

<400> SEQUENCE: 114

His Xaa Glu Gly Ser Phe Thr Ser Glu Leu Ala Thr Ile Leu Asp Ala
1               5                   10                  15

Lys Ala Ala Xaa Asp Phe Ile Ala Trp Leu Ile Glu His Lys Ile Thr
            20                  25                  30

Asp

<210> SEQ ID NO 115
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 115

His Xaa Glu Gly Thr Phe Ser Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp

<210> SEQ ID NO 116
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 116

His Xaa Glu Gly Ser Phe Thr Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp
```

```
<210> SEQ ID NO 117
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 117

His Xaa Glu Gly Thr Phe Thr Ser Glu Leu Ala Thr Ile Leu Asp Xaa
 1               5                  10                  15

Glu Ala Ala Arg Asp Phe Ile Ala Trp Leu Ile Glu His Lys Ile Thr
            20                  25                  30

Asp

<210> SEQ ID NO 118
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 118

His Xaa Glu Gly Thr Phe Ser Ser Glu Leu Ala Thr Ile Leu Asp Xaa
 1               5                  10                  15

Lys Ala Ala Arg Asp Phe Ile Ala Trp Leu Ile Glu His Lys Ile Thr
            20                  25                  30

Asp

<210> SEQ ID NO 119
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 119

His Xaa Glu Gly Ser Phe Thr Ser Glu Leu Ala Thr Ile Leu Asp Xaa
 1               5                  10                  15

Lys Ala Ala Arg Asp Phe Ile Ala Trp Leu Ile Glu His Lys Ile Thr
            20                  25                  30

Asp

<210> SEQ ID NO 120
```

```
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 120

His Xaa Glu Gly Thr Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 121
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([17-carboxy-heptadecanoyl]-isoGlu)

<400> SEQUENCE: 121

His Xaa Glu Gly Thr Phe Ser Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 122
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([17-carboxy-heptadecanoyl]-isoGlu)

<400> SEQUENCE: 122

His Xaa Glu Gly Ser Phe Thr Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 123
<211> LENGTH: 33
```

-continued

```
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([17-carboxy-heptadecanoyl]-isoGlu)

<400> SEQUENCE: 123

His Xaa Glu Gly Thr Phe Thr Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 124
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 124

His Xaa Glu Gly Thr Phe Ser Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 125
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 125

His Xaa Glu Gly Ser Phe Thr Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 126
<211> LENGTH: 33
<212> TYPE: PRT
```

<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 126

His Xaa Glu Gly Thr Phe Thr Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 127
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 127

His Xaa Glu Gly Thr Phe Ser Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 128
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 128

His Xaa Glu Gly Ser Phe Thr Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 129
<211> LENGTH: 33
<212> TYPE: PRT
<213> ORGANISM: Artificial Sequence

```
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 129

His Xaa Glu Gly Thr Phe Thr Ser Glu Leu Ala Thr Ile Leu Asp Xaa
1               5                   10                  15

Leu Ala Ala Arg Asp Phe Ile Ala Trp Leu Ile Ala His Lys Ile Thr
            20                  25                  30

Asp

<210> SEQ ID NO 130
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 130

His Xaa Glu Gly Thr Phe Thr Ser Glu Leu Ala Thr Ile Leu Asp Xaa
1               5                   10                  15

Glu Ala Ala Arg Leu Phe Ile Ala Trp Leu Ile Glu His Lys Ile Thr
            20                  25                  30

Asp

<210> SEQ ID NO 131
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 131

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 132
<211> LENGTH: 33
<212> TYPE: PRT
<213> ORGANISM: Artificial Sequence
<220> FEATURE:
```

<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 132

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 133
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 133

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 134
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 134

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 135
<211> LENGTH: 33
<212> TYPE: PRT
<213> ORGANISM: Artificial Sequence
<220> FEATURE:
<223> OTHER INFORMATION: GLP-1/GLP-2 Dual agonist peptide

```
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 135

His Xaa Glu Gly Thr Phe Ser Ser Glu Leu Ala Thr Ile Leu Asp Xaa
 1               5                  10                  15

Gln Ala Ala Arg Asp Phe Ile Ala Trp Leu Ile Ala His Lys Ile Thr
            20                  25                  30

Asp

<210> SEQ ID NO 136
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 136

His Xaa Glu Gly Ser Phe Thr Ser Glu Leu Ala Thr Ile Leu Asp Xaa
 1               5                  10                  15

Gln Ala Ala Arg Asp Phe Ile Ala Trp Leu Ile Ala His Lys Ile Thr
            20                  25                  30

Asp

<210> SEQ ID NO 137
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 137

His Xaa Glu Gly Thr Phe Thr Ser Glu Leu Ala Thr Ile Leu Asp Xaa
 1               5                  10                  15

Gln Ala Ala Arg Asp Phe Ile Ala Trp Leu Ile Ala His Lys Ile Thr
            20                  25                  30

Asp

<210> SEQ ID NO 138
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 138

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 139
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 139

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 140
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 140

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile His His Lys Ile Thr
            20                  25                  30

Asp

<210> SEQ ID NO 141
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
```

<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 141

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Tyr His Lys Ile Thr
            20                  25                  30

Asp

<210> SEQ ID NO 142
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 142

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Leu His Lys Ile Thr
            20                  25                  30

Asp

<210> SEQ ID NO 143
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 143

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Lys His Lys Ile Thr
            20                  25                  30

Asp

<210> SEQ ID NO 144
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)

```
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)

<400> SEQUENCE: 144

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Arg His Lys Ile Thr
            20                  25                  30

Asp

<210> SEQ ID NO 145
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: misc
<222> LOCATION: (16)..(16)
<223> OTHER INFORMATION: Xaa is K([17-carboxy-heptadecanoyl]-isoGlu)

<400> SEQUENCE: 145

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ser His Lys Ile Thr
            20                  25                  30

Asp

<210> SEQ ID NO 146
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([Hexadecanoyl]- betaAla)

<400> SEQUENCE: 146

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Gln Gln His Lys Ile Thr
            20                  25                  30

Asp

<210> SEQ ID NO 147
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MISC_FEATURE
<222> LOCATION: (16)..(16)
<223> OTHER INFORMATION: Xaa is K([17-carboxy-heptadecanoyl]iso-Glu-
      Peg3)

<400> SEQUENCE: 147

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Tyr Gln His Lys Ile Thr
            20                  25                  30

Asp

<210> SEQ ID NO 148
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Glu-Peg3-
      Peg3)

<400> SEQUENCE: 148

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Lys Gln His Lys Ile Thr
            20                  25                  30

Asp

<210> SEQ ID NO 149
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Lys-Peg3-
      Peg3-Peg3)

<400> SEQUENCE: 149

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Gln Lys Ile Thr
            20                  25                  30

Asp

<210> SEQ ID NO 150
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
```

```
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K(Octadecanoyl)

<400> SEQUENCE: 150

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Tyr Lys Ile Thr
            20                  25                  30

Asp

<210> SEQ ID NO 151
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K(Hexadecanoyl-isoGlu)

<400> SEQUENCE: 151

His Xaa Glu Gly Thr Phe Ser Ser Glu Leu Ser Thr Ile Leu Glu Xaa
1               5                   10                  15

Gln Ala Ser Arg Glu Phe Ile Ala Trp Leu Ile Ala Tyr Lys Ile Thr
            20                  25                  30

Glu

<210> SEQ ID NO 152
<211> LENGTH: 40
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: MISC_FEATURE
<222> LOCATION: (35)..(39)
<223> OTHER INFORMATION: Xaa at positions 35-39 is D-Lys
<220> FEATURE:
<221> NAME/KEY: MISC_FEATURE
<222> LOCATION: (40)..(40)
<223> OTHER INFORMATION: Xaa is ([17-carboxy-Heptadecanoyl]-isoGlu)

<400> SEQUENCE: 152

His Xaa Glu Gly Thr Phe Ser Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp Xaa Xaa Xaa Xaa Xaa Xaa Xaa
        35                  40
```

-continued

```
<210> SEQ ID NO 153
<211> LENGTH: 40
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(39)
<223> OTHER INFORMATION: Xaa at positions 34-39 is D-Lys
<220> FEATURE:
<221> NAME/KEY: MISC_FEATURE
<222> LOCATION: (40)..(40)
<223> OTHER INFORMATION: Xaa is ([17-carboxy-Heptadecanoyl]-isoGlu)

<400> SEQUENCE: 153

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp Xaa Xaa Xaa Xaa Xaa Xaa Xaa
        35                  40

<210> SEQ ID NO 154
<211> LENGTH: 40
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(39)
<223> OTHER INFORMATION: Xaa at positions 34-39 is D-Lys
<220> FEATURE:
<221> NAME/KEY: MISC_FEATURE
<222> LOCATION: (40)..(40)
<223> OTHER INFORMATION: Xaa is ([17-carboxy-Heptadecanoyl]-isoGlu)

<400> SEQUENCE: 154

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile Glu His Lys Ile Thr
            20                  25                  30

Asp Xaa Xaa Xaa Xaa Xaa Xaa Xaa
        35                  40

<210> SEQ ID NO 155
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu)

<400> SEQUENCE: 155
```

```
His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp
```

<210> SEQ ID NO 156
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is K([19-carboxy-nonadecanoyl]iso-Glu-Peg3-Peg3)

<400> SEQUENCE: 156

```
His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp
```

<210> SEQ ID NO 157
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Glu-Peg3-Peg3)

<400> SEQUENCE: 157

```
His Xaa Glu Gly Ser Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp
```

<210> SEQ ID NO 158
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-carboxy-nonadecanoyl]iso-Glu-Peg3-Peg3)

<400> SEQUENCE: 158

His Xaa Glu Gly Ser Phe Thr Ser Glu Leu Ala Thr Ile Leu Glu Gly
1               5                   10                  15

Xaa Ala Ala Arg Asp Phe Ile Ala Trp Leu Ile Glu His Lys Ile Thr
            20                  25                  30

Asp

<210> SEQ ID NO 159
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-Peg3-
      Peg3)

<400> SEQUENCE: 159

His Xaa Glu Gly Ser Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 160
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-Peg3-
      Peg3)

<400> SEQUENCE: 160

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 161
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-Carboxy-heptadecanoyl]-isoGlu-KEK- Peg3)

<400> SEQUENCE: 161

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 162
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3)

<400> SEQUENCE: 162

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 163
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-Carboxy-heptadecanoyl]-isoGlu-KEK-
      Peg3)

<400> SEQUENCE: 163

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 164
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
     Peg3)

<400> SEQUENCE: 164

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 165
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK)

<400> SEQUENCE: 165

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 166
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
     Peg3)

<400> SEQUENCE: 166

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 167
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:

<221> NAME/KEY: MISC_FEATURE
<222> LOCATION: (10)..(10)
<223> OTHER INFORMATION: Xaa is K([19-Carboxy-nonadecanoyl]-isoGlu-KEK-
      Peg3)

<400> SEQUENCE: 167

His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 168
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is K([19-Carboxy-nonadecanoyl]-isoGlu-KEK-
      Peg3)

<400> SEQUENCE: 168

His Xaa Glu Gly Thr Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 169
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is K([19-carboxy-nonadecanoyl]iso-Glu-KEK-
      Peg3-Peg3)

<400> SEQUENCE: 169

His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 170
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)

```
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3)

<400> SEQUENCE: 170

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 171
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3)

<400> SEQUENCE: 171

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 172
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3)

<400> SEQUENCE: 172

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 173
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3)

<400> SEQUENCE: 173

His Xaa Glu Gly Ser Phe Thr Ser Glu Leu Ala Thr Ile Leu Asp Xaa
 1               5                  10                  15

Lys Ala Ala Arg Asp Phe Ile Ala Trp Leu Ile Glu His Lys Ile Thr
            20                  25                  30

Asp

<210> SEQ ID NO 174
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Glu-KEK-
      Peg3-Peg3)

<400> SEQUENCE: 174

His Xaa Glu Gly Ser Phe Thr Ser Glu Leu Ala Thr Ile Leu Asp Xaa
 1               5                  10                  15

Gln Ala Ala Arg Asp Phe Ile Ala Trp Leu Ile Glu His Lys Ile Thr
            20                  25                  30

Asp

<210> SEQ ID NO 175
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-Carboxy-nonadecanoyl]-isoGlu-KEK-
      Peg3)

<400> SEQUENCE: 175

His Xaa Glu Gly Ser Phe Thr Ser Glu Leu Ala Thr Ile Leu Glu Gly
 1               5                  10                  15

Xaa Ala Ala Arg Asp Phe Ile Ala Trp Leu Ile Glu His Lys Ile Thr
            20                  25                  30

Asp

<210> SEQ ID NO 176
<211> LENGTH: 33
<212> TYPE: PRT
<213> ORGANISM: Artificial Sequence
<220> FEATURE:
```

<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-Carboxy-nonadecanoyl]-isoGlu-KEK-Peg3)

<400> SEQUENCE: 176

His Xaa Glu Gly Ser Phe Thr Ser Glu Leu Ala Thr Ile Leu Asp Ala
1               5                   10                  15
Xaa Ala Ala Arg Asp Phe Ile Ala Trp Leu Ile Glu His Lys Ile Thr
            20                  25                  30
Asp

<210> SEQ ID NO 177
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-carboxy-nonadecanoyl]iso-Glu-KEK-Peg3-Peg3)

<400> SEQUENCE: 177

His Xaa Glu Gly Ser Phe Thr Ser Glu Leu Ala Thr Ile Leu Asp Ala
1               5                   10                  15
Xaa Ala Ala Arg Asp Phe Ile Ala Trp Leu Ile Glu His Lys Ile Thr
            20                  25                  30
Asp

<210> SEQ ID NO 178
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-Carboxy-nonadecanoyl]-isoGlu-KEK-Peg3)

<400> SEQUENCE: 178

His Xaa Glu Gly Ser Phe Thr Ser Glu Leu Ala Thr Ile Leu Asp Glu
1               5                   10                  15
Gln Ala Ala Xaa Asp Phe Ile Ala Trp Leu Ile Glu His Lys Ile Thr
            20                  25                  30
Asp

<210> SEQ ID NO 179
<211> LENGTH: 33
<212> TYPE: PRT

```
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-Carboxy-nonadecanoyl]-isoGlu-KEK-
      Peg3)

<400> SEQUENCE: 179

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 180
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-KEK-
      Peg3-Peg3)

<400> SEQUENCE: 180

His Xaa Glu Gly Ser Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 181
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-KEK-
      Peg3-Peg3)

<400> SEQUENCE: 181

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 182
```

```
<211> LENGTH: 33
<212> TYPE: PRT
<213> ORGANISM: Artificial Sequence
<220> FEATURE:
<223> OTHER INFORMATION: GLP-1/GLP-2 Dual agonist peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-Carboxy-nonadecanoyl]-isoGlu-KEK-
      Peg3)

<400> SEQUENCE: 182

His Xaa Glu Gly Ser Phe Thr Ser Glu Leu Ala Thr Ile Leu Asp Ala
1               5                   10                  15

Lys Ala Ala Xaa Asp Phe Ile Ala Trp Leu Ile Glu His Lys Ile Thr
            20                  25                  30

Asp

<210> SEQ ID NO 183
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 183

His Xaa Glu Gly Thr Phe Ser Ser Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp

<210> SEQ ID NO 184
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
```

<221> NAME/KEY: MOD_RES
<222> LOCATION: (33)..(33)
<223> OTHER INFORMATION: Hydroxyl

<400> SEQUENCE: 184

His Xaa Glu Gly Ser Phe Thr Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp

<210> SEQ ID NO 185
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 185

His Xaa Glu Gly Thr Phe Thr Ser Glu Leu Ala Thr Ile Leu Asp Xaa
1               5                   10                  15

Glu Ala Ala Arg Asp Phe Ile Ala Trp Leu Ile Glu His Lys Ile Thr
            20                  25                  30

Asp

<210> SEQ ID NO 186
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 186

His Xaa Glu Gly Thr Phe Ser Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 187
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 187

His Xaa Glu Gly Ser Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 188
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 188

His Xaa Glu Gly Thr Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 189
<211> LENGTH: 33
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 189

His Xaa Glu Gly Thr Phe Ser Ser Glu Leu Ala Thr Ile Leu Asp Gly
 1               5                  10                  15

Xaa Ala Ala Arg Asp Phe Ile Ala Trp Leu Ile Glu His Lys Ile Thr
                20                  25                  30

Asp

<210> SEQ ID NO 190
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 190

His Xaa Glu Gly Ser Phe Thr Ser Glu Leu Ala Thr Ile Leu Asp Gly
 1               5                  10                  15

Xaa Ala Ala Arg Asp Phe Ile Ala Trp Leu Ile Glu His Lys Ile Thr
                20                  25                  30

Asp

<210> SEQ ID NO 191
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa  is K([17-carboxy-heptadecanoyl]-isoGlu)
```

```
<220> FEATURE:
<221> NAME/KEY: MOD_RES
<222> LOCATION: (33)..(33)
<223> OTHER INFORMATION: Hydroxyl

<400> SEQUENCE: 191

His Xaa Glu Gly Thr Phe Thr Ser Glu Leu Ala Thr Ile Leu Asp Gly
1               5                   10                  15

Xaa Ala Ala Arg Asp Phe Ile Ala Trp Leu Ile Glu His Lys Ile Thr
            20                  25                  30

Asp

<210> SEQ ID NO 192
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 192

His Xaa Glu Gly Thr Phe Ser Ser Glu Leu Ala Thr Ile Leu Asp Xaa
1               5                   10                  15

Leu Ala Ala Arg Asp Phe Ile Ala Trp Leu Ile Glu His Lys Ile Thr
            20                  25                  30

Asp

<210> SEQ ID NO 193
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 193

His Xaa Glu Gly Ser Phe Thr Ser Glu Leu Ala Thr Ile Leu Asp Xaa
1               5                   10                  15

Leu Ala Ala Arg Asp Phe Ile Ala Trp Leu Ile Glu His Lys Ile Thr
```

Asp

<210> SEQ ID NO 194
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 194

His Xaa Glu Gly Thr Phe Thr Ser Glu Leu Ala Thr Ile Leu Asp Xaa
1               5                   10                  15
Leu Ala Ala Arg Asp Phe Ile Ala Trp Leu Ile Glu His Lys Ile Thr
            20                  25                  30
Asp

<210> SEQ ID NO 195
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 195

His Xaa Glu Gly Thr Phe Ser Ser Glu Leu Ala Thr Ile Leu Asp Xaa
1               5                   10                  15
Leu Ala Ala Arg Asp Phe Ile Ala Trp Leu Ile Ala His Lys Ile Thr
            20                  25                  30
Asp

<210> SEQ ID NO 196
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 196

His Xaa Glu Gly Ser Phe Thr Ser Glu Leu Ala Thr Ile Leu Asp Xaa
 1               5                  10                  15

Leu Ala Ala Arg Asp Phe Ile Ala Trp Leu Ile Ala His Lys Ile Thr
            20                  25                  30

Asp

<210> SEQ ID NO 197
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 197

His Xaa Glu Gly Thr Phe Thr Ser Glu Leu Ala Thr Ile Leu Asp Xaa
 1               5                  10                  15

Leu Ala Ala Arg Asp Phe Ile Ala Trp Leu Ile Ala His Lys Ile Thr
            20                  25                  30

Asp

<210> SEQ ID NO 198
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)

<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 198

His Xaa Glu Gly Thr Phe Thr Ser Glu Leu Ala Thr Ile Leu Asp Xaa
1               5                   10                  15

Glu Ala Ala Arg Leu Phe Ile Ala Trp Leu Ile Glu His Lys Ile Thr
            20                  25                  30

Asp

<210> SEQ ID NO 199
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 199

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 200
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 200

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 201
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 201

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 202
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 202

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 203
<211> LENGTH: 33
<212> TYPE: PRT
<213> ORGANISM: Artificial Sequence
<220> FEATURE:

<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 203

His Xaa Glu Gly Thr Phe Ser Ser Glu Leu Ala Thr Ile Leu Asp Xaa
1               5                   10                  15
Gln Ala Ala Arg Asp Phe Ile Ala Trp Leu Ile Ala His Lys Ile Thr
            20                  25                  30
Asp

<210> SEQ ID NO 204
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 204

His Xaa Glu Gly Ser Phe Thr Ser Glu Leu Ala Thr Ile Leu Asp Xaa
1               5                   10                  15
Gln Ala Ala Arg Asp Phe Ile Ala Trp Leu Ile Ala His Lys Ile Thr
            20                  25                  30
Asp

<210> SEQ ID NO 205
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 205

His Xaa Glu Gly Thr Phe Thr Ser Glu Leu Ala Thr Ile Leu Asp Xaa
1               5                   10                  15
Gln Ala Ala Arg Asp Phe Ile Ala Trp Leu Ile Ala His Lys Ile Thr
            20                  25                  30
Asp

<210> SEQ ID NO 206
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 206

His Xaa Glu Gly Ser Phe Thr Ser Glu Leu Ala Thr Ile Leu Asp Xaa
1               5                   10                  15
Gln Ala Ala Arg Asp Phe Ile Ala Trp Leu Ile Glu His Lys Ile Thr
            20                  25                  30
Asp

<210> SEQ ID NO 207
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 207

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 208
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 208

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile His His Lys Ile Thr
            20                  25                  30

Asp

<210> SEQ ID NO 209
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 209

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Tyr His Lys Ile Thr
            20                  25                  30

Asp

<210> SEQ ID NO 210
<211> LENGTH: 33
<212> TYPE: PRT
<213> ORGANISM: Artificial Sequence

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 210

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Leu His Lys Ile Thr
            20                  25                  30

Asp

<210> SEQ ID NO 211
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 211

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Lys His Lys Ile Thr
            20                  25                  30

Asp

<210> SEQ ID NO 212
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
```

<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 212

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Arg His Lys Ile Thr
            20                  25                  30

Asp

<210> SEQ ID NO 213
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 213

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ser His Lys Ile Thr
            20                  25                  30

Asp

<210> SEQ ID NO 214
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([Hexadecanoyl]- betaAla), where
      betaAla is betaAla is 3-Aminopropanoyl
<220> FEATURE:
<221> NAME/KEY: MOD_RES
<222> LOCATION: (33)..(33)
<223> OTHER INFORMATION: Hydroxyl

<400> SEQUENCE: 214

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Gln Gln His Lys Ile Thr
            20                  25                  30

Asp

<210> SEQ ID NO 215
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]iso-Glu-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 215

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Tyr Gln His Lys Ile Thr
            20                  25                  30

Asp

<210> SEQ ID NO 216
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Glu-Peg3-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 216

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Lys Gln His Lys Ile Thr
            20                  25                  30

Asp

-continued

```
<210> SEQ ID NO 217
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Lys-Peg3-
      Peg3-Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 217

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Gln Lys Ile Thr
            20                  25                  30

Asp

<210> SEQ ID NO 218
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K(Octadecanoyl)
<220> FEATURE:
<221> NAME/KEY: MOD_RES
<222> LOCATION: (33)..(33)
<223> OTHER INFORMATION: Hydroxyl

<400> SEQUENCE: 218

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln Tyr Lys Ile Thr
            20                  25                  30

Asp

<210> SEQ ID NO 219
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K(Hexadecanoyl-isoGlu)
<220> FEATURE:
<221> NAME/KEY: MOD_RES
<222> LOCATION: (33)..(33)
<223> OTHER INFORMATION: Hydroxyl

<400> SEQUENCE: 219

His Xaa Glu Gly Thr Phe Ser Ser Glu Leu Ser Thr Ile Leu Glu Xaa
1               5                   10                  15

Gln Ala Ser Arg Glu Phe Ile Ala Trp Leu Ile Ala Tyr Lys Ile Thr
                20                  25                  30

Glu

<210> SEQ ID NO 220
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(34)
<223> OTHER INFORMATION: Xaa can be any naturally occurring amino acid
<220> FEATURE:
<221> NAME/KEY: MISC_FEATURE
<222> LOCATION: (35)..(39)
<223> OTHER INFORMATION: Xaa at positions 35-39 is D-Lys
<220> FEATURE:
<221> NAME/KEY: MISC_FEATURE
<222> LOCATION: (40)..(40)
<223> OTHER INFORMATION: Xaa is ([17-carboxy-Heptadecanoyl]-isoGlu)
<220> FEATURE:
<221> NAME/KEY: MOD_RES
<222> LOCATION: (40)..(40)
<223> OTHER INFORMATION: Amine

<400> SEQUENCE: 220

His Xaa Glu Gly Thr Phe Ser Ser Glu Leu Ala Thr Ile Leu Asp Glu
1               5                   10                  15

Gln Ala Ala Arg Asp Phe Ile Ala Trp Leu Ile Ala His Lys Ile Thr
                20                  25                  30

Asp Xaa Xaa Xaa Xaa Xaa Xaa Xaa
                35                  40

<210> SEQ ID NO 221
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
```

```
<222> LOCATION: (2)..(2)
<223> OTHER INFORMATION: Aib
<220> FEATURE:
<221> NAME/KEY: MISC_FEATURE
<222> LOCATION: (34)..(39)
<223> OTHER INFORMATION: Xaa at positions 34-39 is D-Lys
<220> FEATURE:
<221> NAME/KEY: MISC_FEATURE
<222> LOCATION: (40)..(40)
<223> OTHER INFORMATION: Xaa is ([17-carboxy-Heptadecanoyl]-isoGlu)
<220> FEATURE:
<221> NAME/KEY: MOD_RES
<222> LOCATION: (40)..(40)
<223> OTHER INFORMATION: Amine

<400> SEQUENCE: 221

His Xaa Glu Gly Thr Phe Thr Ser Glu Leu Ala Thr Ile Leu Asp Glu
1               5                   10                  15

Gln Ala Ala Arg Asp Phe Ile Ala Trp Leu Ile Ala His Lys Ile Thr
            20                  25                  30

Asp Xaa Xaa Xaa Xaa Xaa Xaa Xaa
        35                  40

<210> SEQ ID NO 222
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (34)..(39)
<223> OTHER INFORMATION: Xaa at positions 34-39 is D-Lys
<220> FEATURE:
<221> NAME/KEY: MISC_FEATURE
<222> LOCATION: (40)..(40)
<223> OTHER INFORMATION: Xaa is ([17-carboxy-Heptadecanoyl]-isoGlu)
<220> FEATURE:
<221> NAME/KEY: MOD_RES
<222> LOCATION: (40)..(40)
<223> OTHER INFORMATION: Amine

<400> SEQUENCE: 222

His Xaa Glu Gly Ser Phe Thr Ser Glu Leu Ala Thr Ile Leu Asp Glu
1               5                   10                  15

Gln Ala Ala Arg Asp Phe Ile Ala Trp Leu Ile Glu His Lys Ile Thr
            20                  25                  30

Asp Xaa Xaa Xaa Xaa Xaa Xaa Xaa
        35                  40

<210> SEQ ID NO 223
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
```

```
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu)
<220> FEATURE:
<221> NAME/KEY: MOD_RES
<222> LOCATION: (33)..(33)
<223> OTHER INFORMATION: Hydroxyl

<400> SEQUENCE: 223

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 224
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is K([19-carboxy-nonadecanoyl]iso-Glu-Peg3-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 224

His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 225
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Glu-Peg3-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl
```

```
<400> SEQUENCE: 225

His Xaa Glu Gly Ser Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
                20                  25                  30

Asp

<210> SEQ ID NO 226
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-carboxy-nonadecanoyl]iso-Glu-Peg3-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 226

His Xaa Glu Gly Ser Phe Thr Ser Glu Leu Ala Thr Ile Leu Glu Gly
1               5                   10                  15

Xaa Ala Ala Arg Asp Phe Ile Ala Trp Leu Ile Glu His Lys Ile Thr
                20                  25                  30

Asp

<210> SEQ ID NO 227
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-Peg3-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 227

His Xaa Glu Gly Ser Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
                20                  25                  30
```

Asp

```
<210> SEQ ID NO 228
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-Peg3-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 228

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30
```

Asp

```
<210> SEQ ID NO 229
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-Carboxy-heptadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 229

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30
```

Asp

```
<210> SEQ ID NO 230
<211> LENGTH: 33
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 230

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 231
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-Carboxy-heptadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 231

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 232
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
```

<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 232

His Xaa Glu Gly Thr Phe Ser Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 233
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK)
<220> FEATURE:
<221> NAME/KEY: MOD_RES
<222> LOCATION: (33)..(33)
<223> OTHER INFORMATION: Hydroxyl

<400> SEQUENCE: 233

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 234
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 234

```
His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
            20                  25                  30

Asp

<210> SEQ ID NO 235
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 235

His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 236
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 236

His Xaa Glu Gly Thr Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp
```

```
<210> SEQ ID NO 237
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (10)..(10)
<223> OTHER INFORMATION: Xaa is K([19-carboxy-nonadecanoyl]iso-Glu-KEK-
     Peg3-Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 237

His Xaa Glu Gly Ser Phe Thr Ser Glu Xaa Ala Thr Ile Leu Asp Glu
1               5                   10                  15

Gln Ala Ala Arg Asp Phe Ile Ala Trp Leu Ile Glu His Lys Ile Thr
            20                  25                  30

Asp

<210> SEQ ID NO 238
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
     Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 238

His Xaa Glu Gly Thr Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 239
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 239

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 240
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 240

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Ala His Lys Ile Thr
            20                  25                  30

Asp

<210> SEQ ID NO 241
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
```

<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 241

His Xaa Glu Gly Ser Phe Thr Ser Glu Leu Ala Thr Ile Leu Asp Xaa
1               5                   10                  15

Lys Ala Ala Arg Asp Phe Ile Ala Trp Leu Ile Glu His Lys Ile Thr
            20                  25                  30

Asp

<210> SEQ ID NO 242
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([19-carboxy-nonadecanoyl]iso-Glu-KEK-
      Peg3-Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 242

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Glu His Lys Ile Thr
            20                  25                  30

Asp

<210> SEQ ID NO 243
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 243

His Xaa Glu Gly Ser Phe Thr Ser Glu Leu Ala Thr Ile Leu Glu Gly
1               5                   10                  15

Xaa Ala Ala Arg Asp Phe Ile Ala Trp Leu Ile Glu His Lys Ile Thr
            20                  25                  30

Asp

<210> SEQ ID NO 244
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 244

His Xaa Glu Gly Ser Phe Thr Ser Glu Leu Ala Thr Ile Leu Asp Ala
1               5                   10                  15

Xaa Ala Ala Arg Asp Phe Ile Ala Trp Leu Ile Glu His Lys Ile Thr
            20                  25                  30

Asp

<210> SEQ ID NO 245
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (17)..(17)
<223> OTHER INFORMATION: Xaa is K([19-carboxy-nonadecanoyl]iso-Glu-KEK-
      Peg3-Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 245

His Xaa Glu Gly Ser Phe Thr Ser Glu Leu Ala Thr Ile Leu Asp Ala
1               5                   10                  15

Xaa Ala Ala Arg Asp Phe Ile Ala Trp Leu Ile Glu His Lys Ile Thr
            20                  25                  30

Asp

```
<210> SEQ ID NO 246
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 246

His Xaa Glu Gly Ser Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 247
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-Carboxy-nonadecanoyl]-isoGlu-KEK-
      Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 247

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 248
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
```

```
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-KEK-
      Peg3-Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 248

His Xaa Glu Gly Ser Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 249
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Xaa is K([19-carboxy-nonadecanoyl]iso-Glu-KEK-
      Peg3-Peg3), where Peg3 is 8-amino-3,6-dioxaoctanoyl group
<220> FEATURE:
<221> NAME/KEY: MOD_RES
<222> LOCATION: (33)..(33)
<223> OTHER INFORMATION: Hydroxyl

<400> SEQUENCE: 249

His Xaa Glu Gly Thr Phe Thr Ser Glu Leu Ala Thr Ile Leu Asp Glu
1               5                   10                  15

Gln Ala Ala Xaa Asp Phe Ile Ala Trp Leu Ile Glu His Lys Ile Thr
            20                  25                  30

Asp

<210> SEQ ID NO 250
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (20)..(20)
<220> FEATURE:
```

```
<221> NAME/KEY: MOD_RES
<222> LOCATION: (33)..(33)
<223> OTHER INFORMATION: Hydroxyl

<400> SEQUENCE: 250

His Xaa Glu Gly Ser Phe Thr Ser Glu Leu Ala Thr Ile Leu Asp Ala
1               5                   10                  15

Lys Ala Ala Xaa Asp Phe Ile Ala Trp Leu Ile Glu His Lys Ile Thr
            20                  25                  30

Asp

<210> SEQ ID NO 251
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hexadecanoyl

<400> SEQUENCE: 251

Lys Glu Lys
1

<210> SEQ ID NO 252
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Octadecanoyl

<400> SEQUENCE: 252

Lys Glu Lys
1

<210> SEQ ID NO 253
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Eicosanoyl

<400> SEQUENCE: 253

Lys Glu Lys
1

<210> SEQ ID NO 254
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Tetradecanoyl

<400> SEQUENCE: 254
```

Lys Glu Lys
1

<210> SEQ ID NO 255
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Dodecanoyl

<400> SEQUENCE: 255

Lys Glu Lys
1

<210> SEQ ID NO 256
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 256

Lys Glu Lys
1

<210> SEQ ID NO 257
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 257

Lys Glu Lys
1

<210> SEQ ID NO 258
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl

```
                          group

<400> SEQUENCE: 258

Lys Glu Lys
1

<210> SEQ ID NO 259
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 259

Lys Glu Lys
1

<210> SEQ ID NO 260
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 260

Lys Glu Lys
1

<210> SEQ ID NO 261
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 261

Lys Glu Lys
1

<210> SEQ ID NO 262
<211> LENGTH: 3
<212> TYPE: PRT
<213> ORGANISM: Artificial Sequence
<220> FEATURE:
```

<223> OTHER INFORMATION: Synthetic Construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 262

Lys Glu Lys
1

<210> SEQ ID NO 263
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 263

Lys Glu Lys
1

<210> SEQ ID NO 264
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 264

Lys Glu Lys
1

<210> SEQ ID NO 265
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 265

Lys Glu Lys
1

<210> SEQ ID NO 266
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 266

Lys Glu Lys
1

<210> SEQ ID NO 267
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 267

Lys Glu Lys
1

<210> SEQ ID NO 268
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 268

Lys Glu Lys
1

<210> SEQ ID NO 269
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)

```
<223> OTHER INFORMATION: Octadecanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 269

Lys Glu Lys
1

<210> SEQ ID NO 270
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 270

Lys Glu Lys
1

<210> SEQ ID NO 271
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-isoGlu
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 271

Lys Glu Lys
1

<210> SEQ ID NO 272
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-isoGlu
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 272

Lys Glu Lys
1
```

-continued

```
<210> SEQ ID NO 273
<211> LENGTH: 3
<212> TYPE: PRT
<213> ORGANISM: Artificial Sequence
<220> FEATURE:
<223> OTHER INFORMATION: Synthetic Contruct
<220> FEATURE:
<221> NAME/KEY: MOD_RES
<222> LOCATION: (1)..(1)
<223> OTHER INFORMATION: [Hexadecanoyl]-isoGlu
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 273

Lys Glu Lys
1

<210> SEQ ID NO 274
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-isoGlu
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 274

Lys Glu Lys
1

<210> SEQ ID NO 275
<211> LENGTH: 3
<212> TYPE: PRT
<213> ORGANISM: Artificial Sequence
<220> FEATURE:
<223> OTHER INFORMATION: Synthetic Costruct
<220> FEATURE:
<221> NAME/KEY: MOD_RES
<222> LOCATION: (1)..(1)
<223> OTHER INFORMATION: [Eicosanoyl]-isoGlu
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 275

Lys Glu Lys
1

<210> SEQ ID NO 276
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-[4-aminobutanoyl]
<220> FEATURE:
<221> NAME/KEY: MOD_RES
<222> LOCATION: (3)..(3)
```

<223> OTHER INFORMATION: Peg3, where Peg3 is 8-amino-3,6-dioxaoctanoyl
      group

<400> SEQUENCE: 276

Lys Glu Lys
1

<210> SEQ ID NO 277
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-[4-aminobutanoyl]
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 277

Lys Glu Lys
1

<210> SEQ ID NO 278
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-[4-aminobutanoyl]
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 278

Lys Glu Lys
1

<210> SEQ ID NO 279
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-[4-aminobutanoyl]
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 279

Lys Glu Lys
1

<210> SEQ ID NO 280
<211> LENGTH: 3
<212> TYPE: PRT
<213> ORGANISM: Artificial Sequence

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-[4-aminobutanoyl]
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 280

Lys Glu Lys
1

<210> SEQ ID NO 281
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-isoLys
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 281

Lys Glu Lys
1

<210> SEQ ID NO 282
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-isoLys
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 282

Lys Glu Lys
1

<210> SEQ ID NO 283
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-isoLys
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 283
```

Lys Glu Lys
1

<210> SEQ ID NO 284
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-isoLys
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 284

Lys Glu Lys
1

<210> SEQ ID NO 285
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-isoLys
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 285

Lys Glu Lys
1

<210> SEQ ID NO 286
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-Ala
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 286

Lys Glu Lys
1

<210> SEQ ID NO 287
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES

```
<222> LOCATION: (1)..(1)
<223> OTHER INFORMATION: [Tetradecanoyl]-Ala
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 287

Lys Glu Lys
1

<210> SEQ ID NO 288
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-Ala
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 288

Lys Glu Lys
1

<210> SEQ ID NO 289
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-Ala
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 289

Lys Glu Lys
1

<210> SEQ ID NO 290
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-Ala
<220> FEATURE:
<221> NAME/KEY: MOD_RES
<222> LOCATION: (3)..(3)
<223> OTHER INFORMATION: Peg3, where Peg3 is 8-amino-3,6-dioxaoctanoyl
      group

<400> SEQUENCE: 290

Lys Glu Lys
1
```

```
<210> SEQ ID NO 291
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-isoGlu
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 291

Lys Glu Lys
1

<210> SEQ ID NO 292
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-isoGlu
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 292

Lys Glu Lys
1

<210> SEQ ID NO 293
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-isoGlu
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 293

Lys Glu Lys
1

<210> SEQ ID NO 294
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-isoGlu
<220> FEATURE:
<221> NAME/KEY: MOD_RES
```

```
<222> LOCATION: (3)..(3)
<223> OTHER INFORMATION: Peg3-Peg3, where Peg3 is 8-amino-3,6-
      dioxaoctanoyl group

<400> SEQUENCE: 294

Lys Glu Lys
1

<210> SEQ ID NO 295
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-isoGlu
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 295

Lys Glu Lys
1

<210> SEQ ID NO 296
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-betaAla, where betaAla is 3-
      Aminopropanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 296

Lys Glu Lys
1

<210> SEQ ID NO 297
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 297

Lys Glu Lys
1

<210> SEQ ID NO 298
```

```
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 298

Lys Glu Lys
1

<210> SEQ ID NO 299
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 299

Lys Glu Lys
1

<210> SEQ ID NO 300
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 300

Lys Glu Lys
1

<210> SEQ ID NO 301
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-isoLys
<220> FEATURE:
```

```
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 301

Lys Glu Lys
1

<210> SEQ ID NO 302
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-isoLys
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 302

Lys Glu Lys
1

<210> SEQ ID NO 303
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-isoLys
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 303

Lys Glu Lys
1

<210> SEQ ID NO 304
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-isoLys
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 304

Lys Glu Lys
1

<210> SEQ ID NO 305
<211> LENGTH: 3
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-isoLys
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 305

Lys Glu Lys
1

<210> SEQ ID NO 306
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-[4-aminobutanoyl]
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 306

Lys Glu Lys
1

<210> SEQ ID NO 307
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-[4-aminobutanoyl]
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 307

Lys Glu Lys
1

<210> SEQ ID NO 308
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-[4-aminobutanoyl]
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group
```

<400> SEQUENCE: 308

Lys Glu Lys
1

<210> SEQ ID NO 309
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-[4-aminobutanoyl]
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 309

Lys Glu Lys
1

<210> SEQ ID NO 310
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-[4-aminobutanoyl]
<220> FEATURE:
<221> NAME/KEY: MOD_RES
<222> LOCATION: (3)..(3)
<223> OTHER INFORMATION: Peg3-Peg3, where Peg3 is 8-amino-3,6-
      dioxaoctanoyl group

<400> SEQUENCE: 310

Lys Glu Lys
1

<210> SEQ ID NO 311
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-isoGlu
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 311

Lys Glu Lys
1

<210> SEQ ID NO 312
<211> LENGTH: 3
<212> TYPE: PRT
<213> ORGANISM: Artificial Sequence
<220> FEATURE:
<223> OTHER INFORMATION: Synthetic Construct

```
<220> FEATURE:
<221> NAME/KEY: MOD_RES
<222> LOCATION: (1)..(1)
<223> OTHER INFORMATION: [Tetradecanoyl]-isoGlu
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 312

Lys Glu Lys
1

<210> SEQ ID NO 313
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-isoGlu
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 313

Lys Glu Lys
1

<210> SEQ ID NO 314
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-isoGlu
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 314

Lys Glu Lys
1

<210> SEQ ID NO 315
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-isoGlu
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 315

Lys Glu Lys
```

```
<210> SEQ ID NO 316
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 316

Lys Glu Lys
1

<210> SEQ ID NO 317
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 317

Lys Glu Lys
1

<210> SEQ ID NO 318
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 318

Lys Glu Lys
1

<210> SEQ ID NO 319
<211> LENGTH: 3
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MOD_RES
<222> LOCATION: (1)..(1)
<223> OTHER INFORMATION: [Octadecanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 319

Lys Glu Lys
1

<210> SEQ ID NO 320
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-betaAla, where betaAla is
      3-Aminopropanoyl
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 320

Lys Glu Lys
1

<210> SEQ ID NO 321
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Dodecanoyl]-isoLys
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 321

Lys Glu Lys
1

<210> SEQ ID NO 322
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-isoLys
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 322
```

Lys Glu Lys
1

<210> SEQ ID NO 323
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-isoLys
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 323

Lys Glu Lys
1

<210> SEQ ID NO 324
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-isoLys
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 324

Lys Glu Lys
1

<210> SEQ ID NO 325
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Eicosanoyl]-isoLys
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 325

Lys Glu Lys
1

<210> SEQ ID NO 326
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)

```
<223> OTHER INFORMATION: [Dodecanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 326

Lys Glu Lys
1

<210> SEQ ID NO 327
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Tetradecanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 327

Lys Glu Lys
1

<210> SEQ ID NO 328
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Hexadecanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 328

Lys Glu Lys
1

<210> SEQ ID NO 329
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: [Octadecanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, where Peg3 is 8-amino-3,6-
      dioxaoctanoyl group

<400> SEQUENCE: 329

Lys Glu Lys
1
```

```
<210> SEQ ID NO 330
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [Eicosanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, wherein Peg-3 is an an 8-amino-
      3,6-dioxaoctanoyl group

<400> SEQUENCE: 330

Lys Glu Lys
1

<210> SEQ ID NO 331
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: isoGlu-Peg3, wherein Peg-3 is an an 8-amino-
      3,6-dioxaoctanoyl group

<400> SEQUENCE: 331

Lys Glu Lys
1

<210> SEQ ID NO 332
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: isoGlu-Peg3, wherein Peg-3 is an an 8-amino-
      3,6-dioxaoctanoyl group

<400> SEQUENCE: 332

Lys Glu Lys
1

<210> SEQ ID NO 333
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
```

```
<223> OTHER INFORMATION: isoGlu-Peg3, wherein Peg-3 is an an 8-amino-
      3,6-dioxaoctanoyl group

<400> SEQUENCE: 333

Lys Glu Lys
1

<210> SEQ ID NO 334
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: isoGlu-Peg3, wherein Peg-3 is an an 8-amino-
      3,6-dioxaoctanoyl group

<400> SEQUENCE: 334

Lys Glu Lys
1

<210> SEQ ID NO 335
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: isoGlu-Peg3, wherein Peg-3 is an an 8-amino-
      3,6-dioxaoctanoyl group

<400> SEQUENCE: 335

Lys Glu Lys
1

<210> SEQ ID NO 336
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg-3 is an an 8-amino-3,6-dioxaoctanoyl
      group

<400> SEQUENCE: 336

Lys Glu Lys
1

<210> SEQ ID NO 337
<211> LENGTH: 3
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg-3 is an an 8-amino-3,6-dioxaoctanoyl
      group

<400> SEQUENCE: 337

Lys Glu Lys
1

<210> SEQ ID NO 338
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg-3 is an an 8-amino-3,6-dioxaoctanoyl
      group

<400> SEQUENCE: 338

Lys Glu Lys
1

<210> SEQ ID NO 339
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg-3 is an an 8-amino-3,6-dioxaoctanoyl
      group

<400> SEQUENCE: 339

Lys Glu Lys
1

<210> SEQ ID NO 340
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
```

```
<223> OTHER INFORMATION: betaAla-Peg3, wherein betaAla is
      3-Aminopropanoyl and Peg-3 is an an 8-amino-3,6-dioxaoctanoyl
      group

<400> SEQUENCE: 340

Lys Glu Lys
1

<210> SEQ ID NO 341
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: [4-aminobutanoyl]-Peg3, wherein Peg-3 is an an
      8-amino-3,6-dioxaoctanoyl group

<400> SEQUENCE: 341

Lys Glu Lys
1

<210> SEQ ID NO 342
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: [4-aminobutanoyl]-Peg3, wherein Peg-3 is an an
      8-amino-3,6-dioxaoctanoyl group

<400> SEQUENCE: 342

Lys Glu Lys
1

<210> SEQ ID NO 343
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: [4-aminobutanoyl]-Peg3, wherein Peg-3 is an an
      8-amino-3,6-dioxaoctanoyl group

<400> SEQUENCE: 343

Lys Glu Lys
1

<210> SEQ ID NO 344
<211> LENGTH: 3
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: [4-aminobutanoyl]-Peg3, wherein Peg-3 is an an
      8-amino-3,6-dioxaoctanoyl group

<400> SEQUENCE: 344

Lys Glu Lys
1

<210> SEQ ID NO 345
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: [4-aminobutanoyl]-Peg3, wherein Peg-3 is an an
      8-amino-3,6-dioxaoctanoyl group

<400> SEQUENCE: 345

Lys Glu Lys
1

<210> SEQ ID NO 346
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: isoLys-Peg3, wherein Peg-3 is an an 8-amino-
      3,6-dioxaoctanoyl group

<400> SEQUENCE: 346

Lys Glu Lys
1

<210> SEQ ID NO 347
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: isoLys-Peg3, wherein Peg-3 is an an 8-amino-
      3,6-dioxaoctanoyl group
```

```
<400> SEQUENCE: 347

Lys Glu Lys
1

<210> SEQ ID NO 348
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: isoLys-Peg3, wherein Peg-3 is an an 8-amino-
      3,6-dioxaoctanoyl group

<400> SEQUENCE: 348

Lys Glu Lys
1

<210> SEQ ID NO 349
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: isoLys-Peg3, wherein Peg3 is an 8-amino-3,6-
      dioxaoctanoyl group

<400> SEQUENCE: 349

Lys Glu Lys
1

<210> SEQ ID NO 350
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: isoLys-Peg3, wherein Peg3 is an 8-amino-3,6-
      dioxaoctanoyl group

<400> SEQUENCE: 350

Lys Glu Lys
1

<210> SEQ ID NO 351
<211> LENGTH: 3
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 351

Lys Glu Lys
1

<210> SEQ ID NO 352
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 352

Lys Glu Lys
1

<210> SEQ ID NO 353
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 353

Lys Glu Lys
1

<210> SEQ ID NO 354
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 354

Lys Glu Lys
1
```

```
<210> SEQ ID NO 355
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 355

Lys Glu Lys
1

<210> SEQ ID NO 356
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: BetaAla-Peg3-Peg3, wherein betaAla is
      3-Aminopropanoyl and Peg3 is an 8-amino-3,6-dioxaoctanoyl group

<400> SEQUENCE: 356

Lys Glu Lys
1

<210> SEQ ID NO 357
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: betaAla-Peg3-Peg3, wherein betaAla is
      3-Aminopropanoyl and Peg3 is an 8-amino-3,6-dioxaoctanoyl group

<400> SEQUENCE: 357

Lys Glu Lys
1

<210> SEQ ID NO 358
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
```

```
<221> NAME/KEY: MOD_RES
<222> LOCATION: (3)..(3)
<223> OTHER INFORMATION: betaAla-Peg3-Peg3, wherein betaAla is
      3-Aminopropanoyl and Peg3 is an 8-amino-3,6-dioxaoctanoyl group

<400> SEQUENCE: 358

Lys Glu Lys
1

<210> SEQ ID NO 359
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: betaAla-Peg3-Peg3, wherein betaAla is
      3-Aminopropanoyl and Peg3 is an 8-amino-3,6-dioxaoctanoyl group

<400> SEQUENCE: 359

Lys Glu Lys
1

<210> SEQ ID NO 360
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [Eicosanoyl]-betaAla, wherein betaAla is
      3-Aminopropanoyl
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 360

Lys Glu Lys
1

<210> SEQ ID NO 361
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 361

Lys Glu Lys
1

<210> SEQ ID NO 362
```

```
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 362

Lys Glu Lys
1

<210> SEQ ID NO 363
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 363

Lys Glu Lys
1

<210> SEQ ID NO 364
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 364

Lys Glu Lys
1

<210> SEQ ID NO 365
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
```

8-amino-3,6-dioxaoctanoyl group

<400> SEQUENCE: 365

Lys Glu Lys
1

<210> SEQ ID NO 366
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 366

Lys Glu Lys
1

<210> SEQ ID NO 367
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 367

Lys Glu Lys
1

<210> SEQ ID NO 368
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 368

Lys Glu Lys
1

<210> SEQ ID NO 369
<211> LENGTH: 3
<212> TYPE: PRT
<213> ORGANISM: Artificial Sequence
<220> FEATURE:

```
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 369

Lys Glu Lys
1

<210> SEQ ID NO 370
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 370

Lys Glu Lys
1

<210> SEQ ID NO 371
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 371

Lys Glu Lys
1

<210> SEQ ID NO 372
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 372
```

Lys Glu Lys
1

<210> SEQ ID NO 373
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 373

Lys Glu Lys
1

<210> SEQ ID NO 374
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 374

Lys Glu Lys
1

<210> SEQ ID NO 375
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 375

Lys Glu Lys
1

<210> SEQ ID NO 376
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)

```
<223> OTHER INFORMATION: Dodecanoyl
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 376

Lys Glu Lys
1

<210> SEQ ID NO 377
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 377

Lys Glu Lys
1

<210> SEQ ID NO 378
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [Hexadecanoyl]-betaAla, wherein betaAla is
      3-Aminopropanoyl
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 378

Lys Glu Lys
1

<210> SEQ ID NO 379
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 379

Lys Glu Lys
1
```

```
<210> SEQ ID NO 380
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 380

Lys Glu Lys
1

<210> SEQ ID NO 381
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 381

Lys Glu Lys
1

<210> SEQ ID NO 382
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 382

Lys Glu Lys
1

<210> SEQ ID NO 383
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
```

```
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 383

Lys Glu Lys
1

<210> SEQ ID NO 384
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 384

Lys Glu Lys
1

<210> SEQ ID NO 385
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 385

Lys Glu Lys
1

<210> SEQ ID NO 386
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 386

Lys Glu Lys
1

<210> SEQ ID NO 387
<211> LENGTH: 3
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Tetradecanoyl
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 387

Lys Glu Lys
1

<210> SEQ ID NO 388
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hexadecanoyl
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 388

Lys Glu Lys
1

<210> SEQ ID NO 389
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Octadecanoyl
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 389

Lys Glu Lys
1

<210> SEQ ID NO 390
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Eicosanoyl
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group
```

```
<400> SEQUENCE: 390

Lys Glu Lys
1

<210> SEQ ID NO 391
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]

<400> SEQUENCE: 391

Lys Glu Lys
1

<210> SEQ ID NO 392
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]

<400> SEQUENCE: 392

Lys Glu Lys
1

<210> SEQ ID NO 393
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]

<400> SEQUENCE: 393

Lys Glu Lys
1

<210> SEQ ID NO 394
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]

<400> SEQUENCE: 394

Lys Glu Lys
1

<210> SEQ ID NO 395
<211> LENGTH: 3
<212> TYPE: PRT
<213> ORGANISM: Artificial Sequence
<220> FEATURE:
```

```
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]

<400> SEQUENCE: 395

Lys Glu Lys
1

<210> SEQ ID NO 396
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 396

Lys Glu Lys
1

<210> SEQ ID NO 397
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 397

Lys Glu Lys
1

<210> SEQ ID NO 398
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 398

Lys Glu Lys
1

<210> SEQ ID NO 399
```

```
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 399

Lys Glu Lys
1

<210> SEQ ID NO 400
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 400

Lys Glu Lys
1

<210> SEQ ID NO 401
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 401

Lys Glu Lys
1

<210> SEQ ID NO 402
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
``` dioxaoctanoyl group

<400> SEQUENCE: 402

Lys Glu Lys
1

<210> SEQ ID NO 403
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
    dioxaoctanoyl group

<400> SEQUENCE: 403

Lys Glu Lys
1

<210> SEQ ID NO 404
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
    dioxaoctanoyl group

<400> SEQUENCE: 404

Lys Glu Lys
1

<210> SEQ ID NO 405
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
    dioxaoctanoyl group

<400> SEQUENCE: 405

Lys Glu Lys
1

<210> SEQ ID NO 406
<211> LENGTH: 3
<212> TYPE: PRT
<213> ORGANISM: Artificial Sequence
<220> FEATURE:

<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 406

Lys Glu Lys
1

<210> SEQ ID NO 407
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 407

Lys Glu Lys
1

<210> SEQ ID NO 408
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 408

Lys Glu Lys
1

<210> SEQ ID NO 409
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 409

Lys Glu Lys
1

<210> SEQ ID NO 410
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 410

Lys Glu Lys
1

<210> SEQ ID NO 411
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-isoGlu
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 411

Lys Glu Lys
1

<210> SEQ ID NO 412
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-isoGlu
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 412

Lys Glu Lys
1

<210> SEQ ID NO 413
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)

```
<223> OTHER INFORMATION: [17-carboxy-Heptadecanoyl]-isoGlu
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 413

Lys Glu Lys
1

<210> SEQ ID NO 414
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoGlu
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 414

Lys Glu Lys
1

<210> SEQ ID NO 415
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-isoGlu
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 415

Lys Glu Lys
1

<210> SEQ ID NO 416
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-[4-aminobutanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 416

Lys Glu Lys
1
```

```
-continued

<210> SEQ ID NO 417
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-[4-aminobutanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 417

Lys Glu Lys
1

<210> SEQ ID NO 418
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-[4-aminobutanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 418

Lys Glu Lys
1

<210> SEQ ID NO 419
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-[4-aminobutanoyl]
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 419

Lys Glu Lys
1

<210> SEQ ID NO 420
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-[4-aminobutanoyl]
<220> FEATURE:
<221> NAME/KEY: MOD_RES
<222> LOCATION: (3)..(3)
```

```
<223> OTHER INFORMATION: Peg3, wherein Peg3 is an 8-amino-3,6-
      dioxaoctanoyl group

<400> SEQUENCE: 420

Lys Glu Lys
1

<210> SEQ ID NO 421
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-isoLys
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 421

Lys Glu Lys
1

<210> SEQ ID NO 422
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-isoLys
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 422

Lys Glu Lys
1

<210> SEQ ID NO 423
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-isoLys
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 423

Lys Glu Lys
1

<210> SEQ ID NO 424
<211> LENGTH: 3
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoLys
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 424

Lys Glu Lys
1

<210> SEQ ID NO 425
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-isoLys
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 425

Lys Glu Lys
1

<210> SEQ ID NO 426
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 426

Lys Glu Lys
1

<210> SEQ ID NO 427
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group
```

```
<400> SEQUENCE: 427

Lys Glu Lys
1

<210> SEQ ID NO 428
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 428

Lys Glu Lys
1

<210> SEQ ID NO 429
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 429

Lys Glu Lys
1

<210> SEQ ID NO 430
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3, wherein Peg3 is an 8-amino-3,6-
      dioxaoctanoyl group

<400> SEQUENCE: 430

Lys Glu Lys
1

<210> SEQ ID NO 431
<211> LENGTH: 3
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-isoGlu
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 431

Lys Glu Lys
1

<210> SEQ ID NO 432
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-isoGlu
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 432

Lys Glu Lys
1

<210> SEQ ID NO 433
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-isoGlu
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 433

Lys Glu Lys
1

<210> SEQ ID NO 434
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoGlu
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group
```

```
<400> SEQUENCE: 434

Lys Glu Lys
1

<210> SEQ ID NO 435
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-isoGlu
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 435

Lys Glu Lys
1

<210> SEQ ID NO 436
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 436

Lys Glu Lys
1

<210> SEQ ID NO 437
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 437

Lys Glu Lys
1

<210> SEQ ID NO 438
<211> LENGTH: 3
<212> TYPE: PRT
<213> ORGANISM: Artificial Sequence
<220> FEATURE:
```

```
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 438

Lys Glu Lys
1

<210> SEQ ID NO 439
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 439

Lys Glu Lys
1

<210> SEQ ID NO 440
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 440

Lys Glu Lys
1

<210> SEQ ID NO 441
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-isoLys
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group
```

<400> SEQUENCE: 441

Lys Glu Lys
1

<210> SEQ ID NO 442
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-isoLys
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 442

Lys Glu Lys
1

<210> SEQ ID NO 443
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-isoLys
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 443

Lys Glu Lys
1

<210> SEQ ID NO 444
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoLys
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 444

Lys Glu Lys
1

<210> SEQ ID NO 445
<211> LENGTH: 3
<212> TYPE: PRT
<213> ORGANISM: Artificial Sequence
<220> FEATURE:
<223> OTHER INFORMATION: Synthetic construct

```
<220> FEATURE:
<221> NAME/KEY: MOD_RES
<222> LOCATION: (1)..(1)
<223> OTHER INFORMATION: [21-carboxy-heneicosanoyl]-isoLys
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 445

Lys Glu Lys
1

<210> SEQ ID NO 446
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-[4-aminobutanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 446

Lys Glu Lys
1

<210> SEQ ID NO 447
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-[4-aminobutanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 447

Lys Glu Lys
1

<210> SEQ ID NO 448
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-[4-aminobutanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 448

Lys Glu Lys
```

```
<210> SEQ ID NO 449
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-[4-aminobutanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 449

Lys Glu Lys
1

<210> SEQ ID NO 450
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-[4-aminobutanoyl]
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 450

Lys Glu Lys
1

<210> SEQ ID NO 451
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-isoGlu
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 451

Lys Glu Lys
1

<210> SEQ ID NO 452
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-isoGlu
```

```
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 452

Lys Glu Lys
1

<210> SEQ ID NO 453
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-isoGlu
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 453

Lys Glu Lys
1

<210> SEQ ID NO 454
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoGlu
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 454

Lys Glu Lys
1

<210> SEQ ID NO 455
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-isoGlu
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 455

Lys Glu Lys
1

<210> SEQ ID NO 456
```

```
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 456

Lys Glu Lys
1

<210> SEQ ID NO 457
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 457

Lys Glu Lys
1

<210> SEQ ID NO 458
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 458

Lys Glu Lys
1

<210> SEQ ID NO 459
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-betaAla, wherein
      betaAla is 3-Aminopropanoyl
```

```
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 459

Lys Glu Lys
1

<210> SEQ ID NO 460
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 460

Lys Glu Lys
1

<210> SEQ ID NO 461
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-isoLys
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 461

Lys Glu Lys
1

<210> SEQ ID NO 462
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-isoLys
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 462

Lys Glu Lys
1
```

```
<210> SEQ ID NO 463
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-isoLys
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 463

Lys Glu Lys
1

<210> SEQ ID NO 464
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoLys
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 464

Lys Glu Lys
1

<210> SEQ ID NO 465
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-isoLys
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 465

Lys Glu Lys
1

<210> SEQ ID NO 466
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]-[4-aminobutanoyl]
<220> FEATURE:
<221> NAME/KEY: MOD_RES
<222> LOCATION: (3)..(3)
```

```
<223> OTHER INFORMATION: Peg3-Peg3-Peg3, wherein Peg3 is an 8-amino-3,6-
      dioxaoctanoyl group

<400> SEQUENCE: 466

Lys Glu Lys
1

<210> SEQ ID NO 467
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 467

Lys Glu Lys
1

<210> SEQ ID NO 468
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 468

Lys Glu Lys
1

<210> SEQ ID NO 469
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 469

Lys Glu Lys
1

<210> SEQ ID NO 470
<211> LENGTH: 3
<212> TYPE: PRT
<213> ORGANISM: Artificial Sequence
```

<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-[4-aminobutanoyl]
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 470

Lys Glu Lys
1

<210> SEQ ID NO 471
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: isoGlu-Peg3, wherein Peg3 is an 8-amino-3,6-
      dioxaoctanoyl group

<400> SEQUENCE: 471

Lys Glu Lys
1

<210> SEQ ID NO 472
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: isoGlu-Peg3, wherein Peg3 is an 8-amino-3,6-
      dioxaoctanoyl group

<400> SEQUENCE: 472

Lys Glu Lys
1

<210> SEQ ID NO 473
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: isoGlu-Peg3, wherein Peg3 is an 8-amino-3,6-
      dioxaoctanoyl group

<400> SEQUENCE: 473

Lys Glu Lys
1

<210> SEQ ID NO 474
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: isoGlu-Peg3, wherein Peg3 is an 8-amino-3,6-
    dioxaoctanoyl group

<400> SEQUENCE: 474

Lys Glu Lys
1

<210> SEQ ID NO 475
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: isoGlu-Peg3, wherein Peg3 is an 8-amino-3,6-
    dioxaoctanoyl group

<400> SEQUENCE: 475

Lys Glu Lys
1

<210> SEQ ID NO 476
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: betaAla-Peg3, wherein betaAla is
    3-Aminopropanoyl and Peg3 is an 8-amino-3,6-dioxaoctanoyl group

<400> SEQUENCE: 476

Lys Glu Lys
1

<210> SEQ ID NO 477
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES

```
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg3 is an 8-amino-3,6-dioxaoctanoyl group

<400> SEQUENCE: 477

Lys Glu Lys
1

<210> SEQ ID NO 478
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg3 is an 8-amino-3,6-dioxaoctanoyl group

<400> SEQUENCE: 478

Lys Glu Lys
1

<210> SEQ ID NO 479
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg3 is an 8-amino-3,6-dioxaoctanoyl group

<400> SEQUENCE: 479

Lys Glu Lys
1

<210> SEQ ID NO 480
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: betaAla-Peg3, wherein betaAla is
      3-Aminopropanoyl and Peg3 is an 8-amino-3,6-dioxaoctanoyl group

<400> SEQUENCE: 480

Lys Glu Lys
1
```

<210> SEQ ID NO 481
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: [4-aminobutanoyl]-Peg3, wherein Peg3 is an
      8-amino-3,6-dioxaoctanoyl group

<400> SEQUENCE: 481

Lys Glu Lys
1

<210> SEQ ID NO 482
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: [4-aminobutanoyl]-Peg3, wherein Peg3 is an
      8-amino-3,6-dioxaoctanoyl group

<400> SEQUENCE: 482

Lys Glu Lys
1

<210> SEQ ID NO 483
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: [4-aminobutanoyl]-Peg3, wherein Peg3 is an
      8-amino-3,6-dioxaoctanoyl group

<400> SEQUENCE: 483

Lys Glu Lys
1

<210> SEQ ID NO 484
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES

```
<222> LOCATION: (3)..(3)
<223> OTHER INFORMATION: [4-aminobutanoyl]-Peg3, wherein Peg3 is an
      8-amino-3,6-dioxaoctanoyl group

<400> SEQUENCE: 484

Lys Glu Lys
1

<210> SEQ ID NO 485
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: [4-aminobutanoyl]-Peg3, wherein Peg3 is an
      8-amino-3,6-dioxaoctanoyl group

<400> SEQUENCE: 485

Lys Glu Lys
1

<210> SEQ ID NO 486
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: isoLys-Peg3, wherein Peg3 is an 8-amino-3,6-
      dioxaoctanoyl group

<400> SEQUENCE: 486

Lys Glu Lys
1

<210> SEQ ID NO 487
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: isoLys-Peg3, wherein Peg3 is an 8-amino-3,6-
      dioxaoctanoyl group

<400> SEQUENCE: 487

Lys Glu Lys
1

<210> SEQ ID NO 488
<211> LENGTH: 3
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: isoLys-Peg3, wherein Peg3 is an 8-amino-3,6-
      dioxaoctanoyl group

<400> SEQUENCE: 488

Lys Glu Lys
1

<210> SEQ ID NO 489
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: isoLys-Peg3, wherein Peg3 is an 8-amino-3,6-
      dioxaoctanoyl group

<400> SEQUENCE: 489

Lys Glu Lys
1

<210> SEQ ID NO 490
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: isoLys-Peg3,wherein Peg3 is an 8-amino-3,6-
      dioxaoctanoyl group

<400> SEQUENCE: 490

Lys Glu Lys
1

<210> SEQ ID NO 491
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group
```

```
<400> SEQUENCE: 491

Lys Glu Lys
1

<210> SEQ ID NO 492
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 492

Lys Glu Lys
1

<210> SEQ ID NO 493
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 493

Lys Glu Lys
1

<210> SEQ ID NO 494
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 494

Lys Glu Lys
1

<210> SEQ ID NO 495
<211> LENGTH: 3
<212> TYPE: PRT
<213> ORGANISM: Artificial Sequence
<220> FEATURE:
<223> OTHER INFORMATION: Synthetic construct
<220> FEATURE:
```

<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: isoGlu-Peg3-Peg3, wherein Peg3 is an 8-amino-
      3,6-dioxaoctanoyl group

<400> SEQUENCE: 495

Lys Glu Lys
1

<210> SEQ ID NO 496
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: betaAla-Peg3-Peg3, wherein betaAla is
      3-Aminopropanoyl and Peg3 is an 8-amino-3,6-dioxaoctanoyl group

<400> SEQUENCE: 496

Lys Glu Lys
1

<210> SEQ ID NO 497
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: betaAla-Peg3-Peg3, wherein betaAla is
      3-Aminopropanoyl and Peg3 is an 8-amino-3,6-dioxaoctanoyl group

<400> SEQUENCE: 497

Lys Glu Lys
1

<210> SEQ ID NO 498
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: betaAla-Peg3-Peg3, wherein betaAla is
      3-Aminopropanoyl and Peg3 is an 8-amino-3,6-dioxaoctanoyl group

<400> SEQUENCE: 498

Lys Glu Lys
1

```
<210> SEQ ID NO 499
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: betaAla-Peg3-Peg3, wherein betaAla is
      3-Aminopropanoyl and Peg3 is an 8-amino-3,6-dioxaoctanoyl group

<400> SEQUENCE: 499

Lys Glu Lys
1

<210> SEQ ID NO 500
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3, wherein Peg3 is an 8-amino-3,6-
      dioxaoctanoyl group

<400> SEQUENCE: 500

Lys Glu Lys
1

<210> SEQ ID NO 501
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 501

Lys Glu Lys
1

<210> SEQ ID NO 502
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
```

```
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 502

Lys Glu Lys
1

<210> SEQ ID NO 503
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 503

Lys Glu Lys
1

<210> SEQ ID NO 504
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 504

Lys Glu Lys
1

<210> SEQ ID NO 505
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: [4-aminobutanoyl]-Peg3-Peg3, wherein Peg3 is an
      8-amino-3,6-dioxaoctanoyl group

<400> SEQUENCE: 505

Lys Glu Lys
1

<210> SEQ ID NO 506
```

```
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 506

Lys Glu Lys
1

<210> SEQ ID NO 507
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 507

Lys Glu Lys
1

<210> SEQ ID NO 508
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 508

Lys Glu Lys
1

<210> SEQ ID NO 509
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
```

3,6-dioxaoctanoyl group

<400> SEQUENCE: 509

Lys Glu Lys
1

<210> SEQ ID NO 510
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: isoLys-Peg3-Peg3, wherein Peg3 is an 8-amino-
      3,6-dioxaoctanoyl group

<400> SEQUENCE: 510

Lys Glu Lys
1

<210> SEQ ID NO 511
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 511

Lys Glu Lys
1

<210> SEQ ID NO 512
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 512

Lys Glu Lys
1

<210> SEQ ID NO 513
<211> LENGTH: 3
<212> TYPE: PRT
<213> ORGANISM: Artificial Sequence
<220> FEATURE:

<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 513

Lys Glu Lys
1

<210> SEQ ID NO 514
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 514

Lys Glu Lys
1

<210> SEQ ID NO 515
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: isoGlu-Peg3-Peg3-Peg3, wherein Peg3 is an
      8-amino-3,6-dioxaoctanoyl group

<400> SEQUENCE: 515

Lys Glu Lys
1

<210> SEQ ID NO 516
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 516

Lys Glu Lys
1

<210> SEQ ID NO 517
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 517

Lys Glu Lys
1

<210> SEQ ID NO 518
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-betaAla, wherein
      betaAla is 3-Aminopropanoyl
<220> FEATURE:
<221> NAME/KEY: MOD_RES
<222> LOCATION: (3)..(3)
<223> OTHER INFORMATION: Peg3-Peg3-Peg3, wherein Peg3 is an 8-amino-3,6-
      dioxaoctanoyl group

<400> SEQUENCE: 518

Lys Glu Lys
1

<210> SEQ ID NO 519
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 519

Lys Glu Lys
1

<210> SEQ ID NO 520
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES

```
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: betaAla-Peg3-Peg3-Peg3, wherein betaAla is
      3-Aminopropanoyl and Peg3 is an 8-amino-3,6-dioxaoctanoyl group

<400> SEQUENCE: 520

Lys Glu Lys
1

<210> SEQ ID NO 521
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 521

Lys Glu Lys
1

<210> SEQ ID NO 522
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 522

Lys Glu Lys
1

<210> SEQ ID NO 523
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 523

Lys Glu Lys
1
```

<210> SEQ ID NO 524
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 524

Lys Glu Lys
1

<210> SEQ ID NO 525
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: [4-aminobutanoyl]-Peg3-Peg3-Peg3, wherein Peg3
      is an 8-amino-3,6-dioxaoctanoyl group

<400> SEQUENCE: 525

Lys Glu Lys
1

<210> SEQ ID NO 526
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [13-carboxy-tridecanoyl]
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 526

Lys Glu Lys
1

<210> SEQ ID NO 527
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [15-carboxy-Pentadecanoyl]
<220> FEATURE:
<221> NAME/KEY: MOD_RES -continued

```
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 527

Lys Glu Lys
1

<210> SEQ ID NO 528
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 528

Lys Glu Lys
1

<210> SEQ ID NO 529
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 529

Lys Glu Lys
1

<210> SEQ ID NO 530
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [21-carboxy-heneicosanoyl]
<220> FEATURE:
<221> NAME/KEY: MOD_RES
<222> LOCATION: (3)..(3)
<223> OTHER INFORMATION: isoLys-Peg3-Peg3-Peg3, wherein Peg3 is an
      8-amino-3,6-dioxaoctanoyl group

<400> SEQUENCE: 530

Lys Glu Lys
1

<210> SEQ ID NO 531
<211> LENGTH: 3
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-isoGlu

<400> SEQUENCE: 531

Lys Glu Lys
1

<210> SEQ ID NO 532
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoGlu

<400> SEQUENCE: 532

Lys Glu Lys
1

<210> SEQ ID NO 533
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-isoLys

<400> SEQUENCE: 533

Lys Glu Lys
1

<210> SEQ ID NO 534
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-isoLys

<400> SEQUENCE: 534

Lys Glu Lys
1

<210> SEQ ID NO 535
<211> LENGTH: 3
<212> TYPE: PRT
<213> ORGANISM: Artificial Sequence
<220> FEATURE:
<223> OTHER INFORMATION: Synthetic construct.
<220> FEATURE:
<221> NAME/KEY: MOD_RES
<222> LOCATION: (1)..(1)
<223> OTHER INFORMATION: [17-carboxy-Heptadecanoyl]-betaAla, wherein
      betaAla is 3-Aminopropanoyl

<400> SEQUENCE: 535
```

Lys Glu Lys
1

<210> SEQ ID NO 536
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-betaAla, wherein
      betaAla is 3-Aminopropanoyl

<400> SEQUENCE: 536

Lys Glu Lys
1

<210> SEQ ID NO 537
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [17-carboxy-Heptadecanoyl]-[4-aminobutanoyl]

<400> SEQUENCE: 537

Lys Glu Lys
1

<210> SEQ ID NO 538
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: [19-carboxy-Nonadecanoyl]-[4-aminobutanoyl]

<400> SEQUENCE: 538

Lys Glu Lys
1

<210> SEQ ID NO 539
<211> LENGTH: 33
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is K([17-carboxy-heptadecanoyl]-isoGlu)
<220> FEATURE:
<221> NAME/KEY: MOD_RES
<222> LOCATION: (16)..(16)
<223> OTHER INFORMATION: Hydroxyl

```
<400> SEQUENCE: 539

His Xaa Asp Gly Ser Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
                20                  25                  30

Asp

<210> SEQ ID NO 540
<211> LENGTH: 33
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(16)
<223> OTHER INFORMATION: Xaa is [K([17-carboxy-heptadecanoyl]-isoGlu)]
<220> FEATURE:
<221> NAME/KEY: MOD_RES
<222> LOCATION: (33)..(33)
<223> OTHER INFORMATION: Hydroxyl

<400> SEQUENCE: 540

His Xaa Glu Gly Ser Phe Ser Ser Glu Leu Ala Thr Ile Leu Asp Xaa
1               5                   10                  15

Gln Ala Ala Arg Asp Phe Ile Ala Trp Leu Ile Gln His Lys Ile Thr
                20                  25                  30

Asp
```

The invention claimed is:

1. A dual agonist represented by the formula:

$R^1$—X*—$R^2$, wherein:

$R^1$ is hydrogen (Hy), $C_{1-4}$ alkyl, acetyl, formyl, benzoyl or trifluoroacetyl;

$R^2$ is $NH_2$ or OH;

X* is a peptide H[Aib]EGSFTSELATILDψQAARDFIAWLIQHKITD (SEQ ID NO: 38);

ψ is an L or D Lys residue whose side chain is conjugated to a substituent of formula $Z^1$—$Z^2$— and $Z^1$—$Z^2$— is [17-carboxy-heptadecanoyl]-isoGlu-, or a pharmaceutically acceptable salt thereof.

2. The dual agonist according to claim 1, wherein X* consists of the sequence:

(SEQ ID NO: 85)
H[Aib]EGSFTSELATILD[K*]QAARDFIAWLIQHKITD;

wherein K* indicates an L lysine residue in which the side chain is conjugated to the substituent $Z^1$—$Z^2$—, or a pharmaceutically acceptable salt thereof.

3. The dual agonist according to claim 2, which is:

(SEQ ID NO: 200)
Hy-H[Aib]EGSFTSELATILD[K([17-carboxy-heptadecanoyl]-isoGlu)]QAARDFIAWLIQHKITD-OH, or a pharmaceutically acceptable salt thereof.

4. A pharmaceutical composition comprising the dual agonist or pharmaceutically acceptable salt thereof according to claim 1, in admixture with a pharmaceutically acceptable carrier, an excipient or a vehicle.

5. A pharmaceutical composition comprising the dual agonist or pharmaceutically acceptable salt thereof according to claim 3, in admixture with a pharmaceutically acceptable carrier, an excipient or a vehicle.

* * * * *